US007566550B2

(12) United States Patent
Tyagi et al.

(10) Patent No.: US 7,566,550 B2
(45) Date of Patent: Jul. 28, 2009

(54) SCREENING METHOD FOR DEVELOPING DRUGS AGAINST PATHOGENIC MICROBES HAVING TWO-COMPONENT SYSTEM

(75) Inventors: Jaya Sivaswami Tyagi, New Delhi (IN); Deepak Kumar Saini, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/687,402

(22) Filed: Oct. 16, 2003

(65) Prior Publication Data

US 2004/0209319 A1 Oct. 21, 2004

Related U.S. Application Data

(60) Provisional application No. 60/418,837, filed on Oct. 16, 2002.

(51) Int. Cl.
*C12Q 1/48* (2006.01)
(52) U.S. Cl. .............................. 435/15; 435/21; 435/32; 435/194
(58) Field of Classification Search ................... 435/15, 435/21, 32, 194
See application file for complete search history.

(56) References Cited

U.S. PATENT DOCUMENTS 6,043,045 A * 3/2000 Hoch et al. .................... 435/17
6,162,627 A 12/2000 Inouye et al. ................ 435/194

FOREIGN PATENT DOCUMENTS

WO 03066838 8/2003

OTHER PUBLICATIONS

Dasgupta et al., 2000, Characterization of a two-component system, devR-devS, of *Mycobacterium tuberculosis*, Tubercle and Lung Disease, 80(3): 141-159.*
Anderson D.H., Harth G., Horwitz M.A. and Eisenberg D. (2001) An interfacial mechanism and a class of inhibitors inferred from two crystal structures of the *Mycobacterium tuberculosis* 30 kDa major secretory protein (Antigen 85B) a mycolyl transferase. J. Mol. Biol. 307, 671-681.
Armitige, L.Y., Jagannath, C., Wanger, A.R. and Norris, S.J. (2000) Disruption of gene encoding antigen 85A and 85B of *Mycobacterium tuberculosis* H37Rv: Effect on growth in culture and in macrophages. Infect. Immun. 68, 76-78.
Baikalov, I., Schroder, I., Kaczor—Grzeskowiak, M., Grzeskowiak, K., Gunsalus, R.P. and Dickerson, R.E. (1996) Structure of the *Escherichia coli* response regulator NarL. Biochemistry 35, 11053-11061.
Baltch, A.L., Smith, R.P., Ritz, W.J. and Bopp, L.H. (1998) Comparison of inhibitory and bactericidal activities and postantibiotic effects of LY333328 and Ampicillin used singly and in combination against vancomycin—resistant *Enterococcus faecium*. Antimicrob. Agents Chemother. 42, 2564-2568.

Barrett, J.F. and Hoch, J.A. (1998) Two-component signal transduction as a target for microbial anti-infective therapy. Antimicrob. Agents Chemother. 42, 1529-1536.
Barry, C.E. III, Slayden, R.A., Simpson, A.E. and Lee, R.E. (2000) Use of genomics and combinatorial chemistry in the development of new antimycobacterial drugs. Biochem. Pharmacol. 59, 221-231.
Boon, C., Li, R., Qi, R. and Dick, T. (2001) Proteins of *Mycobacterium bovis* BCG induced in Wayne dormancy model. J. Bacteriol. 182, 2672-2676.
Bradford, M. M. (1976) A rapid and sensitive method for the quantitation of microgram quantities of protein utilizin the principle of protein—dye binding. Anal. Biochem. 72, 248-254.
Chen, P., Ruiz, R.E., Li, Q., Silver, R.F. and Bishai, W.R. (2000) Construction and characterization of *M. tuberculosis* mutant lacking the alternate sigma factor, sigF. Infect. Immun. 68, 5575-5580.
Cole et al. (1998) Deciphering the biology of *Mycobacterium tuberculosis* from the complete genome sequence. Nature 393, 537-544.
Collins D.M., Kawakami R.P., de Lisle G.W., Pascopella L., Bloom B.R. and Jacobs W.R. Jr. (1995) Mutation of the principal sigma factor causes loss of virulence in a strain of the *Mycobacterium tuberculosis* complex. Proc. Natl Acad. Sci. USA 92, 8036-8040.
Cooper J.B., McIntyre K., Badasso M.O., Wood S.P., Zhang Y., Garbe T.R. and Young, D. (1995) X-ray structure analysis of the iron-dependent superoxide dismutase from *Mycobacterium tuberculosis* at 2.0 Angstroms resolution reveals novel dimer-dimer interactions. J. Mol. Biol. 246, 531-544.
Cox J.S., Chen B., McNeil M. and Jacobs W.R. Jr. (1999) Complex lipid determines tissue-specific replication of Mycobacterium tuberculosis in mice, Nature 402, 79-83.
Dasgupta, N., Kapur, V., Singh, K.K., Das, T.K., Sachdeva, S., Jyothisri, K. and Tyagi, J.S. (2000) Characterization of a two-component system, devR-devS, of *Mycobacterium tuberculosis*. Tuber. Lung Dis. 80, 141-159.
DeMaio J., Zhang Y., Ko C., Young D.B. and Bishai W.R. (1996) A stationary-phase stress-response sigma factor from *Mycobacterium tuberculosis*. Proc. Natl. Acad. Sci. (USA) 93, 2790-2794.

(Continued)

*Primary Examiner*—Leon B. Lankford, Jr.
*Assistant Examiner*—Susan E. Fernandez
(74) *Attorney, Agent, or Firm*—Sughrue Mion, PLLC

(57) ABSTRACT

The present invention relates to a package of screening methods for developing drugs against pathogenic microbes having two-component system of DevR-DevS and/or DevR-Rv2027c and its homologues, said method comprising steps of over-expressing DevR, DevS, and Rv2027c and their single domain derivatives including mutant variant proteins, autophosphorylating DevS, and Rv2027c proteins and thereafter, phosphotransfering to DevR and its derivatives in SDS-PAGE or High-throughput format in the presence of a test compound, and determining the drug-potential of the test compound, wherein the potential of the drug is inversely proportional to (i) the degree of autophosphorylation of DevS and Rv2027c, (ii). the degree of phosphotransfer-based dephosphorylation of DevR and/its single domain derivative, and (iii). the degree of dephosphorylation of phosphorylated species of DevS and Rv2027c and/their single domain derivatives, and a method of treatment, and a composition thereof.

10 Claims, 22 Drawing Sheets

OTHER PUBLICATIONS

Denis et al. (1999) Synthesis and antibacterial activity of HMR 3647, a new ketolide highly potent against erthryomycin—resistant and susceptible pathogens. *Bioorg. Med. Chem. Lett.* 9, 3075-3080.

Deschenes, R.J., Lin, H., Ault, A.D. and Fassler, J.S. (1999) Antifungal properties and target evaluation of three putative bacterial histidine kinase inhibitors. *Antimicrob. Agents Chemother.* 43, 1700-1703.

Domagala, J.M., Alessi, D., Cummings, M., et al. (1998) Bacterial two-component signalling as a therapeutic target in drug design: Inhibition of NRII by diphenolic methanes (bisphenols). *Adv. Exp. Med. Biol.* 456, 269-286.

Doukhan, L., Predich, M., Nair, G., Dussurget, O., Mandic-Mulec, I., Cole, S.T., Smith, D.R. and Smith, I. (1995) Genomic organization of the mycobacterial sigma gene cluster. *Gene* 165, 67-70.

Dziejman, M. and Mekalanos, J.J. (1995) two-component signal transduction and its role in the expression of bacterial virulence factors in Hock, J.A. and Silhavy, T.J. Eds. Two component signal transduction. Washington, DC. American Society for Microbiology. pp. 305-317.

El-Masry, A.H., Fahony, H.H. and Abdelwahed, S.H.A. (2000) Synthesis and anti microbial activity of some new benzimidazole derivatives. *Molecules* 5, 1429-1438.

Frechette, R.F., Beach, M.J., Bernstein, J. et al. (1997) Novel benzoxazine derivatives with inhibitory activity agains bacterial two-component signal transduction systems. Abstract No. 152, Book of Abstracts, 214th ACS National Meeting, Las Vegas, NV, USA.

Glickman, M.S., Cox, J.S. and Jacobs, W.R. Jr. (2000) A novel mycolic acid cyclopropane synthetase is required fo coding, persistence and virulence of *Mycobacterium tuberculosis*. *Mol. Cell* 5, 717-727.

Grange, J.M. (1992) The mystery of the mycobacterial 'persistor'. *Tuber. Lung Dis.* 73, 249-251.

Haydel, S.E., Dunlap, N.E. and Benjamin, W.H. Jr. (1999) In vitro evidence of two-component system phosphorylation between the *Mycobacterium tuberculosis* TrcR/ TrcS proteins *Micro. Patho.* 26 195-206.

Himpens, S., Locht, C. and Supply, P. (2000) Molecular characterization of the mycobacterial SenX3-RegX3 two-component system: evidence for autoregulation. *Microbiol.* 146, 3091-3098.

Jackson, M., Crick, D.C. and Brennan, P.J. (2000) Phosphatidylinositol is an essential phospholipid of mycobacteria *J. Biol.Chem.* 275, 30092-30099.

Kinger, A.K. and Tyagi, J.S. (1993) Identification and cloning of genes differentially expressed in the virulent strain of *Mycobacterium tuberculosis*. *Gene* 131, 113-117.

Klimesova, V., Koc, J., Pour, M., Stachel, J., Waisser, K. and Kaustova, J. (2002a) Synthesis and preliminary evaluation of benzimidazole derivatives as antimicrobial agents. *Eur. J. Med. Chem.* 37, 409-418.

Klimesova, V., Koc, J., Waisser, K. and Kaustova, J. (2002b) New benzimidazole derivatives as antimycobacterial agents. *II Farmaco*, 57, 259-265.

Kramer, MJ and Grunberg, E. (1973) Effect of ethidium bromide against transplantable tumors in mice and rats. *Chemotherapy*, 19, 254-258.

Phetsuksiri, B., Baulard, A.R., Cooper, A.M., Minnikin, D.E., Douglas, J.D., Besra, G.S. and Brennan, P.J. (1999) Antimycobacterial activities of isoxyl and new derivatives through the inhibition of mycolic acid synthesis. *Antimicrob. Chemother.* 43, 1042-1051.

Li, Z., Kelley, C., Collins, F., Rouse, D. and Morris, S. (1998) Expression of katG in *Mycobacteriun tuberculosis* is associated with its growth and persistence in mice and guinea pigs. *J. Infect. Dis.* 177, 1030-1035.

Macielag, M.J. and Goldschmidt, R. (2000) Inhibitors of bacterial two-component signalling system. *Exp. Opin. Invest. Drugs* 9, 2351-2369.

Manganelli, R., Voskuil, M.I., Schoolnik, G.K. and Smith, I. (2001) The *Mycobacterium tuberculosis* ECF sigma factor sigmaE: role in global gene expression and survival in macrophages. Mol. Microbiol. 41, 423-437.

Matsushita, M. and Janda, K.D. (2002) Histidine kinases as targets for new antimicrobial agents. *Bioor. Med. Chem.* 10, 855-867.

Mayuri, Bagchi, G., Das, T.K. and Tyagi, J.S. (2002) Molecular analysis of the dormancy response in *Mycobacterium smegmatis*. Expression analysis of the genes encoding DevR-DevS two-component system, Rv3134c and chaperone—crystalline homologues. *FEMS Microbiol. Lett.* 211, 231-237.

McKinney, J.D., Bentrup, K.H., Munoz-Elias, E.J., Miczak, A., Chen, B., Chen, W.T., Swenson, D., Sacchettini, J.C. Jacobs, W.R. Jr. and Russell, D.G.. (2000) Persistence of *M. tuberculosis* in macrophages and mice requires the glyoxylate shunt enzyme isocitrate lyase. *Nature* 406, 735-738.

Mitchison, D.A. (1998) How drug resistance emerges as a result of poor compliance during short—chemotherapy for tuberculosis. *Int. J. Tuberc. Lung Dis.* 2, 10-15.

Mukamolova G.V., Kaprelyants A.S., Young D.I., Young M. and Kell D.B. (1998) A bacterial cytokine. *Proc. Nat Acad. Sci. USA.* 95, 8916-8921.

Parkinson, J.S. and Kofoid, E.C. (1992) Communication modules in bacterial signalling proteins. *Ann. Rev. Genet.* 26, 71-112.

Parrish, N., Dick, J.D. and Bishai, W.R. (1998) Mechanisms of latency in *Mycobacterium tuberculosis*. *Trends Microbiol.* 6: 107-112.

Perez, E., Samper, S., Bordas, Y., Guilhot, C., Gicquel, B., and Martin, C. (2001) An essential role for phoP in *Mycobacterium tuberculosis* virulence. *Mol. Micro.* 41, 179-87.

Pohl, E., Holmes, R.K. and Hol, W.G. (1999) Crystal structure of the iron-dependent regulator (IdeR) from *Mycobacterium tuberculosis* shows both metal binding sites fully occupied. *J. Mol. Biol.* 285, 1145-1156.

Raman, S., Song, T., Puyang, X., Bardarov, S., Jacobs, W.R. Jr. and Husson, R.N. (2001) The alternative sigma factor SigH regulates major components of oxidative and heat stress responses in *Mycobacterium tuberculosis*. *J. Bacteriol.* 183, 6119-6125.

Ronning, D.R., Klabunde, T., Besra, G.S., Vissa, V.D., Belisle, J.T. and Sacchettini, J.C. (2000) Crystal structure of the secreted form of antigen 85C reveals potential targets for mycobacterial drugs and vaccines. *Nat. Struct. Biol.* 7 141-146.

Roychoudhary, S., Zielinski, N.A., Ninfa, A.J., Allen, N.E., Jungheim, L.N., Nicas, T.I. and Chakrabarty, A.M. (1993) Inhibitors of two-component signal transduction systems: Inhibition of alginate gene activation in *Pseudomonas aerugin osa*. *Proc. Natl. Acad. Sci. USA.* 90, 965-969.

Sherman, D.R., Voskuil, M., Schnappinger, D., Liao, R., Harrell, M.I. and Schoolnik, G.K. (2001) Regulation of the *Mycobacterium tuberculosis* hypoxia response gene encoding α—crystallin. *Proc. Natl. Acad. Sci. USA* 98, 7534-7539.

Stead, W.W. (1967) Pathogenesis of a first episode of chronic pulmonary tuberculosis in man: recrudescence of residuals of the primary infection or exogenous reinfection? *Am. Rev. Respir. Dis.* 95, 729-745.

Stead, W.W., Kerby, D.P., Schleuter, D.P. and Jordahl, C.W. (1968) The clinical spectrum of primary tuberculosis in adults. Confusion with reinfection in the pathogenesis of chronic tuberculosis. *Ann. Intern. Med.* 68, 731-745.

Stephenson, K., Yamaguchi, Y., Hoch, J.A. (2000) The mechanism of action of inhibitors of bacterial two-componen signal transduction systems. *J. Biol. Chem.* 275, 38900-38904.

Stock, A.M., Robinson, V.L. and. Goudreau, P.N. (2000) Two-component signal transduction. *Ann. Rev. Biochem* 69, 183-215.

Stock, J.B., Surette, M.G., Levit, M. and Park, P. (1995) Two-component signal transduction systems: structure-function relationships and mechanisms of catalysis. In: Hock, J.A. and Silhavy, T.J. Eds. Two component signal transduction. Washington, DC. American Society for Microbiology, pp. 25-51.

Stover, C.K., Warrener, P., VanDevanter, D.R., Sherman, D.R., Arain, T.M., Langhorne, M.H., Anderson, S.W., Towell, J.A., Yuan, Y., McMurray, D.N., Kreiswirth, B.E., Barry, C.E. III and Baker, W.R. (2000) A small molecul nitroimidaofuran drug candidate for treatment of tuberculosis. *Nature* 405, 962-66.

Strauch, M.A., De Mendoza, D. and Hoch, J.A. (1992) cis—Unsaturated fatty acids specifically inhibit a signal—transducing protein kinase required for initiation of sporulation in *B. subtilis*. *Mol. Microbiol.* 6, 2909-2917.

Ulijasz, A.T. and Weisblum, B. (1999) Dissecting the VanRS signal transduction pathway with specific inhibitors. *J. Bacteriol.* 181, 627-631.

Upton, A., Johnson, N., Sandy, J. and Sim, E. (2001) Arylamine N-acetyltransferases—of mice, men and microorganisms. *Trends Pharmacol. Sci.* 22, 140-146.

Urbanski, M.J., Xiang, M.A., Foleno, B.D. et al. (1997) Novel cyclohexene derivatives with histidine protein kinase inhibitory activity—potential new antibacterial agents. Abstract No. 270, Book of Abstracts, 214th ACS National Meeting, Las Vegas, NV, USA.

Wallis, N.G. (1999) Bacterial two-component signal transduction systems as drug targets. *Curr. Opin. Anti-infect. Invest. Drugs.* 1, 428-434.

Weber, I., Fritz, C., Ruttkowski, S., Kreft, A. and Bange, F.-C. (2000) Anaerobic nitrate reductase (*narGHJI*) activit of *Mybocaterium bovis* BCG in vitro and its contribution to virulence in immunodeficient mice. *Mol. Microbiol.* 35 1017-1025.

West, M.L. and Fairlie, D.P. (1995) Targeting HIV-1 protease: a test of drug-design methodologies. *Trends Pharmacol. Sci.* 16, 67-94.

WHO report on the Global Tuberculosis Epidemic (1998) WHO Geneva.

Wilson T.M., de Lisle, G.W. and Collins, D.M. (1995) Effect of *inhA* and *katG* on isoniazid resistance and virulence of *Mycobacterium bovis*. *Mol. Microbiol.* 15, 1009-1015.

Yuan, Y., Crane, D.C., Simpson, R.M., Zhu, Y.Q., Hickey, M.J., Sherman, D.R., and Barry, C.E. III. (1998) The 16 kDa a—crystalline (Acr) protein of *Mycobacterium tuberculosis* is required for growth in macrophages. *Proc. Natl. Acad. Sci.* USA 95, 9578-9583.

Zahrt, T.C. and Deretic, V., (2000) An essential two-component signal transduction system in *Mycobacterium tuberculosis*. *J. Bacteriol.* 182, 3832-3838.

Zahrt, T.C. and Deretic, V. (2001) *Mycobacterium tuberculosis* signal transduction system required for persistent infection. *Proc. Natl. Acad. Sci.* (USA) 98, 12706-11.

Zhang, Y. and Amzel, L.M. (2002) Tuberculosis drug targets. *Current Drug Targets* 3, 131-154.

\* cited by examiner

A.

B.

C.

A.

B.

C.

A. $DevS_{201}$

B. $DevS_{578}$

C. $Rv2027_{194}$

A.

B.

C.

A.

B.

C.

D.

E.

F.

A.

B.

A.

B.

A.

B.

A.

B.

A.

B.

C.

D.

A.

B.

C.

D.

A.

B.

SEQUENCE LISTING

```
<160> NUMBER OF SEQ ID NOS: 28

<210> SEQ ID NO 1
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 1
```

```
gcccatatgg taaaggtctt cttgg                                           25

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2 ccggctttt cgtcgacgag g                                                21

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 3
caacgtcgga tccgcgaact cgacg                                           25

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 4
ggcgccggga tcctggcact agg                                             23

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 5
cgacggatcc gcaatgcgtc ca                                              22

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 6
ggcgccggga tcctggcact agg                                             23

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 7
gcgagaagtg gaggatcctg acc                                             23

<210> SEQ ID NO 8
<211> LENGTH: 24
<212> TYPE: DNA
```

```
<213> ORGANISM: Artificial Sequence
<220> FEATURE:
<223> OTHER INFORMATION: Oligonucleotide primer

<400> SEQUENCE: 8
ggattgcgcg gatccgtcga cgcc                                              24

<210> SEQ ID NO 9
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 9
gcccgtgacc tccaagacca tgtcatccag cgg                                    33

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 10
ccgctggatg acatggtctt ggaggtcacg ggc                                    33

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 11
gacctccatg accaagtcat ccagcgg                                           27

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
ccgctggatg acttggtcat ggaggtc                                           27

<210> SEQ ID NO 13
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 13
gacctccatg acgatgtcat ccagcgg                                           27

<210> SEQ ID NO 14
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 14
ccgctggatg acatcgtcat ggaggtc                                           27
```

<210> SEQ ID NO 15
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 15
gaagcggtca gcgacgcggt tagacatg                                              28

<210> SEQ ID NO 16
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 16
catgtcgtaa ccgcgtcgct gaccgcttc                                             29

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 17
gcacgtgatc tgcaagacca cgtcatccag                                            30

<210> SEQ ID NO 18
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 18
ctggatgacg tggtcttgca gatcacgtgc                                            30

<210> SEQ ID NO 19
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 19
gcggatatgt cgtcgaagac atcaagggaa tg                                         32

<210> SEQ ID NO 20
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 20
cattcccttg atgtcttcga cgacatatcc gc                                         32

<210> SEQ ID NO 21
<211> LENGTH: 27
<212> TYPE: DNA
<213> ORGANISM: Artificial Sequence
<220> FEATURE:

-continued

<223> OTHER INFORMATION: Oligonucleotide primer

<400> SEQUENCE: 21
gtcgcggtgc tggttgtccg gttgccc                                27

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 22
gggcaaccgg acaaccagca ccgcgac                                27

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 23
cttcttggtc aatgaccacg aggtggtg                               28

<210> SEQ ID NO 24
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 24
caccacctcg tggtcattga ccaagaag                               28

<210> SEQ ID NO 25
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 25
cttcttggtc gataaccacg aggtgggtg                              29

<210> SEQ ID NO 26
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 26
cacccacctc gtggttatcg accaagaag                              29

<210> SEQ ID NO 27
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 27
gcggatatgt cgtcgaagac atcaagggaa tg                          32

-continued

```
<210> SEQ ID NO 28
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 28
cattcccttg atgtcttcga cgacatatcc gc                                32
```

SCREENING METHOD FOR DEVELOPING DRUGS AGAINST PATHOGENIC MICROBES HAVING TWO-COMPONENT SYSTEM

SPECIFICATION

The present application claims priority to U.S. Provisional Application Ser. No. 60/418,837, filed Oct. 16, 2002, which is incorporated herein by reference in its entirety.

FIELD OF THE PRESENT INVENTION

The present invention relates to screening methods designed for identifying drugs for use against pathogenic microbes. The screening method of the invention is a two-component system of DevR-DevS and/or DevR-Rv2027c and its homologues, wherein said method comprises the steps of over-expressing DevR, DevS, and Rv2027c and their single domain derivatives including mutant variant proteins, autophosphorylating DevS, and Rv2027c proteins and thereafter, phosphotransfering to DevR and its derivatives in SDS-PAGE or High-throughput format in the presence of a test compound, and determining the drug-potential of the test compound, wherein the potential of the drug is inversely proportional to (i) the degree of autophosphorylation of DevS and Rv2027c, (ii) the degree of phosphotransfer-based dephosphorylation of DevR and/its single domain derivative, and (iii) the degree of dephosphorylation of phosphorylated species of DevS and Rv2027c and their single domain derivatives. The present invention further provides compositions comprising the identified drugs and methods of treating pathogenic microbes using such compositions.

BACKGROUND OF THE PRESENT INVENTION

Tuberculosis is the leading cause of death from a single infection agent killing more than 3 million people per year worldwide. In the year 1998, the estimated numbers of Tuberculosis cases in India were 2,078,076 among which 935,134 cases were likely to be infectious (WHO report, 1998) and it has been nearly 40 years since the introduction of a novel compound for the treatment of *tuberculosis*.

The consequence of tuberculosis infection is clearly an outcome of the continuous interplay between the pathogen and the host immune defense. In most instances, the infected individual mounts an effective immune response that culminates in granuloma formation around the infective foci and cessation of disease progression. Clinical studies suggest that the bacilli within these granulomas are not killed but instead remain dormant (Grange, 1992; Stead, 1967; Stead et al., 1968). This is termed a latent infection. Natural TB infection without treatment can lead to latent infection, which can last a lifetime and approximately 10% of latent infections reactivate, resulting in active disease months to years after the initial infection (Stead et al., 1968). The large number of latently infected individuals presents a major impediment to reducing the incidence of tuberculosis and the rate of *M. tuberculosis* transmission. The adaptation of the *M. tuberculosis* during the spectrum of infection and disease, including prolonged survival within granulomas, is likely implemented through precise genetic pathways that are modulated by specific physiological and environmental conditions within host tissues. There is an urgent need to understand these pathways in order to devise novel and more directed strategies for the prevention, control and treatment of tuberculosis.

Rate limiting steps in metabolic pathways that are unique to prokaryotes, such as cell wall biosynthesis and DNA replication, have been traditional foci of anti-infectives. Their poor activity against slow growing and non-replicating bacteria is thought to be an important reason why currently used regimens take so long to eradicate infection (Parrish et al., 1998) and often fail to eradicate at all. The rapid explosion in our understanding of the *M. tuberculosis* genome and its metabolic pathways has provided an unprecedented opportunity to design drugs to novel metabolic targets.

Discovery of bacterial genes that play key roles in persistence has opened the way for the identification of molecules in dormant bacteria that can be targeted by new classes of drugs. Bacterial two-component systems belong to this class of novel targets (Barrett and Hoch, 1998).

Two-component signal transduction systems are the most basic form of sensory systems which involve direct response to environmental signals like stress ($O_2$ tension, pH), nutritional deficiencies (chemical compounds, biological analogs, ions), exposure to chemicals, toxins and changes in osmolarity, etc. to name a few. The two-component system consists of a basic sensory system comprising a transmembrane sensor histidine kinase which senses the environmental stimulus and undergoes autophosphorylation at a conserved histidine residue in an ATP-dependent manner (FIG. 1). The phosphorylated histidine sensor kinase then transfers the phosphoryl moiety to a conserved aspartate residue of the response regulator protein, the other half of the two-component system, which is predicted to possess DNA binding ability due to the presence of a conserved helix-turn-helix motif present in it. The phosphorylation status of the response regulator protein can alter its DNA binding potential/ability and consequently switch on or off the expression of the genes under its regulatory control. (Parkinson and Kofoid, 1992; Stock et al., 2000).

The complete genome sequencing of *M. tuberculosis* H37Rv, a virulent strain of *M. tuberculosis* capable of causing tuberculosis, revealed the presence of genes potentially coding for eleven complete two-component systems and seven orphan sensor kinase and response regulator proteins (Cole et al., 1998). Out of these systems only four systems have been characterized at biochemical level including DevR-DevS (described herein), DevR-Rv2027c (described herein), SenX3-RegX3 (Himpens et al., 2000) and TrcS-TrcR (Haydel et al., 1999). The DevR-DevS (Rv3133c-Rv3132c) two-component system has been suggested to play a regulatory role during oxygen limitation on account of its hypoxia-responsive pattern of gene expression (Tyagi, J S, DST report, October 2001; Boon et al., 2001, Sherman et al., 2001). Hypoxia is postulated to constitute a trigger for the onset of mycobacterial dormancy within granulomas. The DevR-DevS system is therefore a candidate for regulating dormancy of the tubercle bacili. On the basis of the experimental evidence which have been amassed about the role of this two component system in the virulence of *Mycobacterium tuberculosis*, DevR-DevS system is an appropriate choice as a target for the action of antibiotics to inhibit its putative function and subsequently eradicate/kill the tubercle bacilli or to prevent the bacilli from going into dormant stage. It can also be used to supplement conventional therapies and antibiotics which are not effective against the dormant bacilli. For screening the inhibitors against this two-component system, the phosphorylation pathways of DevR-DevS and DevR-Rv2027c (orphan sensor kinase highly homologous to DevS) were established at the biochemical level.

Drugs which inhibit two-component systems are expected to be specific for bacteria and not for humans since the latter are not reported to contain two-component systems. The involvement of the DevR-DevS two-component system, and particularly of response regulator, DevR in virulence provides an attractive target for chemotherapeutic agents directed tubercle bacilli (Kapur, V., Ph.D. Thesis, 2001; Tyagi and Kapur, PCT/IN02/00022). Isocitrate lyase (McKinney et al., 2000) a methyl transferase pcaA (Glickman et al., 2000), and a two-component system Rv0981-0982 (Zahrt and Deretic, 2001) have also been identified as crucial to the persistent state of the tubercle bacilli. These genes together with some other recently discovered targets like resuscitation factors (Mukamolova et al., 1998) which include 8 kDa secreted protein and proteins homologous to 16 kDa protein of *Micrococcus luteus* which act as resuscitation factor (Mukamolova et al., 1998), provide new avenues for improved therapy of tuberculosis (Barry et al., 2000).

A number of genes that have been earlier implicated in dormancy/persistence have been characterized at various levels. The three-dimensional crystal structures of some of the proteins involved have been characterized, including isocitrate lyase and antigen 85B (Armitige et al., 2000). Based on their 3-D structural lattices, rational drug design is currently underway in several laboratories. However, functional dissection of a mycobacterial regulatory network cascade involving a two-component system in general, and DevR-DevS system in particular, has not been accomplished yet. In this context DevR-DevS forms a potent target for attacking bacteria residing within granulomas. Oxygen limitation and hypoxia has been recently shown to upregulate the synthesis of DevR-DevS two-component system in *M. tuberculosis, M. bovis* BCG and *M. smegmatis* in an in vitro dormancy model (Tyagi, J S, DST report, October 2001; Sherman et al., 2001; Boon et al., 2001 and Mayuri et al., 2002). This finding has crucial implications for *M. tuberculosis* since hypoxia often is thought to be a characteristic environmental property of granulomas and a likely trigger for the initiation and/or maintenance of dormancy response. Since DevR is upregulated under hypoxia, modulation of gene activity by DevR is likely to be achieved through its putative DNA binding activity as is known to occur in other bacterial two-component system response regulators (Dziejman and Mekalanos, 1995). A number of genes induced during hypoxia and implicated in persistence therefore may be under regulation of DevR-DevS two-component system.

Besides candidate genes involved in persistence and/or dormancy response of *M. tuberculosis* as targets for antitubercular therapy, a number of other gene targets have also been suggested as intervention targets due to their critical role in *M. tuberculosis* survival and pathogenesis (Zhang and Amzel, 2002) including, (i) transcription factors like stationary-phase sigma factor SigB (Doukhan et al., 1995), SigF (DeMaio et al., 1996), global expression regulating sigma factor, SigE and SigH (Manganelli et al., 2001; Raman et al., 2001), (ii) virulence associated factors like RpoV (Collins et al., 1995), catalase-peroxidase, KatG (Wilson et al., 1995), complex lipid phthiocerol dimycocerosate (PDIM) and its transporter mmpL7 (Cox et al., 1999), (iii) cell-wall synthesis regulating genes like phosphatidylinositol synthetase (Jackson et al., 2000), fatty-acid synthase type II (Kremer et al., 1999) and (iv) two-component systems like MtrA which have been shown to be essential for *M. tuberculosis* survival (Zahrt and Deretic, 2000); PhoP/PhoQ and Rv0981/Rv0982 which regulates virulence (Perez et al., 2001; Zahrt and Deretic, 2001). In addition to these defined approaches there are many targets and/or genes in the *M. tuberculosis* which are under investigation on the basis of their homology to other known microbial genes involved in pathogenesis (Zhang and Amzel, 2002). Many other genes which are now targeted for antitubercular therapy are essentially the one whose 3-D structure has been elucidated and hence they can be used effectively in structure-based rational drug-design approach, for example arylamine N-acetyltransferases—NAT (Upton et al., 2001), iron-dependent regulator—IdeR (Pohl et al., 1999), antigen 85 complex (Ronning et al., 2000; Anderson et al., 2001), iron-dependent superoxide dismutase—SOD (Zhang et al., 1991; Cooper et al., 1995) and many others. Despite such a huge number of genes targeted for anti-tubercular therapy, no new interventions have been reported to date.

Chemical modification of existing classes of antibacterial agents continues to be a fruitful approach to the design of new antibiotics, as evidenced by the discovery of glycopeptides effective against vancomycin-resistant enterococci and ketolides with activity against streptomycin-resistant *S. pneumoniae* (Baltch et al., 1998; Denis et al., 1999). Such an approach was utilized for devising new anti-tubercular drugs like rifampicin derivatives like rifapentine etc. But, incremental changes in the structure of poorly efficacious antibacterials, however, are likely to afford analogues with a limited life span due to established resistance to the parent drug (Macielag and Goldschmidt, 2000). This further necessitates the development of completely novel and newer drug targets and therapeutic modalities effective against tuberculosis.

A scientifically appealing but largely unexplored approach was to inhibit the function or expression of virulence factors and/or regulatory elements like two-component systems. The two-component regulatory systems have received increasing attention both a novel antibacterial drug targets and as potential sites of action for virulence inhibitors (Barrett and Hoch, 1998; Wallis, 1999).

The two-component systems or sensor kinase or response regulator proteins as targets for new drugs or compounds have been utilized in recent past (Macielag and Goldschmidt, 2000). Reports from independent laboratories, including pharmaceutical companies, have provided various compounds with proven potential to inhibit the phosphorylation of sensor histidine kinases in particular in in vitro assays. However, to date such a strategy has not been attempted for developing antimycobacterial agents.

The vast majority of two-component system inhibitors described block the autophosphorylation of histidine sensor kinase component. However, the precise mode of action of such inhibitors has generally remained obscure due to lack of published enzyme kinetics data, making it difficult to develop a useful pharmacophore model. Moreover, most of the inhibitors in the literature were discovered before the structures of the sensor kinase catalytic domains were published.

Most of the sensor kinase inhibitors identified by broad-spectrum corporate library screening have turned out to be highly hydrophobic compounds which include, for example, isothiazolones (Ulijasz et al., 1999), fatty acid derivatives (Strauch et al., 1992), imidazolium salts (Roychoudhary et al., 1993), tyramine structural motifs like cyclohexene derivatives (Urbanski et al., 1997) and benoxazines (Frechette et al., 1997). Most of the identified compounds have shown efficacy in in vitro assays wherein they have shown the potential to inhibit the phosphorylation assays, which was used as the screening reaction or assay.

There are three main reasons for identifying and developing new antitubercular drugs: (i) to improve current treatment by shortening the total duration of treatment and/or by providing for more widely spaced intermittent treatment, (ii) to improve the treatment of MDR-TB, and (iii) to provide for more effective treatment of latent tuberculosis infection. These reasons summarize all the major drawbacks in existing antitubercular therapy and indicate the needs to be addressed.

Drug resistant forms of tuberculosis pose a serious threat to the successful outcome of a tuberculosis control programme in a community. Although many highly effective drugs such as isoniazid, rifampicin, ethambutol and pyrazinamide are available, poor compliance due in part to long treatment schedules (6 months is the standard duration) leads to high rates of treatment failure. There is an urgent need to implement the DOTS (Directly observed short course) treatment schedule to reduce the incidence and spread of tuberculosis in general and drug resistant forms in particular. Though conventional drug regimens comprising administration of rifampicin-isoniazid-pyrazinamide is very effective, the minimum inhibitory concentration (MIC) for all the three drugs is very close to the maximum serum concentration, which is limited by toxicity, resulting in poor therapeutic index for each. Serum concentration of these drugs may oscillate between levels above and below the MIC over the course of daily administration. This phenomenon, coupled with poor patient compliance over the course of this lengthy chemotherapy, has been proposed to be linked directly to the emergence of drug resistance (Mitchison, 1998). This ineffectiveness of current therapies is therefore directly responsible for both the very long duration of therapy and the emergence of resistance to drugs. Certain fourth generation quinolones including gatifloxacin and levamofloxacin etc. have shown certain degree of efficacy against many—a clinical isolates of mycobacteria including M. tuberculosis under in vitro conditions, but these drugs are also marred by the same intrinsic drawbacks like their limited efficacy under in vivo conditions, severe side-effects, high cost and rapid emergence of resistant isolates.

Therefore there is a pressing need to introduce new drugs that would be effective against resistant forms of tuberculosis and also reduce the duration and cost of chemotherapy. Although many lead compounds targeted against the conventional drug targets are being tested worldwide, no new drugs for tuberculosis have been introduced in the market over the last thirty years.

In addition, there is no drug available in the market today which can be used to tackle the ever expanding problem of latent tuberculosis. All the drugs which are used for combating tuberculosis, are effective only in the active disease conditions and are not able to eradicate the latent disease. Since the DevR-DevS two-component system has been implicated in the virulence and in dormancy particularly, targeting it would also provide a handle to counter the problem of latent tuberculosis. Technically, a genetic disruption of response regulator gene, devR of the DevR-DevS and/or DevR-Rv2027c two-component system signal transduction pathways is equivalent to an attenuated strain which is rapidly cleared off from the system and fails to cause any latent tuberculosis (Kapur, V., Ph.D. Thesis, 2001; Tyagi and Kapur, PCT/IN02/00022). Consequently disruption of DevR-DevS or DevR-Rv2027c signal transduction pathways by the means of inhibitors would be equivalent to their genetic disruption and a conventional therapy alongside this would effectively eradicate tubercle bacilli without allowing it to enter a dormant stage.

The utilization of two-component systems as screens for inhibitors have provided a number of inhibitor molecules which have shown potential to inhibit the autophosphorylation reaction of sensor kinases in in vitro assay systems. But, all the identified inhibitors and compounds for bacterial two-component systems suffer from the drawback of extreme hydrophobicity. Such high hydrophobicity of these molecules makes formulation and delivery of the compounds extremely difficult. Furthermore, the compounds showed minimal bioavailability and excessive plasma protein binding, Thus, the compounds have been ineffective in standard in vivo infection models.

The benzooxazines (Frechette et al., 1997) were designed with the goal of improving the hydrophobic/hydrophilic balance and the in vivo activity of the inhibitors. Though these compounds demonstrated good antibacterial activity, they also suffered from excessive protein binding, which hampered in vivo efficacy. A series of sensor kinase inhibitors identified by Hoch et al. (1998) included the established antihelminthic compound Closantel and RWJ-49815, which turned out to be molecules leading to non-specific aggregation of sensor kinase molecules in an in vitro assay rather than causing inhibition of phosphorylation reaction (Stephenson et al., 2000). A series of bisphenol analogs identified at Parke-Davis Pharma inhibited NRII autophosphorylation and showed inhibition of functional responses mediated by the two-component system NRII/NRI etc. in whole cell assays (Domagala et al., 1998) and were bactericidal in action at higher concentrations as well. But, the mechanism of cell death was shown to be membrane-disruption leading to complete shutdown of macromolecular synthesis. The compounds are also ineffective in vivo due to excessive plasma protein binding. Thus far, all identified inhibitors of autophosphorylation of histidine sensor kinases have turned out to be hydrophobic compounds that were often difficult to formulate adequately for in vivo protection studies. Whenever tested, these compounds failed to protect in mouse models of infection probably due to excessive serum protein binding.

Halophenylisothiazolones were shown to inhibit the transfer the phosphate from the histidine protein kinase to the response regulator in a reconstituted VanS/VanR signal transduction pathway employing a membrane preparation of the VanS kinase and purified VanR (Ulijasz and Weisblum, 1999). Mechanistic studies demonstrated that the compounds inhibited the acceptor activity of VanR rather than the donor activity of VanS~P. Since inhibition occurred at higher concentration of inhibitor (ED50=0.35 mM), this may account for the discrepancy in the reported mechanism of action. However, isothiozolone derivatives had already shown their inefficacies in in vivo studies as mentioned above.

Imidazolium compounds was reported to inhibit the binding of AlgR1 response regulator to an algD upstream region/probe at a concentration of ~150 µM in a gel-mobility shift assay (Roychoudhary et al., 1993). The compound was claimed to be a specific inhibitor of transcription from the algD promoter as opposed to a non-specific inhibitor of DNA-protein interaction, due to lack of activity on CatR binding to the catBC box. However, as mentioned above the imidazolium derivatives and analogs clearly have a general effect on histidine protein kinase autophosphorylation as well and are quite ineffective in in vivo protection assays.

In general, most of these agents appear to suffer from poor selectivity, excessive protein binding or limited bioavailability.

As mentioned above there is an urgent need to identify novel drug targets for the development of new drugs that would be effective against tuberculosis that is resistant to treatment by drugs that are in use today. Furthermore there is a grave need for effective drugs that can target chronic/latent forms of tuberculosis in contrast to the currently administered drugs that target actively replicating bacilli.

Earlier reports from Dr. Jaya S. Tyagi's laboratory have suggested that the devR gene is more likely to be related in chronic infection process and is less relevant to the growth per se in human monocytes or in the early events of infection. It was observed that the mutant strain failed to cause severe progressive disease and pathology under the experimental conditions in guinea pigs as compared to the wild type H37Rv strain (Kapur, V., Ph.D. Thesis, February 2001, Tyagi and Kapur, PCT/IN02/00022).

Since, the DevR protein belongs to the response regulator class of regulatory proteins; it is plausible that it orchestrates the adaptation of tubercle bacilli to the hostile environment of the host. The two-component system's regulatory network functions through a phosphorylation pathway, where DevS histidine sensor kinase (HK) protein senses a environmental cue or stimulus in response to which it undergoes autophosphorylation at a conserved His395 residue. The phosphorylated DevS species then transfers the phosphoryl moiety to the DevR protein via a phosphotransfer event at a conserved Asp54 residue. A likely phosphorylation-induced change in DevR protein structure likely changes its DNA binding ability, leading to modulation in expression of genes under its control. It is known that this two-component system is responsive to hypoxia (Boon et al., 2001; Sherman et al., 2001; Mayuri et al., 2002), a key factor involved in persistence and it is also believed that this system is indeed involved in virulence of tubercle bacilli (Kapur, V., Ph.D. Thesis, February 2001; Tyagi and Kapur, PCT/IN02/00022). It thus provides a novel target for the development of drugs active against the bacilli located in the granulomas. It is believed that disabling the function of a regulatory system such as DevR-DevS and DevR-Rv2027c will lead to the inactivation of bacterial pathway(s) modulated by them in response to hypoxia or other virulence and pathogenesis-associated signals. The present invention provides the protocol and biochemical assays which can be utilized to screen for inhibitor molecules, compounds, agents or drugs against these pathways or systems which lead to functional inactivation of the system (FIG. 1).

In light of the deficiencies of the two-component system inhibitors from corporate compound libraries, alternate strategies can be employed for identification and design of inhibitors against two-component systems. A rational drug-designing and screening approach involving X-ray or NMR structure of the cytosolic domain of the sensor kinase in combination with computer applications for de novo design and screening of inhibitors have been suggested by many groups (Inouye U.S. Pat. No. 6,162,627). Furthermore, instead of screening inhibitors for phosphorylation reactions, inhibitors can be screened to the other sites in the two-component system pathway, for example, (i) dimerization domain of the sensor kinase, (ii) sensory domain to the sensor kinase, (iii) sensor kinase and response regulator interaction interface, and (iv) response regulator—DNA interaction interface, which is possible only with the detailed understanding of the catalytic activities of the respective participating proteins, which forms an essential part of this invention.

Besides using these modified selections or screening strategies, natural product or combinatorial peptide libraries can also be used as a source of novel two-component system inhibitors in high-throughput assays. Once a lead 'candidate' molecule is identified in high-throughput screening, it should be extendable to screening in whole cell assays also in high throughput assay format.

Though, the DevR-DevS and/or Rv2027c-DevR two-component systems offers unique regulatory systems as targets for developing novel anti-microbial/anti-bacterial/anti-tubercular compounds, the utilization of novel refolding screen and specific mutant proteins also offers a means for effectively screening potent inhibitors via the rational drug design approach using the DevR modeled structure or by using the mutant proteins in screening steps for peptide library screening setup.

The present invention involves utilization of DevR-DevS (Rv3133c-Rv3132c) and Rv2027c-DevR signal transduction pathways as targets for therapy against diseases caused by mycobacterial organisms including all forms of *Mycobacterium tuberculosis* and other mycobacteria possessing these two-component systems. The invention further covers the utilization of these proteins and their catalytic activities as modes for screening antibacterial, antimycobacterial, bactericidal and/or bacteriostatic drugs and/or compounds that target all or any steps of these signal transduction pathways.

Rv2027c protein is 62.5% identical to DevS protein and contains H, N, D/G1 and G2 boxes typical of histidine kinases. It was speculated that Rv2027c being an orphan sensor kinase, could be autophosphorylated and in turn participate in an phosphotransfer event with DevR protein. As described herein this hypothesis was tested and confirmed to occur in vitro.

It is hence proposed to use these phosphorylation assays or reactions to screen for lead molecules that block these phosphorylation reactions and utilize them as bactericidal/antimicrobial compounds capable of interfering with these signal transduction pathways and thereby inhibiting the expression of downstream gene targets under their control and blocking their physiological manifestations such as, for example, dormancy or latency (see FIG. 1).

SUMMARY OF THE PRESENT INVENTION

The present invention relates to screening methods designed for developing drugs against pathogenic microbes having two-component system of DevR-DevS and/or DevR-Rv2027c and its homologues, and a method of treatment.

The present invention provides a package of screening methods for developing drugs against pathogenic microbes having two-component system of DevR-DevS and/or DevR-Rv2027c and its homologues.

Another object of the present invention is to develop a method of screening for developing drugs showing activity selected from a group comprising antibiotic activity, antibacterial activity, anti-microbial activity and anti-tubercular.

Yet another object of the present invention is to develop a method to help identify anti-tuberculosis drugs, anti-mycobacterial drugs and drugs against disease conditions caused by bacteria such as pneumonia, pertussis, listeriosis, enterobacterial diseases, cholera, etc.

Another object of the present invention is to develop a method of treating disease conditions caused by pathogenic microbes having two-component system of DevR-DevS and/or DevR-2027c or homologues.

Yet another object of the present invention is to develop a composition useful in the management disease conditions caused by pathogenic microbes having two-component system of DevR-DevS and/or DevR-2027c or homologues said composition comprising a drug selected from a group consisting of Ethidium Bromide (EtBr), Bromo Phenol Blue (BPB), 2-mercapto benzimidazole (2-MBI), and 2-phenyl-benzimidazole and active derivatives thereof, and a pharmaceutically acceptable additive.

Autophosphorylation of histidine sensor kinases. 3. Phosphorylation of DevR response regulator protein by phosphorylated sensor kinases. 4. Binding of DevR to its specific DNA-targets. Assays for steps 2 and 3 are covered in this patent application. Transmembrane helices in DevS and Rv2027c were predicted by TMpred analysis at www.expasy.org. These proteins are therefore depicted to have a membrane association as per the predictions.

Figure 2:
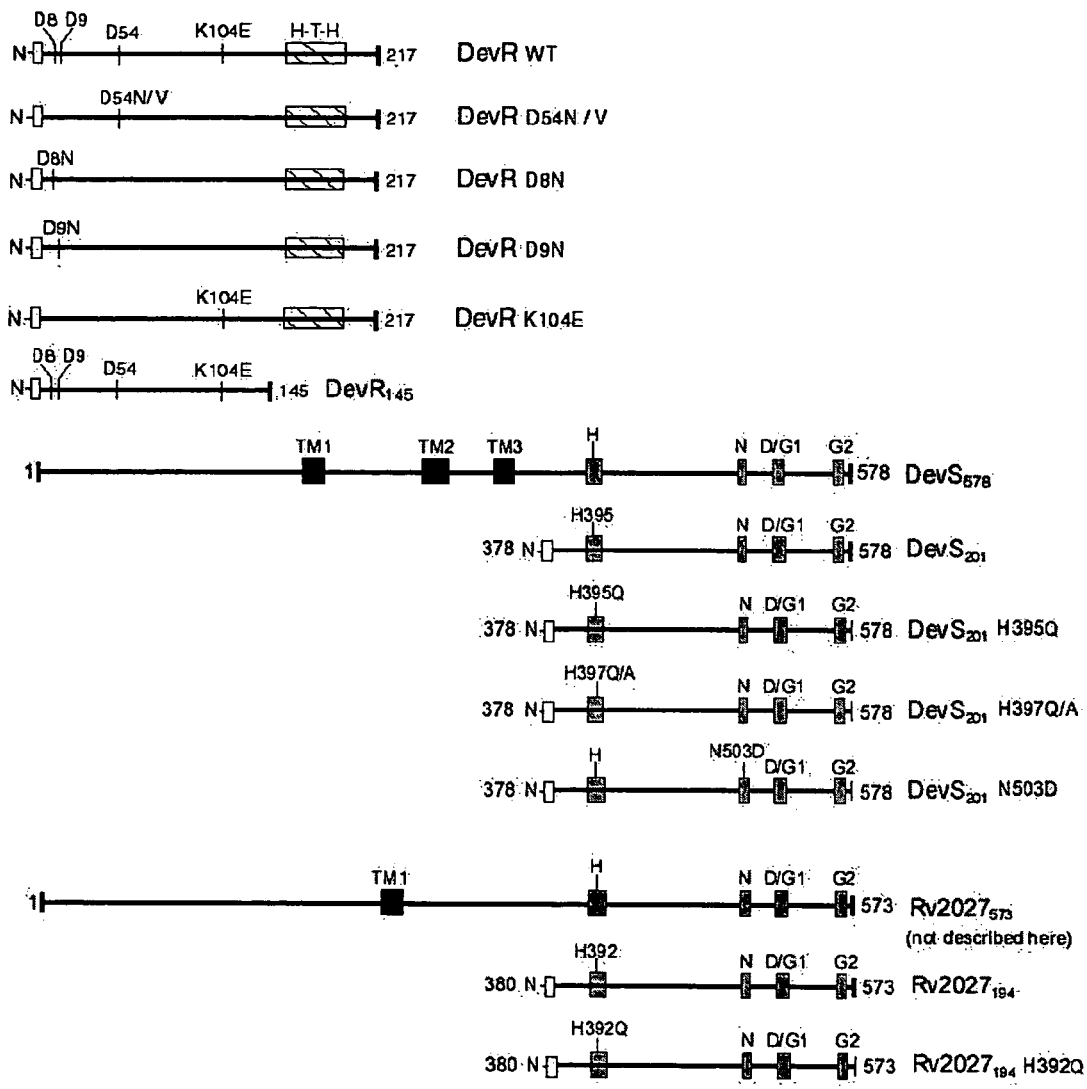

FIG. 2. Features of DevR, DevRN$_{145}$, DevS and Rv2027c proteins of *M. tuberculosis* and amino acid substitutions in mutant proteins. The white box at the N-terminus of the overexpressed protein represents the His$_6$-tag, H-T-H represents the helix-turn-helix motif present in the C-terminal domain of DevR as predicted by Interpro scan (www.expasy.org). TM 1, 2 and 3 refer to transmembrane domains predicted by TMpred (www.expasy.org). The shaded boxes H, N, D/G1 and G2 indicate the conserved sequence motifs present in sensor histidine kinases. Numbers 8, 9 etc. represent the amino acid number of the respective proteins. DevRN$_{145}$ refers to the 145 amino acids long catalytically-active N-terminal region of DevR response regulator. DevS$_{201}$ refers to the 201 amino acids long catalytically-active cytosolic region of DevS sensor kinase. DevS$_{578}$ refers to the 578 amino acids long full-length DevS sensor kinase. Rv2027$_{194}$ refers to the 194 amino acids long catalytically-active cytosolic region of Rv2027c sensor kinase. The subscripts refer to the number of amino acid residues of *M. tuberculosis* origin in the recombinant plasmid.

Figure 3:
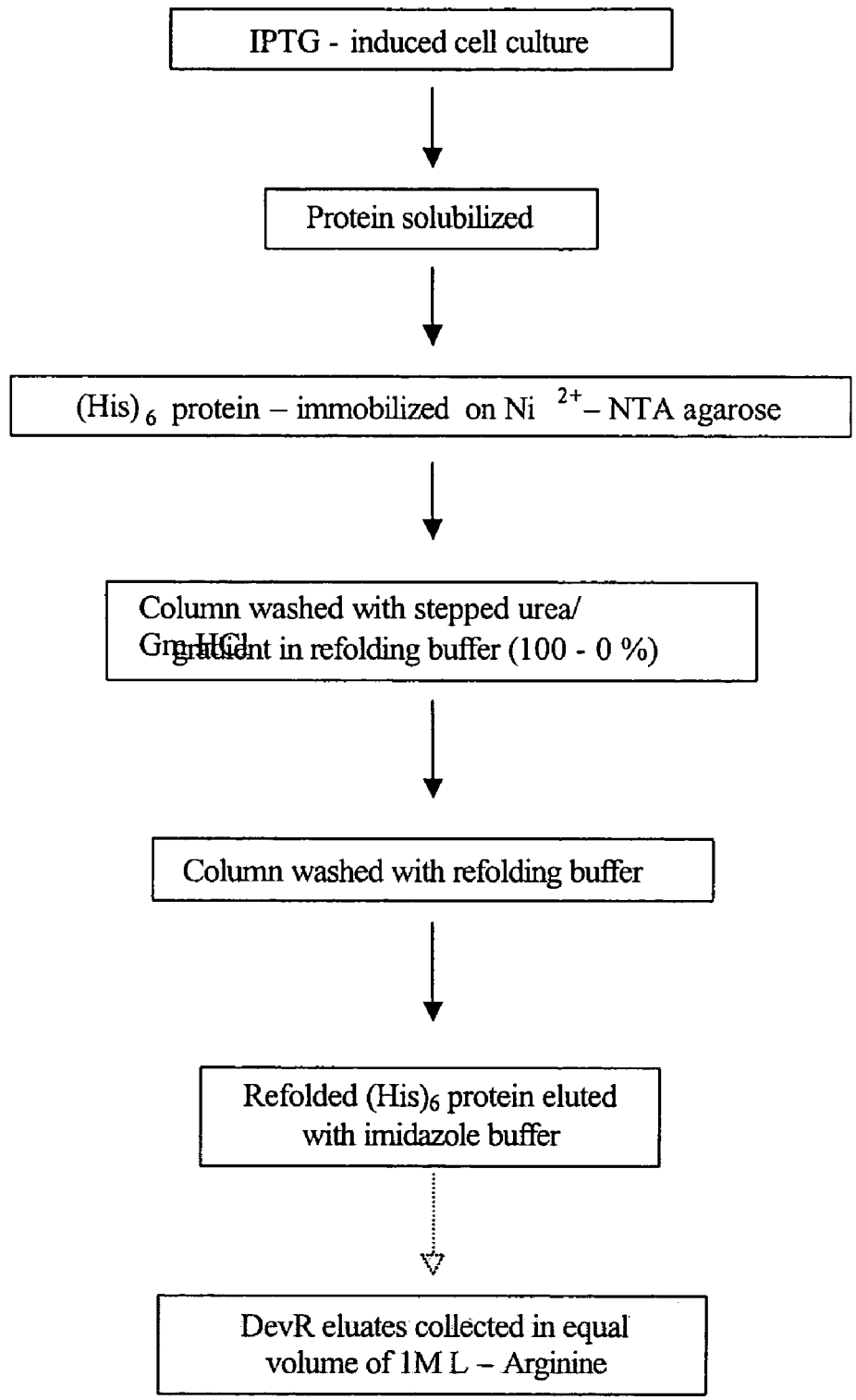

FIG. 3. Flow chart of matrix-assisted purification and redox-based refolding of His$_6$ tagged fusion proteins used in the study.

Figure 4:
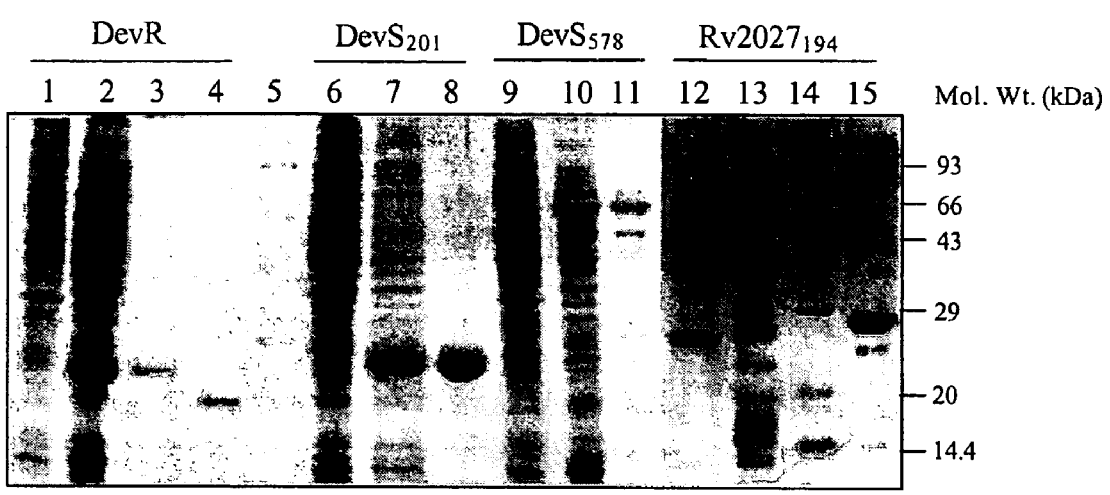

FIG. 4. SDS-PAGE analysis of proteins overexpressed in *E. coli*. Lanes 1, 6, 9 and 12, uninduced *E. coli* lysate of cells carrying recombinant DevR, DevS$_{201}$, DevS$_{578}$ and Rv2027$_{194}$ expression constructs; lanes 2, 7, 10 and 13, induced *E. coli* lysate; lanes 3, 4, 8, 11 and 15, Purified proteins DevR, DevRN$_{145}$, DevS$_{201}$, DevS$_{578}$ and Rv2027$_{194}$ and lane 5 and 14, protein molecular weight marker.

Figure 5:
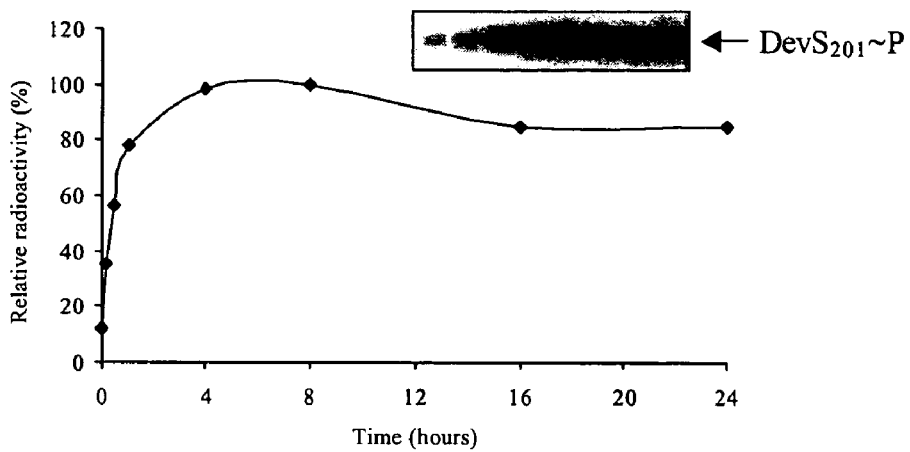
Figure 5:
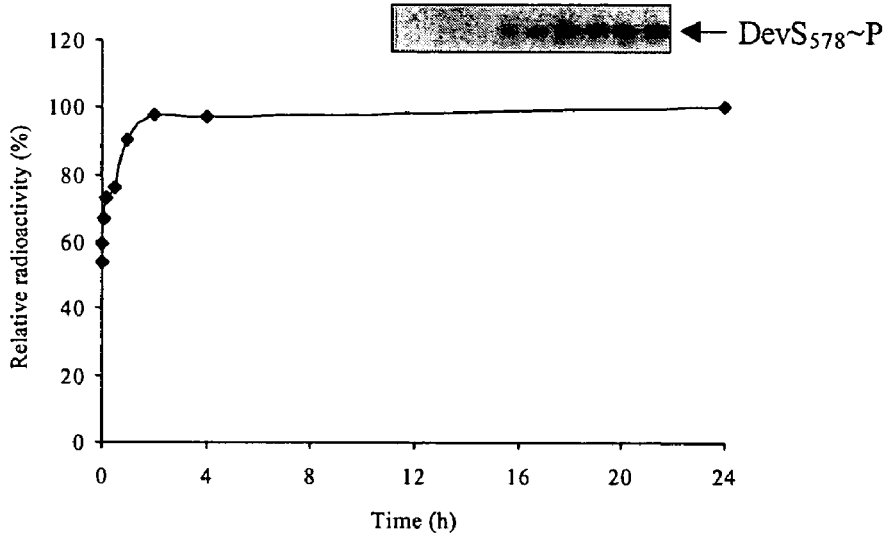
Figure 5:
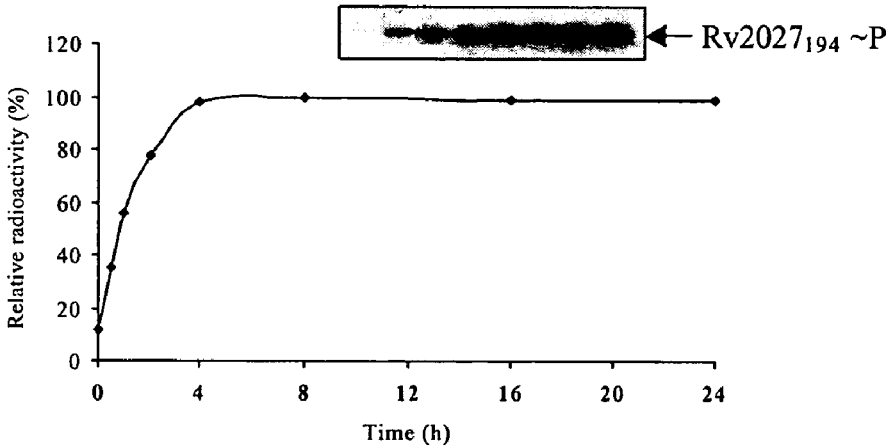

FIG. 5. Time dependent autophosphorylation of sensor kinase proteins. DevS$_{201}$ and Rv2027$_{194}$ with [γ$^{32}$P]ATP. Purified proteins (15 μM each of DevS$_{201}$ or Rv2027$_{194}$ or 5 μM of DevS$_{578}$) was incubated in reaction buffer as described and samples were removed at indicated time points (in hrs.), chilled on ice with stop buffer and analyzed by SDS-PAGE. Gel slices corresponding to the labeled proteins were excised and incorporation was quantitated by liquid-scintillation counting. Representative profiles of A. DevS$_{201}$ B. DevS$_{578}$ C. Rv2027$_{194}$ autophosphorylation reactions.

Figure 6:
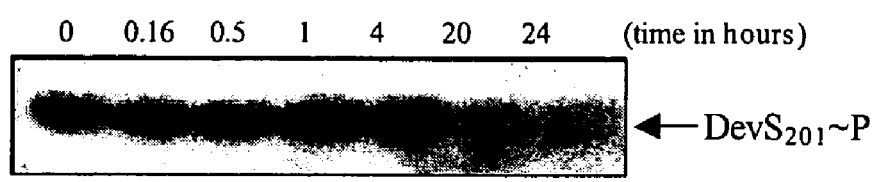
Figure 6:
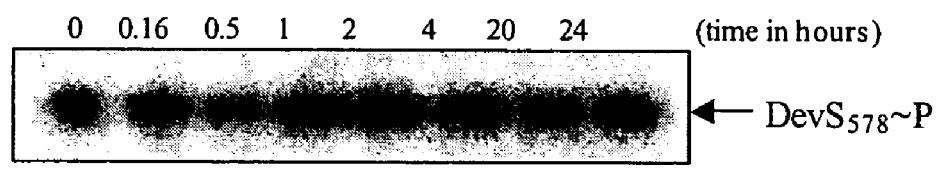
Figure 6:
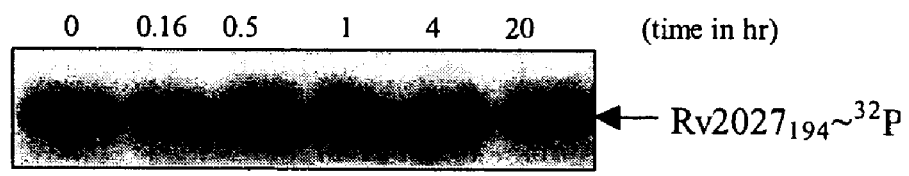

FIG. 6. A. Stability of DevS$_{201}$~$^{32}$P. DevS$_{201}$~$^{32}$P was prepared as described and its stability was analyzed by incubation at 25° C. for various time points as indicated after removal of unincorporated [γ$^{32}$P]ATP by filtration of the reaction mixture through a 10 kDa MWCO Nanosep device. B. Stability of DevS$_{578}$~$^{32}$P. DevS$_{578}$~$^{32}$P was prepared as described and its stability was analyzed essentially as performed for DevS$_{201}$. C. Stability of Rv2027$_{194}$~$^{32}$P. The reaction was essentially done as for DevS$_{201}$ (see above).

Figure 7:
Figure 7:
Figure 7:
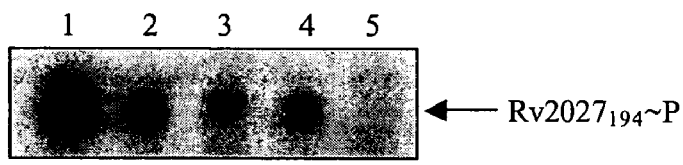

FIG. 7. Ionic requirement for autophosphorylation reaction. A. DevS$_{201}$ (15 μM) was autophosphorylated with [γ$^{32}$P] ATP in reaction buffer containing specific divalent cations as mentioned. Lane 1, MgCl$_2$; lane 2, MnCl$_2$, lane 3, CaCl$_2$; lane 4, CoCl$_2$; lane 5, EDTA; lane 6, MgSO$_4$; lane 7, NiSO$_4$; lane 8, CuSO$_4$ and lane 9, ZnSO$_4$, 25 mM each. B. DevS$_{578}$ (5 μM) was autophosphorylated with [γ$^{32}$P]ATP in reaction buffer containing specific divalent cations as mentioned. Lane 1, MnCl$_2$; lane 2, MgCl$_2$, lane 3, CaCl$_2$; lane 4, CoCl$_2$; lane 5, EDTA; lane 6, MgSO$_4$; lane 7, NiSO$_4$; lane 8, CuSO$_4$; lane 9, ZnSO$_4$ and lane 10, HgSO$_4$, 25 mM each. C. Rv2027$_{194}$ (15 μM) was autophosphorylated with [γ$^{32}$P]ATP in reaction buffer containing specific divalent cations as mentioned. Lane 1, MgCl$_2$; lane 2, MnCl$_2$, lane 3, CaCl$_2$; lane 4, CoCl$_2$; lane 5, EDTA, 25 mM each.

Figure 8:
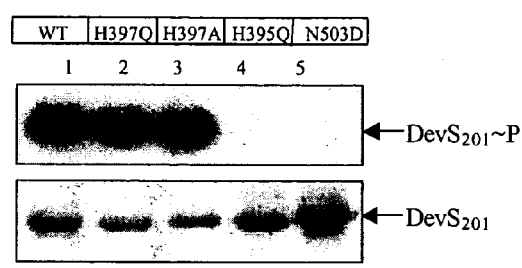
Figure 8:
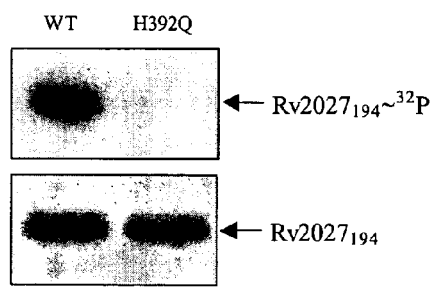
Figure 8:
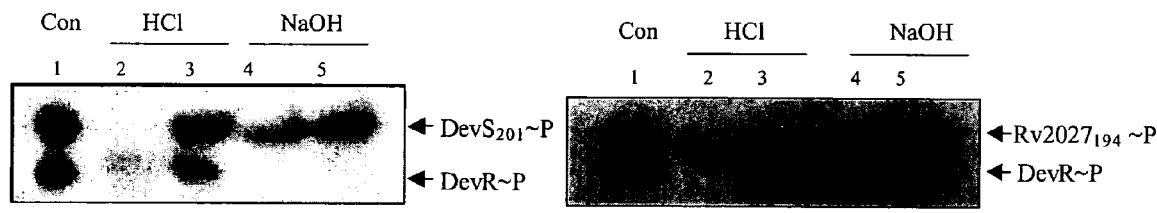

FIG. 8. A. Phosphorylation reaction with DevS$_{201}$ mutant proteins. DevS$_{201}$ protein and its mutants were phosphorylated as described. The lower panel shows the Coomassie stained pattern of the SDS-PAGE profile of the above. B. Phosphorylation reaction with Rv2027$_{194}$ mutant protein. Rv2027$_{194}$ protein and its mutant were phosphorylated as described. The lower panel shows the Coomassie stained pattern of the SDS-PAGE profile of the above. C. Chemical stability DevS$_{201}$~$^{32}$P, Rv2027$_{194}$~$^{32}$P and DevR~$^{32}$P. DevS$_{201}$~$^{32}$P, Rv2027$_{194}$~$^{32}$P and DevR~$^{32}$P were prepared as described. The products were stabilized with 2% SDS, test reagents were added and tubes incubated at 37° C. for 30 min. Samples were analyzed by SDS-PAGE after neutralization with Tris. Lane 1, control containing 2% SDS alone; lane 2, plus 1 N HCl; lane 3, plus 0.1N HCl; lane 4, plus 1N NaOH and lane 5, plus 0.1N NaOH.

Figure 9:
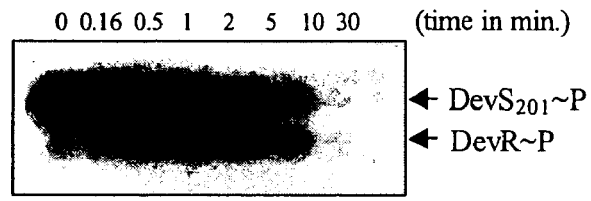
Figure 9:
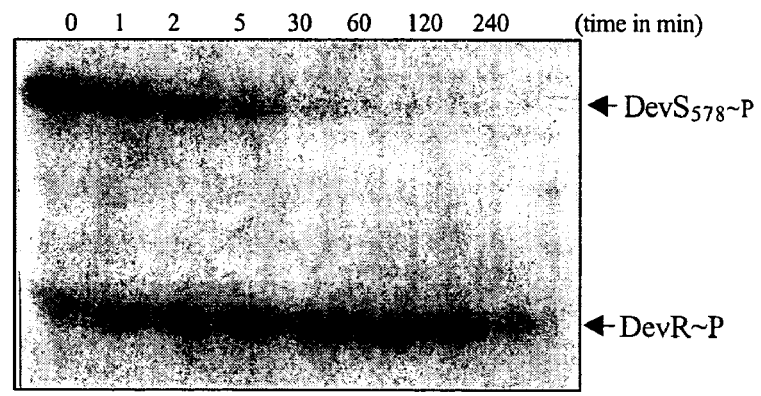
Figure 9:
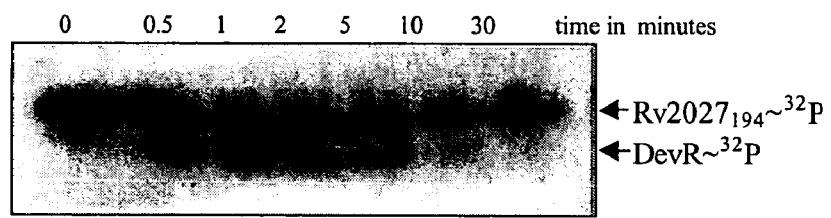
Figure 9:
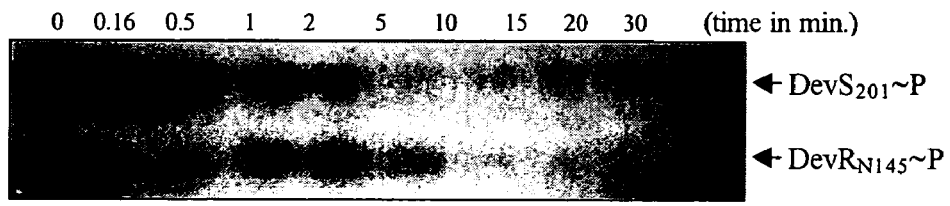
Figure 9:
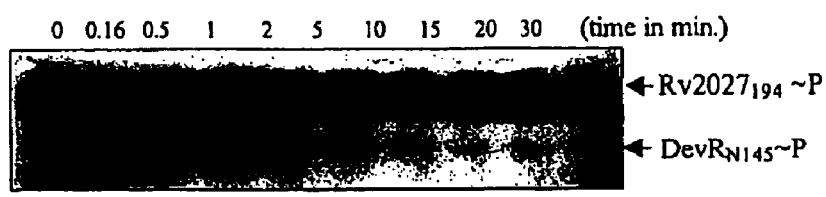
Figure 9:
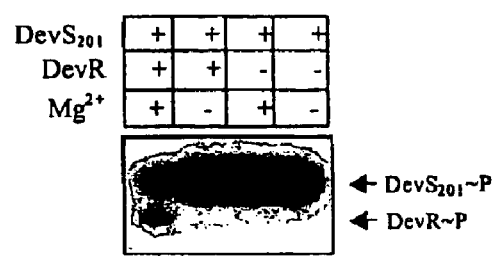

FIG. 9. A. Phosphotransfer from DevS$_{201}$~$^{32}$P to DevR. DevS$_{201}$~$^{32}$P was prepared as described, DevR was added to DevS$_{201}$~$^{32}$P in a molar ratio of 3:4 DevS$_{201}$: DevR respectively and the tubes were incubated at 25° C. Samples were collected as indicated, mixed with stop buffer and analyzed by SDS-PAGE. B. Phosphotransfer from DevS$_{578}$~$^{32}$P to DevR. DevS$_{578}$~$^{32}$P was prepared as described, DevR was added to DevS$_{578}$~$^{32}$P in a molar ratio of 1:4 DevS$_{578}$: DevR respectively and the tubes were incubated at 25° C. Samples were collected as indicated, mixed with stop buffer and analyzed by SDS-PAGE. C. Phosphotransfer from Rv2027$_{194}$~$^{32}$P to DevR. Rv2027$_{194}$~$^{32}$P was prepared as described, DevR was added to Rv2027$_{194}$~$^{32}$P in a molar ratio of 3:4 Rv2027$_{194}$: DevR respectively and the tubes were incubated at 25° C. Samples were collected as indicated, mixed with stop buffer and analyzed by SDS-PAGE. D. Phosphotransfer from DevS$_{201}$~$^{32}$P to DevRN$_{145}$. DevS$_{201}$~$^{32}$P was prepared as described, DevRN$_{145}$ was added to DevS$_{201}$~$^{32}$P in a molar ratio of 3:4 DevS$_{201}$: DevRN$_{145}$ respectively and the tubes were incubated at 25° C. Samples were collected as indicated, mixed with stop buffer and analyzed by SDS-PAGE. E. Phosphotransfer from Rv2027$_{194}$~$^{32}$P to DevRN$_{145}$. Rv2027$_{194}$~$^{32}$P was prepared as described, DevRN$_{145}$ was added to Rv2027$_{194}$~$^{32}$P in a molar ratio of 3:4 Rv2027$_{194}$: DevRN$_{145}$ respectively and the tubes were incubated at 25° C. Samples were collected as indicated, mixed with stop buffer and analyzed by SDS-PAGE. F. Mg2+-dependent phosphotransfer from DevS$_{201}$~$^{32}$P to DevR. DevS$_{201}$~$^{32}$P was prepared as described, filtered through a 10 k Nanosep device and washed to remove MgCl$_2$ and ATP. DevR (20 μM) and Mg$^{2+}$ were added as indicated and the tubes incubated for 3 min.

Figure 10:
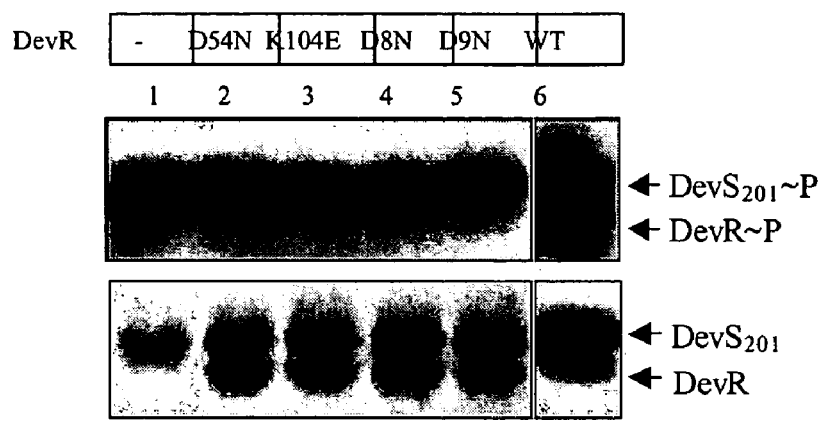
Figure 10:
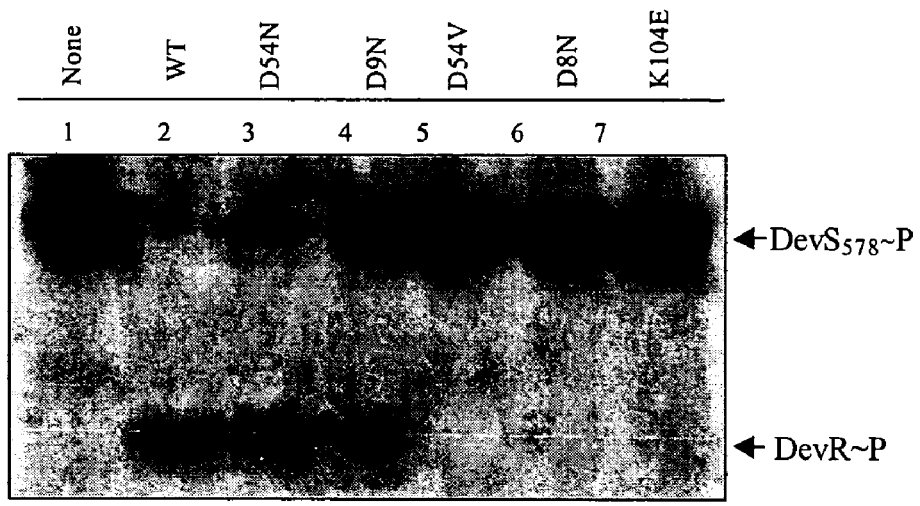

FIG. 10. A. Phosphotransfer reaction between DevS$_{201}$ and DevR mutant proteins. DevS$_{201}$~$^{32}$P was prepared as described and incubated with different mutants for 3 min and analyzed. Lane 1, DevS$_{201}$~$^{32}$P alone; lane 2, DevR-D54V; lane 3, DevR-K104E; lane 4, DevR-D8N; lane 5, DevR-D9N; lane 6, wild type DevR. The lower panel shows the Coomassie stained pattern of the SDS-PAGE profile of the above. B. Phosphotransfer reaction between DevS$_{578}$ and DevR mutant proteins. DevS$_{578}$~$^{32}$P was prepared as described and was incubated with various mutant DevR proteins for 3 minutes at 25° C. The samples were then analyzed by SDS-PAGE after termination with stop buffer. Lane 1, No DevR; lane 2, wild type DevR; lane 3, DevR-D54N; lane 4, DevR-D9N; lane 5, DevR-D54V; lane 6, DevR-D8N and 7, DevR-K104E.

Figure 11:
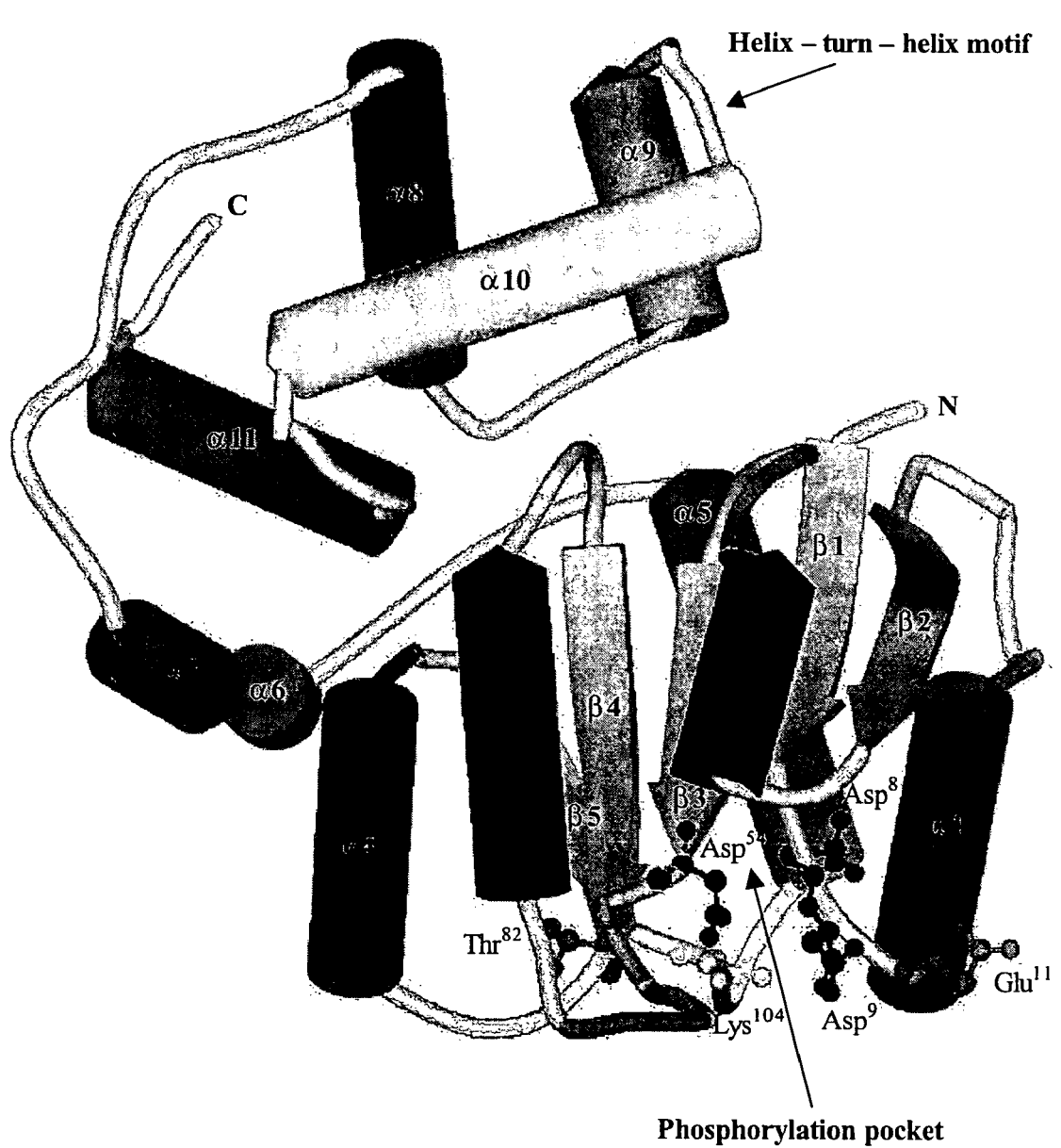

FIG. 11. Predicted 3-D structure of DevR protein of *M. tuberculosis*. The 3D-structure of DevR was modeled using "Swiss-Model" software available at public domain server www.expasy.ch on the structure template and coordinates of response regulator protein NarL from *E. coli* (Baikalov et al., 1996) (PDB accession no. 1A04). Asp$^{54}$, the phosphorylation residue, Asp$^8$ and Asp$^9$, the divalent cation binding residues, Glu$^{11}$, the neighboring acidic residue (implicated in binding Mg$^{+2}$ in case of mutation in Asp$^9$), the conserved Thr$^{82}$ purple and the invariant Lys$^{104}$, are represented in ball and stick form. The two α-helices (α9 and α10) comprising the H-T-H motif are also indicated.

Figure 12:
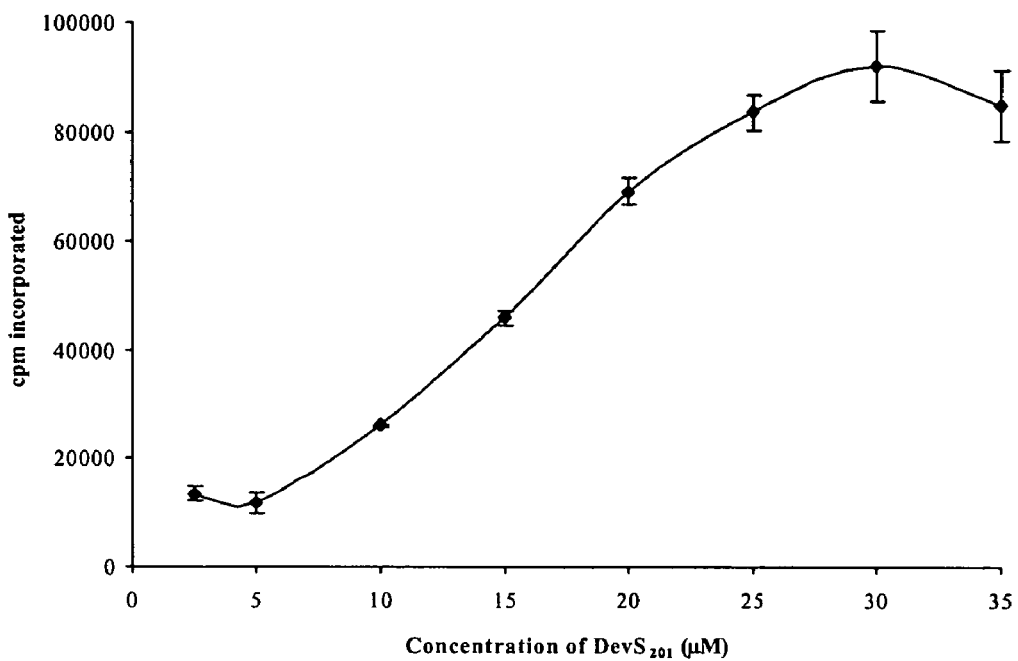
Figure 12:
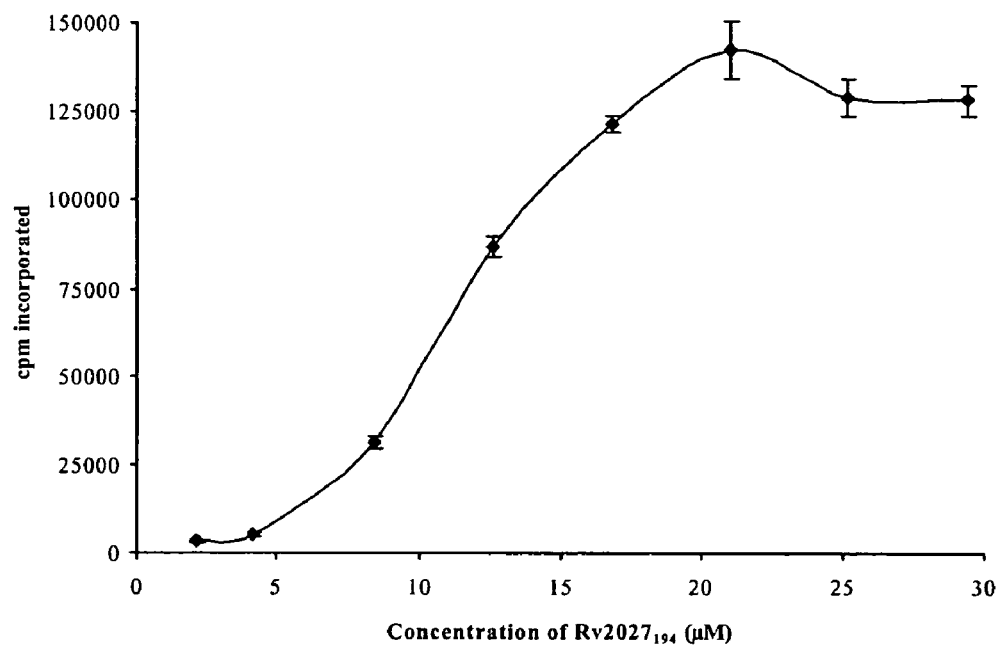

FIG. 12. Optimal concentration of the sensor kinases for the autophosphorylation reaction in high-throughput assays. A. DevS$_{201}$ and B. Rv2027$_{194}$. The reaction was performed essentially as disclosed in the detailed description. Various amounts of the respective proteins were phosphorylated in 10 µl reaction volume, filtered and washed as mentioned and the Cpm±SD retained is plotted as a function of protein concentration. Each experiment was performed in triplicate.

Figure 13:
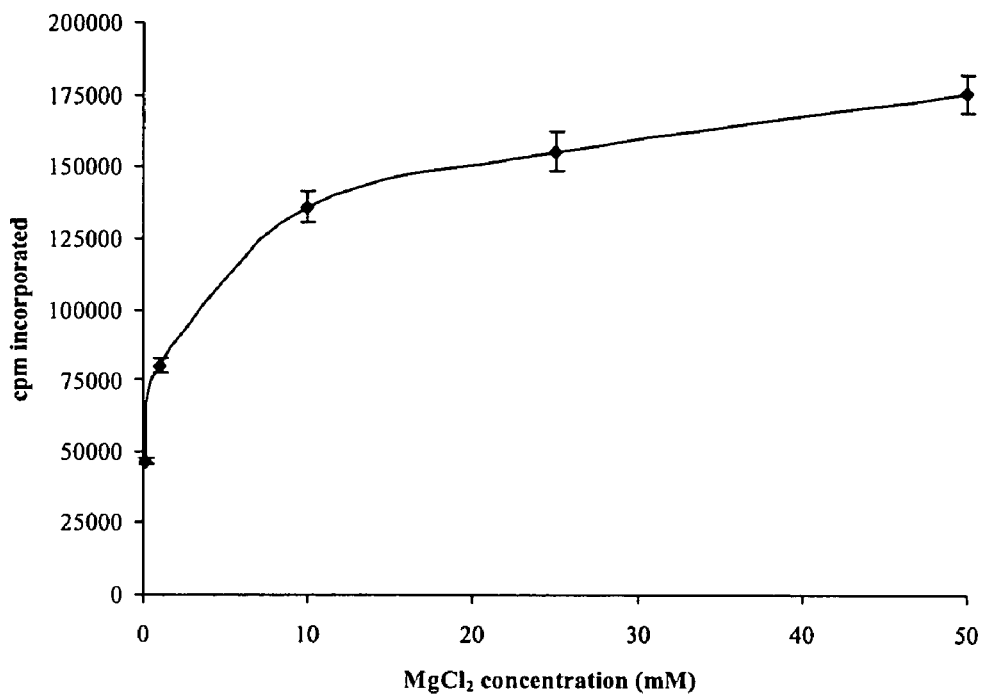
Figure 13:
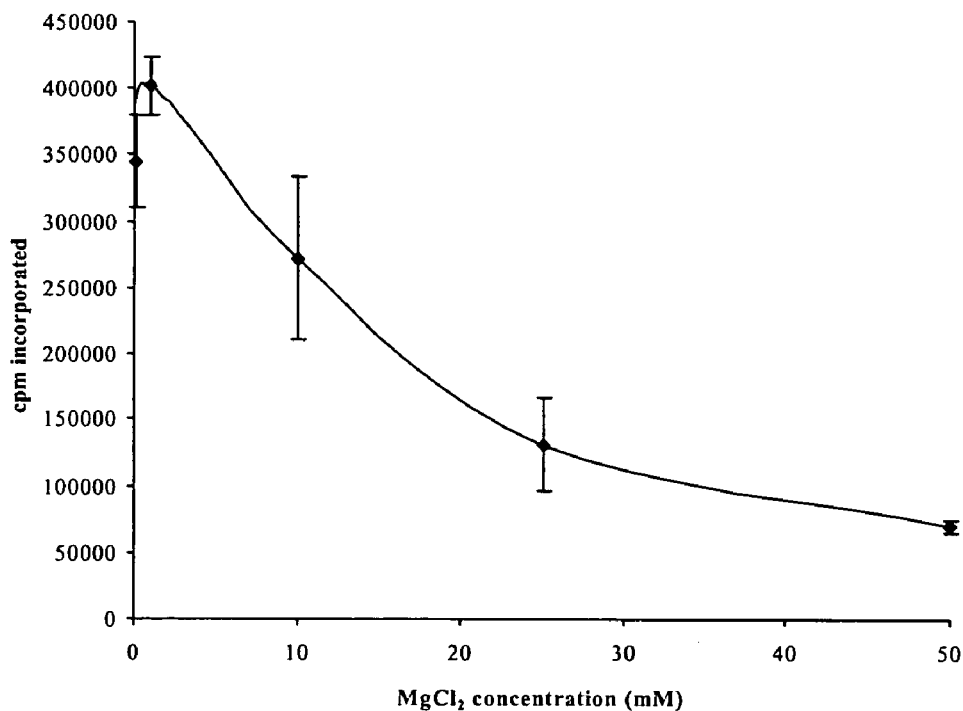

FIG. 13. Optimal concentration of MgCl$_2$ required for autophosphorylation reaction of sensor kinases in high-throughput assays. A. DevS$_{201}$ and B. Rv2027$_{194}$. The reaction was performed essentially as disclosed in the detailed description. Various amounts of the MgCl$_2$ was added to the reaction mix containing optimum concentration of the individual proteins; (30 µM of DevS$_{201}$ and 21 µM of Rv2027$_{194}$ proteins) and phosphorylated in 10 µl reaction volume, filtered and washed as mentioned and the Cpm±SD retained is plotted as a function of MgCl$_2$ concentration. Each experiment was performed in triplicate.

Figure 14:
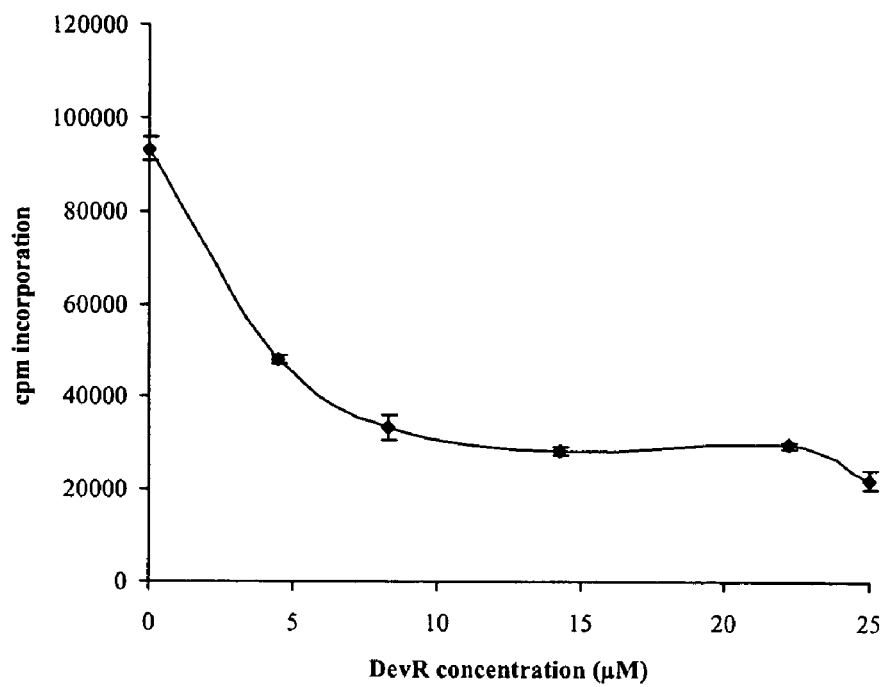
Figure 14:
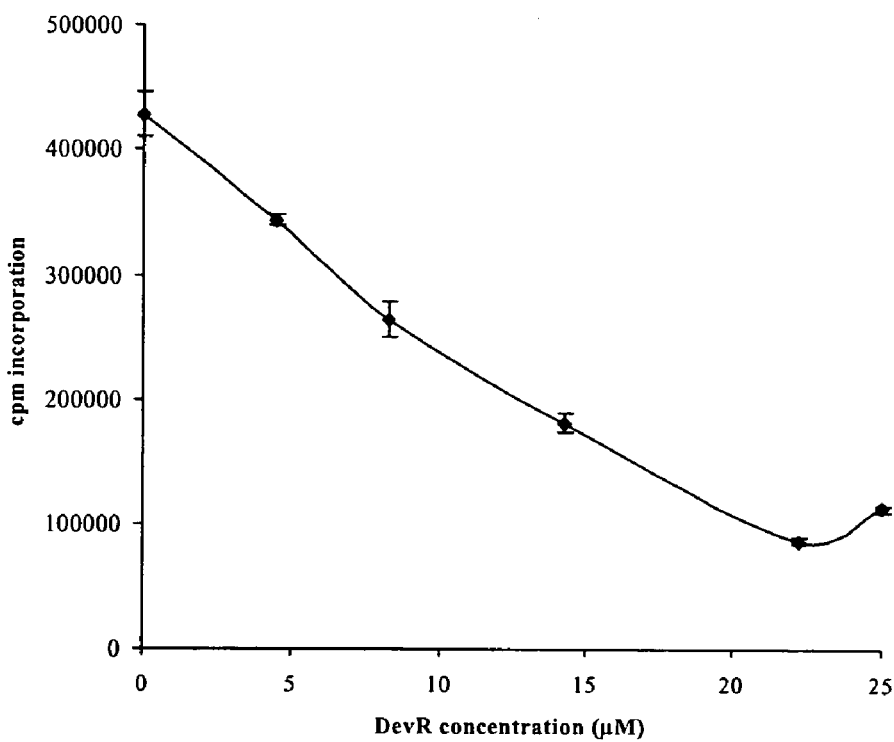

FIG. 14. Optimal DevR concentration for dephosphorylation of sensor kinase/s in high-throughput assays. Phosphotransfer through A. DevS$_{201}$ and B. Rv2027$_{194}$. Autophosphorylation of sensor kinase/s was performed as mentioned above. For this, 30 µM of DevS$_{201}$ and 21 µM of Rv2027$_{194}$ proteins were phosphorylated in 10 µl reaction volume with 25 mM and 1 mM MgCl$_2$ respectively (optimum concentrations) for 60 minutes. Subsequently, various amounts of DevR protein (as indicated) was added to the autophosphorylation reaction mix and incubated at 25° C. for 20 minutes. After which the reaction contents were filtered and washed as mentioned and the Cpm±SD retained is plotted as a function of DevR concentration. Each experiment was performed in triplicate.

Figure 15:
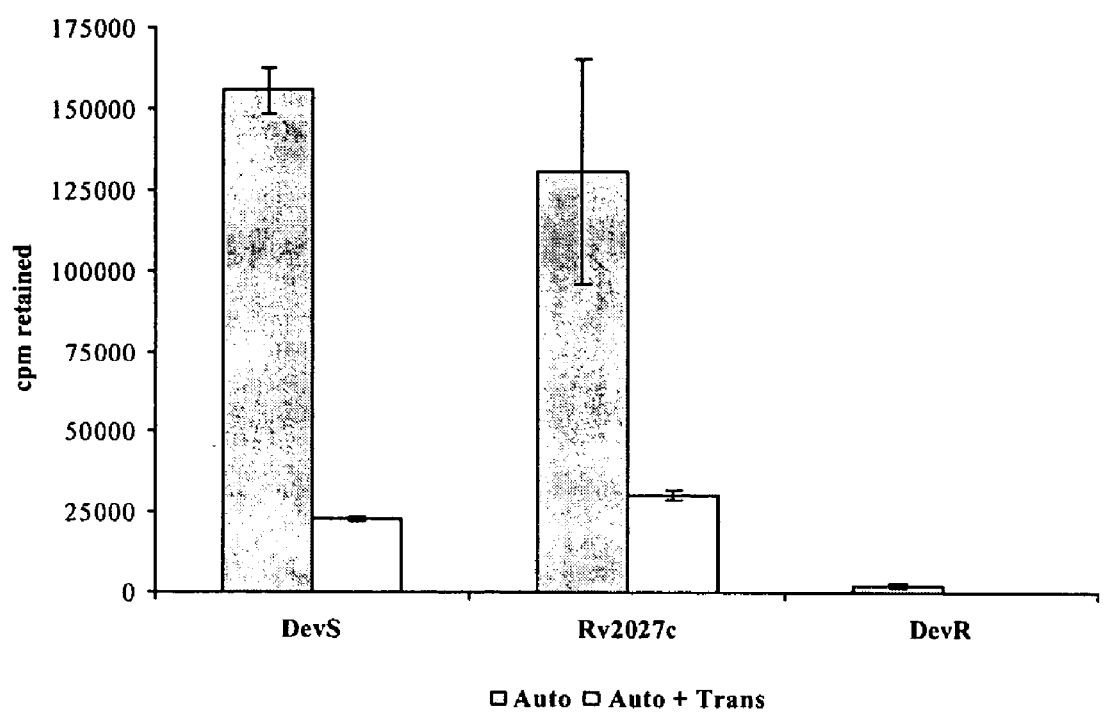

FIG. 15. Dephosphorylation of sensor kinases as an outcome of phosphotransfer reaction to response regulator protein DevR in high-throughput assays. The reaction was performed essentially as disclosed in the detailed description. DevR (16 µM) was added to the reaction mix containing phosphorylated forms of 30 µM of DevS$_{201}$ and 21 µM of Rv2027$_{194}$ proteins 10 µl reaction volume containing 25 mM MgCl$_2$ and the final reaction contents were incubated at room temperature for an additional 20 minutes to facilitate the phosphotransfer and subsequent dephosphorylation. Then the contents were filtered and washed as mentioned and the Cpm±SD retained is plotted as a function of nature of phosphorylation reaction (autophosphorylation vs transphosphorylation). Each experiment was performed in triplicate.

Figure 16:
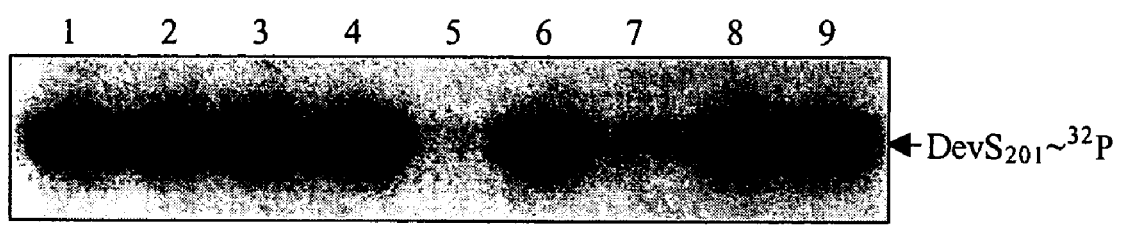

FIG. 16. Inhibition of autophosphorylation of sensor kinase DevS$_{201}$ by various candidate compounds. Autoradiogram of SDS-PAGE of autophosphorylation reaction products. Lane 1, levamisole HCl; lane 2, folic acid; lane 3, gly-gly-glycine; lane 4, EGTA; lane 5, bromo-phenol blue; lane 6, HABA; lane 7, ethidium bromide; lane 8, anti-DevS antibody (1 µl); lane 9, no compound. Briefly, all the mentioned compounds (1 mM final concentration) were added to 12 µM of DevS$_{201}$ in reaction buffer without ATP and incubated at RT for 30 minutes after which the reaction was initiated by addition of [γ$^{32}$P]ATP and cold ATP. The reaction contents were then incubated at 25° C. for 60 minutes and were subsequently analyzed on gel as mentioned earlier.

Figure 17:
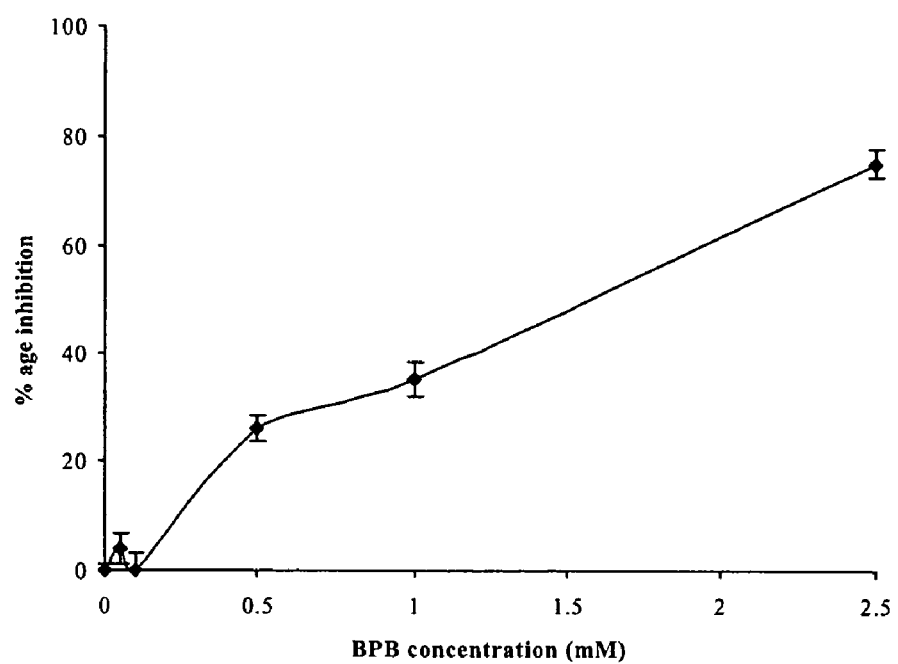
Figure 17:
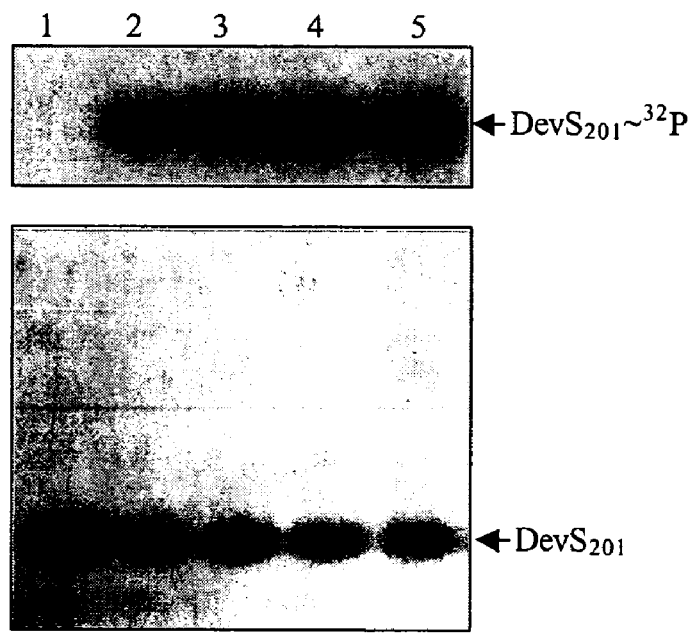
Figure 17:
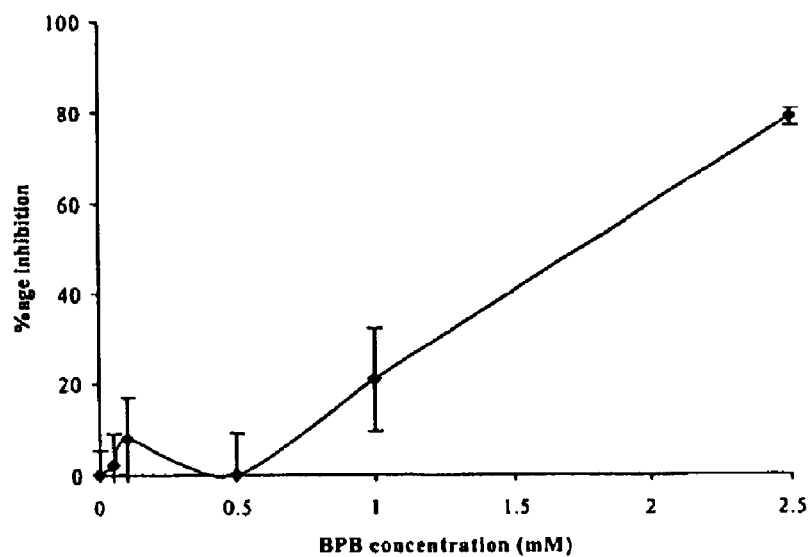
Figure 17:
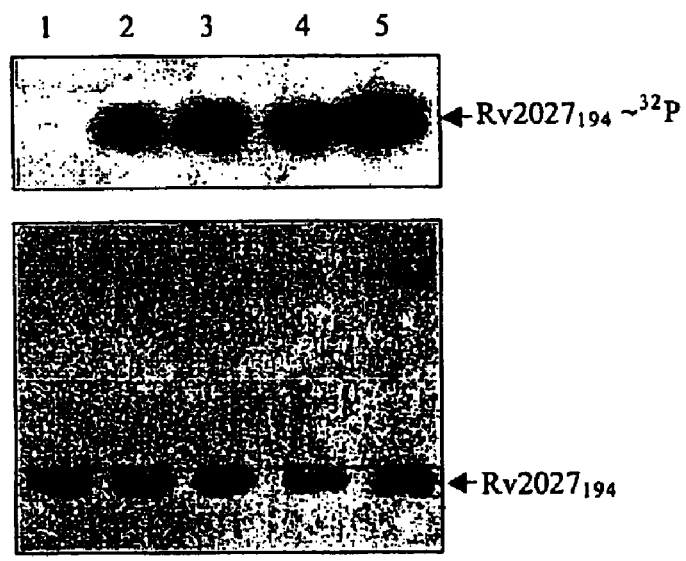

FIG. 17. BPB concentration-dependent inhibition of autophosphorylation of DevS$_{201}$ and Rv2027$_{194}$. The assay was performed in high throughput format in triplicate essentially as described earlier. The Cpm±SD retained is plotted as a function of concentration of BPB in the reaction. A. DevS$_{201}$ inhibition profile B. Autoradiogram of SDS-PAGE profile of DevS$_{201}$ autophosphorylation reaction products. BPB concentration in the reaction lane 1, 1 mM; lane 2, 0.5 mM; lane 3, 0.1 mM; lane 4, 0.01 mM and lane 5, no inhibitor. The lower panel represents the coomassie-stained SDS-PAGE profile, which shows that the addition of BPB did not cause aggregation of sensor kinase. C. Rv2027$_{194}$ inhibition profile D. Autoradiogram of SDS-PAGE profile of Rv2027$_{194}$ autophosphorylation reaction products. BPB concentration in the reaction lane 1, 1 mM; lane 2, 0.5 mM; lane 3, 0.1 mM; lane 4, 0.01 mM and lane 5, no inhibitor. The lower panel represents the coomassie-stained SDS-PAGE profile, which shows that the addition of BPB did not cause aggregation of sensor kinase.

Figure 19:
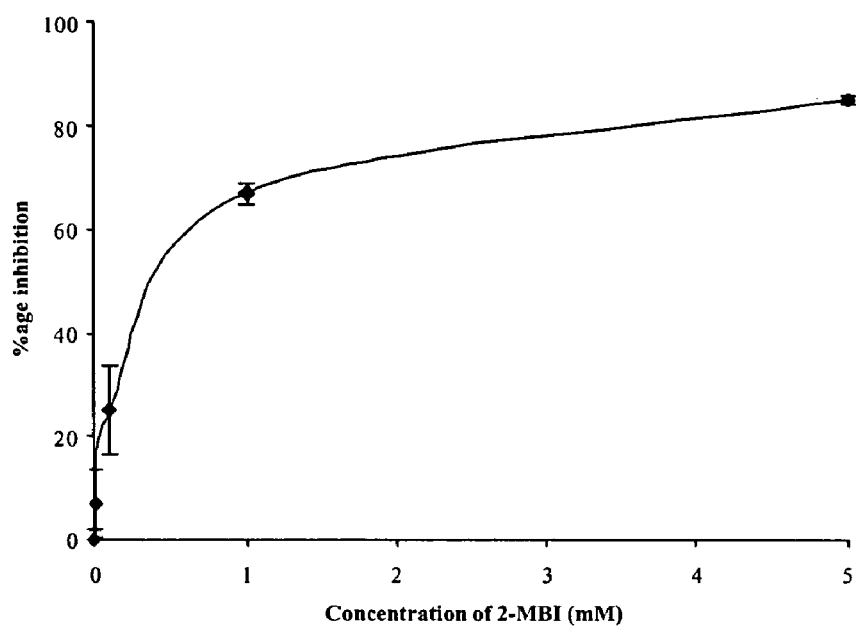
Figure 19:
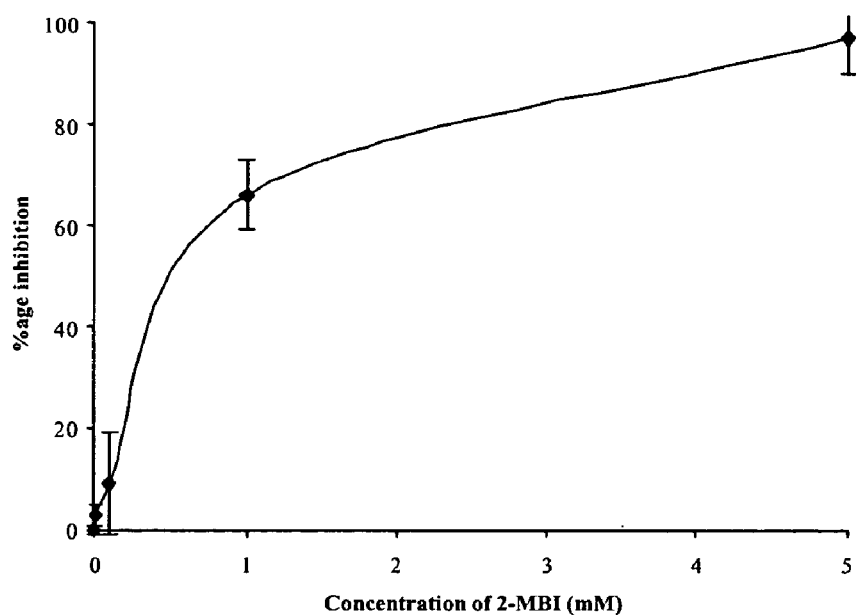

FIG. 19. 2-mercapto benzimidazole (2-MBI) concentration-dependent inhibition of autophosphorylation of DevS$_{201}$ and Rv2027$_{194}$. The assay was performed in high throughput format in triplicate essentially as described earlier. The Cpm±SD retained is plotted as a function of concentration of 2-MBI in the reaction. A. DevS$_{201}$ inhibition profile B. Rv2027$_{194}$ inhibition profile.

Figure 18:
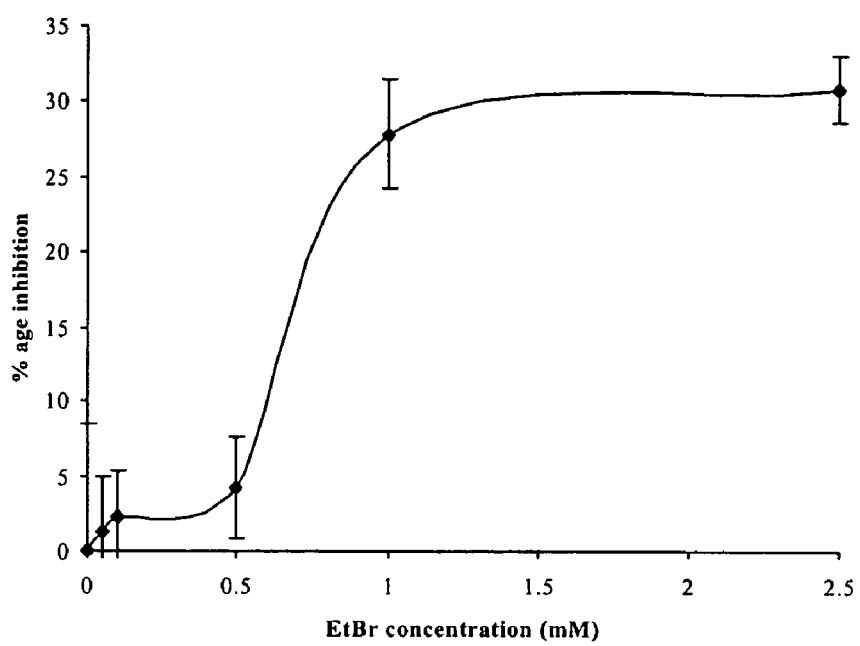
Figure 18:
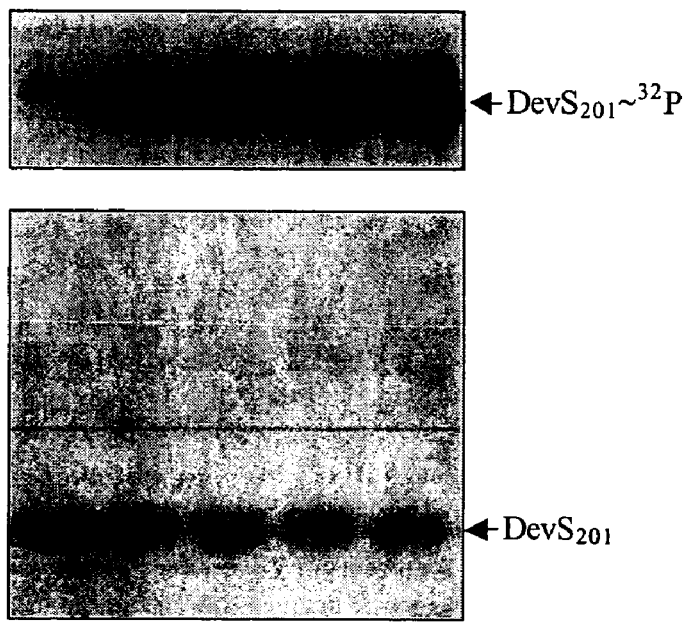
Figure 18:
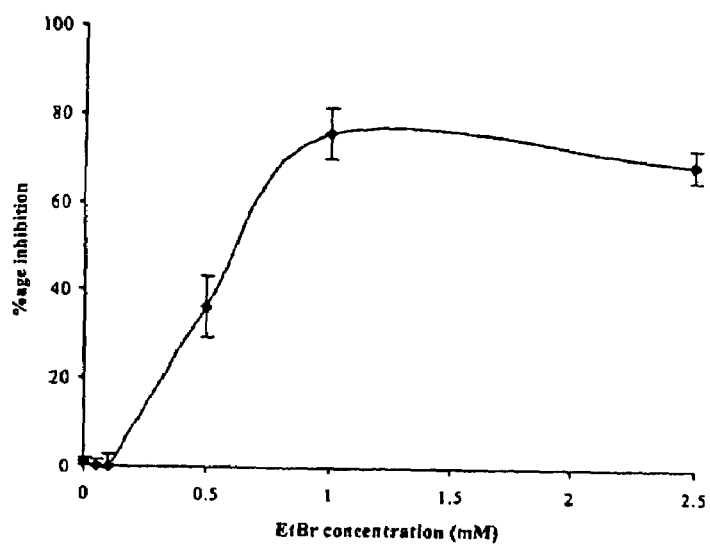
Figure 18:
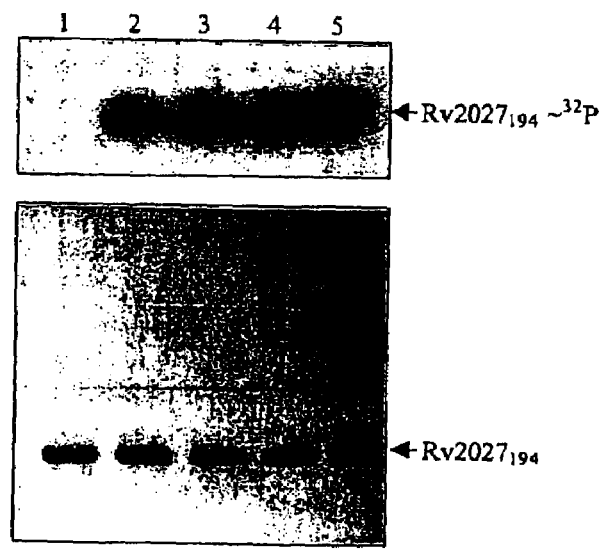

FIG. 18. EtBr concentration-dependent inhibition of autophosphorylation of DevS$_{201}$ and Rv2027$_{194}$. The assay was performed in high throughput format in triplicate essentially as described earlier. The Cpm±SD retained is plotted as a function of concentration of EtBr in the reaction. A. DevS$_{201}$ inhibition profile B. Autoradiogram of SDS-PAGE profile of DevS$_{201}$ autophosphorylation reaction products. EtBr concentration in the reaction lane 1, 1 mM; lane 2, 0.5 mM; lane 3, 0.1 mM; lane 4, 0.01 mM and lane 5, no inhibitor. The lower panel represents the coomassie-stained SDS-PAGE profile, which shows that the addition of EtBr did not cause aggregation of sensor kinase. C. Rv2027$_{194}$ inhibition profile D. EtBr concentration in the reaction lane 1, 1 mM; lane 2, 0.5 mM; lane 3, 0.1 mM; lane 4, 0.01 mM and lane 5, no inhibitor. The lower panel represents the coomassie-stained SDS-PAGE profile, which shows that the addition of EtBr did not cause aggregation of sensor kinase.

DETAILED DESCRIPTION OF THE PRESENT INVENTION

Accordingly, the present invention relates to a package of screening methods for developing drugs against pathogenic microbes having two-component system of DevR-DevS and/or DevR-Rv2027c and its homologues, said method comprising steps of over-expressing DevR, DevS, and Rv2027c and their single domain derivatives including mutant variant proteins, autophosphorylating DevS, and Rv2027c proteins and thereafter, phosphotransfering to DevR and its derivatives in SDS-PAGE or High-throughput format in the presence of a test compound, and determining the drug-potential of the test compound, wherein the potential of the drug is inversely proportional to (i) the degree of autophosphorylation of DevS and Rv2027c, (ii) the degree of phosphotransfer-based dephosphorylation of DevR and/its single domain derivative, and (iii) the degree of dephosphorylation of phosphorylated species of DevS and Rv2027c and their single domain derivatives, and a method of treatment, and a composition thereof.

This invention relates to a process for identification and development of therapeutic modalities and drugs effective against tuberculosis and using the DevR-DevS and DevR-Rv2027c signal transduction systems as targets for anti-tubercular therapy. The invention discloses detailed analysis of the phosphorylation reactions characteristic of the aforementioned two-component systems and high-throughput format based assay systems useful in large scale screening of inhibitors and compounds against the phosphorylation pathways and reactions disclosed herein. The invention also describes the novel utilization of mutant and/or defective proteins in screening of inhibitors of these phosphorylation pathways. The invention also discloses inhibitor modalities capable of inhibiting the phosphorylation pathways and autophosphorylation of sensor kinase in particular.

The invention described herein provides the first evidence of the bonafide nature of DevR-DevS two-component system and that of cross talk or cross-communication between Rv2027c and DevR at biochemical level involving phosphorylation of the respective proteins. The DevR-DevS two-component system represents the third example of a two-component system being involved in virulence of M. tuberculosis, the other two-component systems of M. tuberculosis for whom roles in virulence has been reported being Rv0981-0982 (Zahrt and Deretic, 2001) and phoP-phoQ (Perez et al., 2001). Since, hypoxia has been recognized as a key signal for the DevR-DevS two-component system, it would be reasonable to suggest its involvement in latent infection, a unique characteristic of tubercle bacilli. Furthermore, the other two-component systems which have been implicated in virulence are yet to be characterized at the biochemical level and hence as of now cannot be utilized for screening for lead molecules using biochemical screening protocols.

It is believed that the expression of one or more genes induced during hypoxia is regulated by the DevR-DevS system which in turn could be regulating mycobacterial dormancy and virulence. Therefore, this invention offers the means of purifying the DevR, DevS and Rv2027c proteins in active form and a means of screening for new anti-microbial/bacterial drugs, compounds, agents or molecules, which by blocking DevR and DevS/Rv2027c activity can effectively interfere with the activity of one or many of these DevR-regulated gene products associated with bacterial/mycobacterial survival and dormancy and can consequently break the mycobacterial dormancy. Specific examples thereof have been provided herein. Thus, DevR-DevS/Rv2027c-DevR two-component systems offer very unique loci for interfering with mycobacterial life-cycle within the host.

The present invention involves utilization of DevR-DevS (Rv3133c-Rv3132c) and DevR-Rv2027c signal transduction pathways as targets for therapy against diseases caused by mycobacterial organisms including all forms of Mycobacterium tuberculosis and other mycobacteria possessing these two-component systems. The invention further covers the utilization of these proteins as modes for screening anti-bacterial, anti-mycobacterial, bactericidal and/or bacteriostatic drugs and/or compounds that target these signal transduction pathways. Examples demonstrating the utility of the assays are also provided.

In an embodiment of the present invention, a package of screening methods for developing drugs against pathogenic microbes having two-component system of DevR-DevS and/or DevR-Rv2027c and its homologues is provided, said method comprising steps of:

a. overexpressing DevR, DevS, and Rv2027c and their single domain derivatives including mutant variant proteins,
b. autophosphorylating DevS, and Rv2027c proteins and thereafter, phosphotransfering to DevR and its derivatives in SDS-PAGE or High-throughput format in the presence of a test compound,
c. determining the drug-potential of the test compound, wherein the potential of the drug is inversely proportional to (i) the degree of autophosphorylation of DevS and Rv2027c, (ii) the degree of phosphotransfer-based dephosphorylation of DevR and its single domain derivative, and (iii) the degree of dephosphorylation of phosphorylated species of DevS and Rv2027c and their single domain derivatives.

In yet another embodiment of the present invention, the DevS derivatives are selected from a group comprising $DevS_{201}$, $DevS_{578}$, $DevS_{201}$-H395Q, $DevS_{201}$-H397Q, $DevS_{201}$-H397A, and $DevS_{201}$-N503D.

In yet another embodiment of the present invention, the Rv2027c derivatives are selected from a group comprising $Rv2027_{194}$, and $Rv2027_{194}$-H392Q.

In yet another embodiment of the present invention, the DevR derivative is $DevRN_{145}$ and also includes mutant proteins comprising DevR-D8N, DevR-D9N, DevR-D54V, DevR-D54N and DevR-K104E.

In another embodiment of the present invention, the proteins are overexpressed in E. coli.

In yet another embodiment of the present invention, the test compound shows activity selected from a group comprising antibiotic activity, antibacterial activity, anti-microbial activity and anti-tubercular.

In yet another embodiment, the method of the invention helps identify anti-tuberculosis drugs, anti-mycobacterial drugs and drugs against disease conditions caused by bacteria such as pneumonia, pertussis, listeriosis, enterobacterial diseases, cholera, etc.

The present invention also provides for treating disease conditions caused by pathogenic microbes having two-component system of DevR-DevS and/or DevR-2027c or homologues, said method comprising step of administering pharmaceutically effective amount of a compound acting as inhibitor of the phosphorylation reaction of DevR, DevS, and Rv2027c and their single domain derivatives including mutant variant proteins, to a subject in need thereof, optionally along with pharmaceutically effective additives.

In yet another embodiment of the present invention, the compounds are selected from a group comprising Ethidium Bromide (EtBr), Bromo Phenol Blue (BPB), 2-mercapto benzimidazole (2-MBI) and their derivatives.

In still another embodiment of the present invention, BPB shows 50% inhibition ($IC_{50}$) of DevS/Rv2027c activity at a concentration ranging between 1.3 and 2.0 mM.

In another embodiment of the present invention, EtBr shows 50% inhibition (IC50) of Rv2027c activity at a concentration ranging between 0.5 and 1.0 mM and 35% inhibition of DevS in the presence of 2.5 mM.

In another embodiment of the present invention, 2-MBI shows 50% inhibition ($IC_{50}$) of DevS/Rv2027c activity at concentration ranging between 0.3 and 0.8 mM.

In yet another embodiment of the present invention, the additive is selected from a group comprising magnesium stearate, cellulose, calcium carbonate, starch-gelatin paste, talc, carrier, excipient, and diluent.

In another embodiment of the present invention, the compound is administered orally, by inhalation, or by implantation.

In yet another embodiment of the present invention, the physical state of said compound includes but is not limited to capsule, tablet, syrup, concentrate, powder, granule, aerosol, and beads.

In yet another embodiment of the present invention, said method of using said composition has little or no adverse effect on health.

The present invention provides a composition useful in the management of disease conditions caused by pathogenic microbes having a two-component system of DevR-DevS and/or DevR-2027c or homologues said composition comprising a drug selected from a group consisting of Ethidium Bromide (EtBr), Bromo Phenol Blue (BPB), 2-mercapto benzimidazole (2-MBI), and 2-phenylbenzimidazole and active derivatives thereof, and a pharmaceutically acceptable additive.

In an embodiment of the present invention, the additive is selected from a group including but not limited to magnesium stearate, cellulose, calcium carbonate, starch-gelatin paste, talc, carrier, excipient, and diluent.

In yet another embodiment of the present invention, the ratio of drug and the additive ranges between 1:10 to 10:1.

In yet another embodiment of the present invention, the compound is administered orally, by inhalation, or by implantation.

In still another embodiment of the present invention, the physical state of said compound included but is not limited to capsule, tablet, syrup, concentrate, powder, granule, aerosol, and beads.

Table 1 lists plasmids used in this study and list of single domain derivatives and amino acid substitution mutants of DevR, $DevS_{201}$ and $2027_{194}$ proteins used in this study.

TABLE 1

Plasmids used in this study and list of amino acid substitution mutants of DevR, $DevS_{201}$ and $2027_{194}$ proteins used in this study.

| Plasmid | Features | Primers (mutated bases are underlined) | Putative role of residue/s* | Source |
|---|---|---|---|---|
| pPROEx-HT | E. coli protein expression vector expressing recombinant proteins with N - terminal $His_6$ - tag | | | Invitrogen Inc. USA |
| pDSR217 | pPROEx-HTa carrying wild type devR gene | F:5'GCCCATATGGTAAAGGTCTTCTTGG 3'<br>F:5'CCGGCTTTTTCGTCGACGAGG 3' | | This study |
| pSCS201 | pPROEx-HTb carrying wild type $devS_{201}$ gene encoding cytosolic portion of $DevS_{378-578}$ | 5' CAACGTCGGATCCGCGAACTCGACG 3'<br>5' GGCGCCGGGATCCTGGCACTAGG 3' | | S. Chakravorty, AIIMS |
| pDSS578 | pPROEx-HTc carrying complete wild type devS gene encoding DevS578 | 5' CGACGGATCCGCAATGCGTCCA 3'<br>5' GGCGCCGGGATCCTGGCACTAGG 3' | | This study |
| pDSH194 | pPROEx-HTc carrying wild type $Rv2027_{194}$ gene encoding cytosolic portion of $2027_{380-573}$ | 5' GCGAGAAGTGGAGGATCCTGACC 3'<br>5' GGATTGCGCGGATCCGTCGACGCC 3' | | This study |
| pDSS395Q | H395Q substitution in $devS_{201}$ gene in plasmid pSCS201 | F:5'GCCCGTGACCTCCA<u>A</u>GACCATGTCATCCAGCGG3'<br>F:5'CCGCTGGATGACATGGTCT<u>T</u>GGAGGTCACGGGC3' | Site of phosphorylation | This study |
| pDSS397Q | H397Q substitution in $devS_{201}$ gene in plasmid pSCS201 | F:5'GACCTCCATGACCA<u>A</u>GTCATCCAGCGG3'<br>F:5'CCGCTGGATGACTTGGTCATGGAGGTC3' | None | This study |

TABLE 1-continued

Plasmids used in this study and list of amino acid substitution mutants of DevR, DevS$_{201}$ and 2027$_{194}$ proteins used in this study.

| Plasmid | Features | Primers (mutated bases are underlined) | Putative role of residue/s* | Source |
|---|---|---|---|---|
| pDSS397A | H397A substitution in devS$_{201}$ gene in plasmid pSCS201 | F:5' GACCTCCATGACGATGTCATCCAGCGG 3'<br>R:5' CCGCTGGATGACATCGTCATGGAGGTC 3' | None | This study |
| pDSSN503D | N503D substitution in DevS201 gene in plasmid pSCS201 | F:5' GAAGCGGTCAGCGACGCGGTTAGACATG 3'<br>R:5' CATGTCGTAACCGCGTCGCTGACCGCTTC 3' | Part of ATP binding domain | This study |
| pDSH392Q | H392Q substitution in 2027$_{194}$ gene in plasmid pDSH194 | 5' GCACGTGATCTGCAAGACCACGTCATCCAG 3'<br>5' CTGGATGACGTGGTCTTGCAGATCACGTGC 3' | Site of phosphorylation | This Study |
| pDSR54N | D54N substitution in devR gene in plasmid pDSR217 | F:5'GCGGATATGTCGTCGAAGACATCAAGGGAATG3'<br>R:5'CATTCCCTTGATGTCTTCGACGACATATCCGC3' | Site of phosphorylation | This study |
| pDSR54V | D54V substitution in devR gene in plasmid pDSR217 | F:5'GTCGCGGTGCTGGTTGTCCGGTTGCCC 3'<br>R:5'GGGCAACCGGACAACCAGCACCGCGAC 3' | Site of phosphorylation | This study |
| pDSR8N | D8N substitution in devR gene in plasmid pDSR217 | F:5'CTTCTTGGTCAATGACCACGAGGTGGTG 3'<br>R:5'CACCACCTCGTGGTCATTGACCAAGAAG 3' | Mg$^{+2}$ binding | This study |
| pDSR9N | D9N substitution in devR gene in plasmid pDSR217 | F:5'CTTCTTGGTCGATAACCACGAGGTGGGTG 3'<br>R:5'CACCCACCTCGTGGTTATCGACCAAGAAG 3' | Mg$^{+2}$ binding and catalysis | This study |
| pDSR104E | K103E substitution in DevR gene in plasmid pDSR217 | F:5'GCGGATATGTCGTCGAAGACATCAAGGGAATG3'<br>R:5'CATTCCCTTGATGTCTTCGACGACATATCCGC3' | Invariant, required for phosphorylation induced activation. | This study |

*Based on role of 'conserved residues' (Stock et al., 2000)

The putative Rv2027c protein is 62.5% identical to DevS protein and contains H, N, D/G1 and G2 boxes typical of histidine kinases. It was speculated therefore that Rv2027c being a potential orphan sensor kinase, could be expressed, autophosphorylated and in turn participate in a phosphotransfer event with DevR protein. This hypothesis was tested and confirmed to occur in vitro (described herein).

Figure 1:
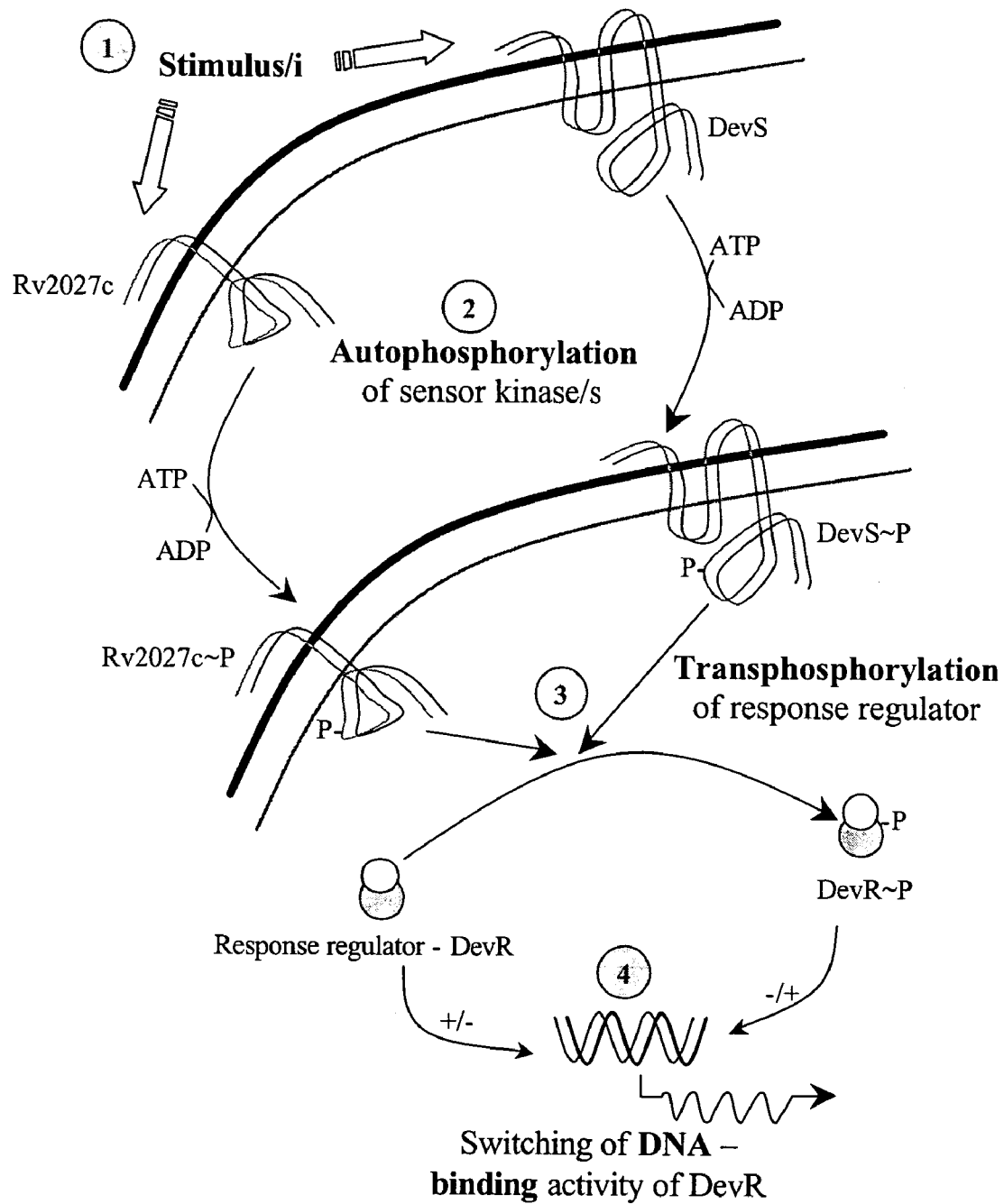
FIG. 1. Schematic of two component signal transduction system and potential points of interception. 1. Detection of the stimuli by the histidine sensor kinase DevS or Rv2027c. 2.

It is proposed that use the phosphorylation assays to screen for lead molecules or inhibitors that block these phosphorylation reactions and identify bactericidal, antimicrobial, or anti-tubercular compounds that interfere with these signal transduction events and thereby inhibiting the expression of downstream gene targets under their control (see FIG. 1).

The DevR-DevS two-component signal transduction system was identified by subtractive hybridization analysis of virulent H37Rv and an avirulent H37Ra strain of M. tuberculosis (Kinger and Tyagi, 1993). The bonafide nature of this two-component system has been validated at the protein level by establishing the phosphorylation potentials of the respective proteins, which forms the basis of all two-component systems. The biochemical function has been validated for Rv2027c-DevR pathway as well. DevR, DevS and Rv2027c proteins have been overexpressed in E. coli, purified and refolded in vitro. The refolded proteins have been utilized in in vitro phosphorylation assays, namely; autophosphorylation of the histidine sensor kinases DevS and Rv2027c and phosphotransfer of the phosphoryl moiety from phosphorylated sensor (DevS/Rv2027c) to DevR. Successful biochemical reconstitution of these two-component systems has provided the means for the development of rapid high-throughput assays to screen compound or drug libraries for lead molecules that could interfere with these signal transduction pathways. Besides using the full length DevS and DevR proteins used in the aforementioned assays, the C-terminal single domain catalytically active portions of the sensor kinases namely, DevS$_{201}$ and Rv2027$_{194}$ and N-terminal single-domain catalytically-active portion of response regulator protein-DevRN$_{145}$ have been biochemically examined as well and have been demonstrated to be catalytically active as the full length parent proteins. This also provides the potential of using single-domain proteins of the aforementioned and stated two-component system as tools or targets for the screening disclosed herein.

High-throughput assays for screening for inhibitors of phosphorylation reactions of the participating partners in the two-component signal transduction pathway, i.e. sensor kinases DevS/Rv2027c and response regulator DevR have been developed and provide a means for screening compound libraries very rapidly. Furthermore, the availability of specific phosphorylation-defective individual proteins also provides a means for screening out false leads and for further effective and scientific study of the kinetics of the inhibitors. Examples are provided herein to illustrate the utility of these assays in screening of inhibitors.

Utility of the invention: Tuberculosis is the single infectious agent causing more deaths world over than all other infectious agents together. A majority of the world's population who might not be suffering from active disease are predicted to be carriers of the disease. Active disease is essentially the result of an intricate interplay between the pathogen and the host immune defense system. In majority of the cases the progression of the disease is halted and the bacilli lie dormant in the host for long periods of time before reactivating to cause clinical disease. Such a situation is termed as latent infection wherein granulomas form around the infective foci and disease progression is halted. Clinically these granulomas do not contain dead organisms but harbor dormant bacilli quite capable of causing full-blown disease on reactivation (Grange, 1992; Stead et al., 1968).

Approximately 10% of latent infections reactivate, resulting in active infectious disease months to years after initial infection (Stead, 1967). The adaptation of tubercle bacilli to dormancy has long been considered to be associated with hypoxia, low pH and/or nutrient limitation prevalent in granulomas. Recent reports have demonstrated hypoxia to induce the expression of DevR-DevS two-component system (Kapur, V., Ph.D. Thesis, 2001; Tyagi and Kapur, PCT/IN02/00022; Sherman et al., 2001; Boon et al., 2001).

A devR functional knockout strain of *M. tuberculosis* H37Rv (constructed in Dr. J. S. Tyagi's laboratory) is attenuated for virulence and causes minimal pathology in liver and lung of infected guinea pigs. A nearly thousand-fold lower number of viable bacilli were recovered from spleens of guinea pigs injected with the mutant strain suggesting the mutant is either unable to establish itself or is cleared off rapidly from secondary sites of infection such as spleen, pointing towards the importance of this system for establishing persistent infection (Kapur, V., Ph.D. Thesis, 2001; Tyagi and Kapur, PCT/IN02/00022). A number of other genes namely, katG, acr, icl, pca, sigF etc. have been implicated in persistence of *M. tuberculosis* that can serve as potential targets for drugs against persistent/latent bacilli (Chen et al., 2000; Glickman et al., 2000; Li et al., 1998; McKinney et al., 2000; Weber et al., 2000; Yuan et al., 1998).

Since, DevR-DevS two-component system belongs to the family of regulatory proteins it is likely that one or several genes implicated in latency and persistence may be regulated by the DevR-DevS system. Though the target genes are yet to be identified, inhibition of a regulatory system active in hypoxia could provide a means for inhibiting the expression of multiple genes induced during hypoxia, including perhaps genes upregulated within granulomas. Functional reconstitution of this two-component system was important to confirm the functional nature of this system. The validation of the signal transduction pathway at protein level provides a platform for rapid screening of inhibiting compounds that could interfere with the signal transduction phosphorylation pathways at multiple steps (1 through 4, see FIG. 1).

*M. tuberculosis* genome sequence revealed presence of an orphan sensor kinase in the genome-Rv2027c. There is a high degree of sequence homology (62.5% identity) between DevS with Rv2027c proteins (Dasgupta et al., 2000). It is possible therefore that Rv2027c may function as a sensor kinase for DevR protein. This cross talk was also investigated and demonstrated to occur in vitro indicating that Rv2027c-DevR could also be used as a target for anti-infective therapy/ies along with the DevR-DevS system.

Conventional drugs target pathways involved in bacterial growth and division such as cell-wall biosynthesis and DNA replication. Their poor activity against slow growing and non-replicating bacteria is thought to be an important reason why currently used regimens take so long to eradicate infection (Parrish et al., 1998) and many a times fail to achieve complete clearance. The discovery of bacterial genes that play key roles in persistence (see above) has paved the way for the identification of molecules in dormant bacteria that can be targeted by new classes of drugs. The involvement of DevR in virulence makes it an attractive target for chemotherapeutic agents directed tubercle bacilli.

Oxygen limitation and hypoxia upregulate the synthesis of DevR-DevS two-component system in *M. bovis* BCG, *M. tuberculosis* and *M. smegmatis* in an in vitro dormancy model (Tyagi, J. S., DST report, October, 2001; Sherman et al., 2001; Boon et al., 2001 and Mayuri et al., 2002). This finding has crucial implications for *M. tuberculosis* since hypoxia has often been referred to as a characteristic environmental property of granulomas and a likely trigger for the initiation and/or maintenance of the dormancy response. Modulation of gene activity by DevR is likely to be achieved through its putative DNA-binding activity as is known to occur in other bacterial two-component systems (Dziejman and Mekalanos, 1995). Experiments are currently underway to identify the gene targets under its regulatory control and the involvement of hypoxia in modulation of its activity.

There is an urgent need for new anti-tuberculosis drugs to combat drug-resistant forms of the pathogen and to treat chronic tuberculosis. Pathogenesis Inc. (USA) has recently announced that the compound PA-824, belonging to the bicyclic nitroimidazofuran family of compounds, if approved will be the first new *tuberculosis*-specific drug in market in 30 years. It has shown activity against both replicating and static tubercle bacilli as well as multidrug-resistant bacilli (Stover et al., 2000).

The potential of DevR as a new anti-tubercular drug target has been described in earlier patents (Indian patent appl. no. 1286/DEL/2001 and PCT appl. no. PCT/INO2/00022). The phosphorylating activities of DevS, DevR and Rv2027c proteins have not been disclosed in the earlier patents. Thus, the present invention provides novel methods of screening potential inhibitors to these phosphorylation activities using these proteins in a SDS-PAGE electrophoretic assay or high-throughput format.

Protein-Structure Based Design of Agonists/Inhibitors/Antagonists to Sensor Kinase and/or Response Regulator Protein-DevR.

Once the three-dimensional structure of a protein is determined, a potential drug/inhibitor/agent can be examined through the use of computer assisted modeling and docking softwares like GRAM, DOCK etc. This procedure includes computer fitting and docking of chemical compounds and moieties from a library of structured molecules to the protein structure (West et al., 1995) herein the sensor kinases DevS or Rv2027c and the response regulator protein DevR to ascertain the efficacy of the binding and 'docking' of the potential inhibitory agent takes place and whether the potential 'dock' can become a potential 'inhibitor' for the interaction surface like, sensor kinase dimerization interface, sensor kinase-response regulator interaction interface, sensor kinase signal sensing interface, sensor kinase phosphorylation interface, response regulator phosphorylation interface, response regulator-DNA interaction interface among other structurally critical faces of the respective proteins. Computer programs can also be employed to estimate the attraction, repulsion, and strearic hindrance of the agents to various surface area (as mentioned above). Such a rational structure-based drug designing approach requires a refined 3-D structure of the target protein, herein it would be the structure of DevS/Rv2027c and DevR proteins. Such a high-resolution and high quality 3-D data needs sufficient quantities of purified and active protein which can be obtained in great amounts using the constructs, methods and protocols described in this patent application.

To provide a framework for the structure-based drug design approach a preliminary structure of the target protein can also be modeled from the 3-D structure databases using modeling software like Swiss-Model which automatically generates a predictive protein structure model on the basis of protein sequence homology of the target protein with a protein whose structure has been elucidated earlier. Such a approach was fruitful for the response regulator protein DevR and its 3-D structure was predicted from the Swiss-Model server (FIG. 11) on the basis of sequence homology with NarL response regulator protein of $E.$ $coli,$ whose 3-D structure have been elucidated (Baikalov et al., 1996). Though the structure provided is not the actual structure and is a model only, it can very well serve a starting material for the structure-based rational drug design.

Computer modeling allows the selection of a finite number of rational chemical modifications, as opposed to the countless number of essentially random chemical modifications that could be made, any of which might lead to a useful drug. Each chemical modification requires additional chemical steps, which while being reasonable for the synthesis for a finite number of compounds, might become overwhelming if all the possible modifications need to be synthesized for initial screening. Thus through the use of 3-D structure analysis and computer modeling, a large number of these compounds can be rapidly screened on the computer monitor without actually synthesizing them and a few likely candidates can be identified and screened without the laborious synthesis of untold number of compounds. Once a potential candidate is identified it can either be selected from a commercial source like large chemical companies viz. Merck, Glaxo-Smithcline, Monsanto, Eli Lily, DuPont etc. or the chemical can also be synthesized de novo.

The so identified 'inhibitor-compound' can then be tested in standard high-throughput in vitro (described in this patent application) and in vivo whole-cell assay systems to evaluate the efficacy of not only the modeling methodology but also of the inhibitor activity as well. Using the approach described herein along with the modeled DevR structure besides a number of structures of sensor kinases and response regulators which can be obtained a detailed analysis of various reported inhibitors (Macielag and Goldschmidt, 2000; Matsushita and Janda, 2002) and new identified compounds can be made and their mode of action can also be predicted. But, for all subsequent experiments and predictions in the current scenario, i.e., for the DevR-DevS and DevR-Rv2027c two-component systems a refined 3-D structure either by X-ray crystallography or by solution NMR spectroscopy needs to be generated for the individual participating proteins to confirm not only the structural predictions but also to evaluate the actual structural variations and kinetics of all the participating proteins.

Phage Libraries for Drug/Inhibitor 'Peptide' Screening-Novel use of Mutant Proteins.

Many a phage-library systems have been constructed at the genetic level, which upon infection into $E.$ $coli,$ produces random peptide sequences from 7-20 mers in structurally unconstrained and constrained forms, displayed on the surface of phage particles. Such a huge repertoire of random peptides makes such a system analogous to having a huge chemical library, which is ready to be screened for the peptide of choice. A number of approaches have been reported in the literature for such screening. A novel utilization of the mutant proteins (of both sensor kinases and response regulator proteins) in such a screening cum elimination-'biopanning' protocol is disclosed herewith.

Various strategies can be proposed for utilization of various mutant proteins in screening steps to eliminate the non-specific binders or binders with weak affinity or binders which do not affect the phosphorylation of the respective proteins, included in this study. In the following methodology, the outline of protocol which can be utilized is proposed as follows:

1. Screening of Peptides (Random and Phage-displayed) Which Inhibit Autophosphorylation of Sensor Kinases Immobilization of the sensor kinase protein includes, but is not limited to, $DevS_{201}$ or $DevS_{578}$ or $Rv2027_{194}$ sensor kinase proteins, which can include other full-length and/or single domain proteins or their derivatives thereof of the mentioned sensor kinases on a solid support/matrix. Such solid support/matrix includes, but is not limited to ELISA plates (polystyrene matrix), magnetic beads, poly-lysine coated plates, strepavidin-coated beads, $Ni^{+2}$-NTA matrix or other affinity matrices thereof.

After immobilization of the protein under analysis, viz. the sensor kinases or derivatives thereof, using the specific immobilization protocol/s as per the manufacturer or established protocol, the immobilization matrix coupled protein is thoroughly washed with wash buffer (PBS/TBS).

Once the immobilized beads or matrix have been washed, a desired amount of coated and/or immobilized protein equivalent of matrix (for example 100 µg, but does not limit to this amount) is incubated with the indicated number of phage (for example, $10^{11}$ virions for NEB system 7-mer which can be pre-incubated with the matrix to which the test protein is immobilized on, essentially to remove the matrix binding phage) for the indicated duration or conditions as mentioned by the manufacturer.

The matrix and/or beads are washed stringently with TBS-T (Tween-20) as indicated in the manufacturer's protocol.

In the next step, the phage-bound protein immobilized on beads/matrix is incubated with equivalent amount of phosphorylation-defective mutant sensor kinase protein, i.e. DevSH395Q or DevSN503D protein if DevS is immobilized and Rv2027H392Q for $Rv2027_{194}$ protein for 10-30 minutes at RT. This step will facilitate not only the removal of low-affinity phage or peptides from the interacting pool, but it will also selectively leave behind the peptides binding with phosphorylation pocket, even with weak affinity, and also those peptides which bind with high affinity to the immobilized sensor kinase.

After this wash, the interacting phages are eluted from the immobilized protein using either non-specific elution conditions like 0.2M Glycine pH~2.2 or triethanolamine, pH~10.5 or using specific elution conditions like using imidazole to release the protein-peptide-phage complex from the $Ni^{+2}$-NTA beads (if that has been used as the matrix). Using specific elution conditions, for example, imidazole, to elute the specific protein-peptide complex carries immense advantage over non-specific elution conditions using glycine or triethanolamine, which may lead to elution of phages or peptides which interact with the matrix alone. For example, peptides which have binding affinity to the plate or beads etc. will be eluted as well in these elution conditions. Elution of such non-specific phages or matrix binding peptides interferes in all the subsequent screening steps and might lead to false leads.

The eluted peptide-displayed phage is eluted as per the manufacturer's protocol and use the amplified phage for next round of bio-panning (selection-elimination cycle).

In the next panning step, the matrix for immobilization of the sensor kinase protein can be changed (i.e. if ELISA plate has been used for coating in first panning then magnetic beads can be used for second panning). This could eliminate the matrix binding phage displayed peptides quite effectively and would also increase the signal to noise ratio and will enhance to probability of recovering the protein binding phage.

The above mentioned protocol is repeated 2-3 times, i.e., for total three-four rounds of panning with increasing the concentration of Tween-20 in the subsequent washes, for example 0.2% in 1st panning, 0.25% in 2nd panning and 0.5% in 3rd and 4th panning and alternating the immobilization matrix as well.

In the third and fourth round of panning, the immobilized protein-peptide/phage complex is subjected to washing with ATP/Mg$^{+2}$ complex (used as ligand here) after the wash with the mutant protein to elute specifically the phage binding to the ATP-binding domain and the phosphorylation pocket of the sensor kinases. Such ligand-based elution will yield peptides, which would be good candidates for checking the inhibition of phosphorylation reaction.

After the three or four rounds of panning, the individual clones can be analyzed by sequencing the peptides as well as by performing the binding assessment of the peptides in a phage-ELISA setup.

Once this is validated, the inhibiting peptides can be synthesized and utilized for the in vitro and in vivo assays to evaluate their efficacies and their mode of action on the phosphorelay pathway.

2. Screening of Peptides Which Inhibit the Phosphotransfer Reaction to DevR Protein.

Analogous to the sensor kinases, the response regulator protein can also be subjected to peptide screening, utilizing the same or similar aforementioned protocol with suggested deviations/modifications as mentioned below.

The DevR or DevRN$_{145}$ protein can be immobilized on the matrix/beads in panning for peptides having potential for inhibiting phosphorylation reaction, The phosphorylation defective DevR mutant proteins, viz. D54V, K104E, D8N etc., or the single domain derivates, viz. DevRN$_{145}$ or DevR$_{C-term}$ can also be used for washing off the low affinity binding peptides For eluting specific phosphorylation pocket binding peptides, the immobilized DevR-peptide complex can be washed with phosphorylated sensor kinase/s (herein serving as elution 'ligand') to induce phosphorylation of the DevR/DevRN$_{145}$ response regulator protein. In such a condition, the peptides which bind to the sensor kinase-response regulator interaction interface and to the phosphorylation pocket of the DevR/DevRN$_{145}$ protein will be liberated along with the peptides which will be displaced as a result of phosphorylation induced structural modification in the response regulator protein.

All such peptides can then be subjected to extensive analysis similar to the one used for histidine sensor kinase proteins.

As used herein the term 'effective peptide' refers to a peptide or its analog, capable of interfering with the phosphorylation reaction/s for which it was screened for, i.e. peptide either capable of inhibiting the autophosphorylation of sensor kinase/s and/or transphosphorylation of response regulator protein DevR through the sensor kinase/s-DevS or Rv2027c.

The effective peptides can be synthesized in large quantities for use in in vivo models and eventually in humans to aid in fight against tuberculosis. It should be emphasized that the synthetic peptide synthesis is relatively non-labor intensive, quality controlled, easy to manufacture and large quantities can be also be produced quite cheaply. Utilization of synthetic antibody libraries for 'potentially' inhibiting modalities.

As mentioned above, there is an urgent need to identify novel drug targets for the development of new drugs that would be effective against tuberculosis that is resistant to treatment by drugs that are in use today. Furthermore, there is a grave need for effective drugs that can target chronic forms of tuberculosis in contrast to the currently administered drugs that target actively replicating bacilli.

Earlier reports from Dr. Jaya S. Tyagi's laboratory have suggested that the devR gene is more likely to be related in chronic infection process and is less relevant to the growth per se under aerated conditions or in the early events of infection. It was observed that the mutant strain failed to cause severe progressive disease and pathology under the experimental conditions in guinea pigs as compared to the wild type H37Rv strain.

The DevR protein belongs to the response regulator class of regulatory proteins. It is likely that it orchestrates the adaptation of tubercle bacilli to the hostile environment of the host. The two-component system's regulatory network functions through a phosphorylation pathway, where DevS histidine sensor kinase (HK) protein senses an environmental cue/stimulus in response to which it undergoes autophosphorylation at a conserved His$^{395}$ residue. The phosphorylated DevS species then transfers the phosphoryl moiety to the DevR protein via a phosphotransfer event at a conserved Asp$^{54}$ residue.

A phosphorylation-induced change in DevR protein structure likely changes its DNA binding ability, leading to modulation in expression of genes under its control. It is known that this two-component system is responsive to hypoxia (Boon et al., 2001; Sherman et al., 2001; Tyagi, J. S., DST report, October, 2001; Mayuri et al., 2002), a key factor involved in persistence and it is also suggested that this system is indeed involved in causing chronic infection (Kapur, V., Ph.D. Thesis, 2001; Tyagi and Kapur, PCT/IN02/00022). It thus provides a novel target for the development of drugs active against the bacilli located in the granulomas. It is anticipated that disabling the function of a regulatory system such as DevR-DevS and DevR-Rv2027c will lead to the inactivation of bacterial pathway(s) modulated by it in response to hypoxia. The studies described here suggest the protocol and biochemical assays which can be utilized to screen for inhibitor molecules/compounds/drugs against these pathways/system and leading to functional inactivation of the system (FIG. 1). Furthermore, the setup and details of high-throughout assays for rapid screening of potential inhibitors towards both autophosphorylation and phosphotransfer reaction/s from the corporate compound libraries or combinatorial libraries is also described. Besides these screening protocols, the invention also discloses novel use of EtBr and BPB as inhibiting modalities along with potential of using specific antibodies and peptides as inhibitory species to these two-component system/s.

The invention is further explained with the help of following examples and strategies. These examples are mere illustrations and should not be construed to limit the scope of the present invention in any manner.

EXAMPLES

Example 1

Cloning, Overexpression and Purification and Refolding of DevR, DevS and Rv2027c and Their Single Domain Derivative/s and Mutant Variant Proteins A. Cloning of DevR, DevRN$_{145}$, DevS$_{201}$, DevS$_{578}$ and Rv2027$_{194}$ and Generation of Their Single Domain and Mutagenic Derivatives All routine recombinant DNA work was performed as described (Sambrook and Russell, 2001). *M. tuberculosis* H37Rv DNA was prepared by boiling cells in the presence of 0.1% Triton X-100 for 25 minutes at 95° C. and the supernatant recovered after centrifugation was used as a source of template DNA in PCR. Full length devR, N-terminal truncated devS$_{201}$, full length devS$_{578}$ and N-terminal truncated Rv2027$_{194}$ genes were amplified from *M. tuberculosis* DNA by PCR using Pfu DNA polymerase and primers that contain restriction enzyme sites engineered in them (FIG. 2, Table 1).

For the expression of N-terminally His$_6$-tagged DevR protein, the devR PCR product was digested with NdeI and SalI and after blunting with T4 DNA polymerase, cloned in blunted EcoRI site of pPROEx-HTa plasmid expression vector (Invitrogen Inc., USA) to generate pDSR217. For the expression of DevRN$_{145}$ the pDSR217 plasmid was digested with PpuMI (whose restriction site maps within the gene corresponding to the linker region of the response regulator protein, DevR and separates the catalytically-active phosphorylation proficient N-terminal domain from the C-terminal DNA-binding domain) and XhoI (which digests in the vector backbone). This PpuMI-XhoI double digestion liberates the C-terminal fragment of the devR gene containing the entire DNA-binding domain. Filling-in of the digested expression vector pDS217 with Klenow polymerase, the resealing/relegation step provides the vector pDSR$_{145}$ which overexpress the $_{145}$ amino acid long N-terminal DevR protein, DevRN$_{145}$.

For the expression of a N-terminally His$_6$-tagged DevS$_{201}$, DevS$_{578}$ and Rv2027$_{194}$ proteins, their respective PCR products were digested with BamHI and cloned in BamHI digested pPROEx-HTb, pPROEx-HTc and pPROEx-HTc expression vectors respectively to generate plasmids pSCS201, pDSS578 and pDSH194.

For site directed mutagenesis of the respective plasmids, point mutations were introduced into pDSR217, pSCS201, pDSH194 using the QuikChange site-directed mutagenesis kit (Stratagene Inc., USA) and designed mutageneic oligonucloetides. The mutagenic oligonucleotides used are shown in Table 1.

All the expression constructs encoding wild type and mutant proteins (FIG. 2) were verified by automated DNA sequencing using 377 ABI Prism DNA sequencer.

B. Protein Purification Protocol a. Cell Growth.

All the recombinant plasmids (Table 1) were freshly transformed into *E. coli* BL23(DE3) except for pDSS578 which was transformed in *E. coli* DH5α. Primary starter culture was inoculated in 5 ml Luria broth or 2×YT media containing ampicillin from one single isolated colony from the transformed plate, which was stored at 4° C. after transformation and is not older than 2 weeks and was grown at 37° C. for 12-16 hours.

The following morning the entire 5 ml of the primary culture was added in 500 ml of 2×YT media (1% subculture) containing ampicillin (100 µg/ml) and incubated at 37° C. with shaking (200 rpm) till an OD600 of 0.4-0.6 was reached. The production of recombinant proteins was induced by the addition of 1 mM of IPTG and the culture was incubated at 37° C. for an additional 5-6 hours after which the cells were harvested by centrifugation.

The following protocol was followed for cell growth and induction for DevS$_{578}$ protein. *E. coli* DH5α cells carrying the pDSS$_{578}$ plasmid were subcultured (1%) in 500 ml 2×YT media containing 100 µg ml-1 of ampicillin and 1 mM of IPTG and incubated at 37° C. with shaking (200 rpm) for 7-8 hours and induced cells were harvested by centrifugation.

b. Purification and On-Column Refolding of Recombinant Proteins.

Induced cell pellets (for all the proteins) were resuspended in phosphate buffered saline, pH 7.4 and disrupted by sonication (using microtip for 1 minute bursts each time for 3 times). Soluble and insoluble protein fractions were separated by centrifugation. (Analysis of the soluble and insoluble fractions by SDS-PAGE indicated that the overexpressing fusion proteins were localized essentially in inclusion bodies).

The insoluble inclusion bodies containing the recombinant proteins were solubilized in 1/100 th culture volume equivalent of denaturation buffer (i.e. 5 ml buffer for 500 culture pellet): 20 mM Tris HCl, pH 8.0, 10% glycerol, 500 mM NaCl and 20 mM imidazole containing 6 M guanidinium hydrochloride or 8 M urea and the lysate was incubated for 2-16 hours at 30-37° C. to facilitate complete solubilization of denatured proteins. For DevR protein solubilization using 6M HCl is recommended.

Alternatively, the cell pellet was directly resuspended in denaturation buffer (without separating soluble and insoluble proteins) and incubated at 37° C. with shaking for 12-16 hours for solubilization.

After solubilization, the cell lysate was centrifuged at 20,000-28,000 rpm for 1 hour at 25° C., to separate the cell debris and insoluble material from the denatured and solubilized proteins. This solubilized protein lysate was used as starting material for on-column refolding protocol.

The purification and refolding scheme employed for all the proteins is outlined in FIG. 3. The HCl or Urea denatured proteins in 5 ml denaturation buffer were loaded on a 2 ml column of preequilibrated Ni$^{2+}$-NTA agarose (Qiagen, GmBH, Germany), preequilibrated with denaturation buffer and the column incubated for 2 hour at room temperature. The column was then shifted to 16° C. and the rest of the protocol was performed at this temperature only except for DevR which was performed only at RT.

The unbound protein which includes the other contaminating proteins along with the excess of His$_6$-tagged specific protein was collected as flow through. The column was washed with 3 bed volumes (6 ml) of denaturation buffer containing 20 mM imidazole and then washed stepwise with decreasing concentrations of urea (8 M to 1 M) or Gm.HCl (6 M to 0 M) in 4 ml of refolding buffer (20 mM Tris.HCl, pH 8.0, 500 mM NaCl, 10% glycerol, 20 mM imidazole, 0.5 mM of oxidized glutathione [GSSG] and 5 mM reduced glutathione [GSH]).

The column was finally washed with 2 bed volumes (4 ml) of refolding buffer without urea or Gm.HCl to remove contaminating *E. coli* proteins. The bound protein was eluted with 5 ml refolding buffer containing 200 mM-500 mM (optimally 250 mM ) imidazole in fractions of 1 ml. The use of GSSG and GSH in the refolding buffer provides a good indication of the redox milieu of the column. As the GSSG/GSH entered the column, the oxidation state of $Ni^{2+}$ changed and the matrix color also changed gradually from bluish white to white and finally pinkish white. During elution with buffer containing 250 mM imidazole, the color or the $Ni^{+2}$-resin returned to blue because of releasing of the immobilized protein which restored the oxidation state of Ni ions, hence serving as a useful indicator of elution of refolded protein.

The eluted fractions/eluates were checked by SDS-PAGE or Bradford's reagent and the peak fractions (generally fraction #3-10) were pooled, dialyzed against dialysis/storage buffer (50 mM Tris.HCl, pH 8.0, 50 mM NaCl, 50% glycerol; 0.1 mM DTT) and stored at −20° C.

The refolded and purified protein/s were quantitated by BCA protein assay kit (Pierce Biochemicals, USA) or Bradford method of protein estimation using BSA as standard (Bradford, 1976). All the proteins were judged to be more than ~90% pure on SDS-PAGE analysis (FIG. 4).

The DevR protein and the mutant derivatives thereof were purified essentially as described above except for the modifications listed herewith:

a. The removal of denaturant (guanidinium hydrochloride/urea) was done in one step. The column was washed with 3-4 bed volumes (6-8 ml) 6 M Gm.HCl containing denaturation buffer after collecting the flow through. The column was then washed directly with 3-4 bed volumes of refolding buffer to remove the denaturant and also to facilitate rapid refolding of protein.

b. The elution of refolded protein was performed with 250 mM imidazole in refolding buffer. The eluted fractions were collected at RT as 0.5 ml aliquots in 1.5 ml microfuge tubes containing 0.5 ml cold 1M L-arginine. The aliquots were mixed by inverting immediately after collection. 8-10 such aliquots were collected during each typical purification. The presence of L-arginine prevented aggregation of the protein and enhanced the stability of the refolded protein for prolonged durations of time (up to a week at room temperature).

$DevRN_{145}$ protein was also localized to the soluble fraction after separation of the soluble and insoluble fractions. Though a large amount of protein was still localized to the insoluble inclusion bodies there was sufficient amount of soluble protein in the soluble cell lysate for purification of the protein in soluble form without refolding. For this the protocol mentioned in the following paragraphs was successfully utilized, essentially as per the manufacturer's protocol for purifying $His_6$-tagged proteins from the soluble fraction (Qiagen, Germany).

Besides $DevRN_{145}$, slow induction of all the other aforementioned proteins at sub-optimal conditions like growth in LB media at 25° C. with slow stirring for 16-20 hours with 0.2 mM IPTG for inducing also provided very small amounts of soluble native protein which though is very less for kinetics analysis and studies, but still can be used as a reproducible source of soluble protein for screening steps.

Similarly, induction of large culture volumes of proteins at multiple expression conditions including the optimal expression conditions, viz. 1 mM IPTG as inducer, 37° C. for 4-6 hours also provides a very small quantity of soluble, native protein and can be used for circumventing the refolding steps. Such large volume inductions can be achieved quite efficiently using small or medium scale fermenters and consequently a reasonable amount of soluble form of respective proteins can also be produced for the assay mentioned herein this patent application.

But, despite the advantages of the soluble protein, the limiting amount of aforementioned soluble proteins restricts its use in high-throughput screening assays wherein large quantities of proteins are desired. Hence the refolding approach offers the 'crucial' cutting edge advantage in the respect.

Briefly, all the solubilized proteins were purified as per the protocol mentioned below.

The soluble protein fraction obtained after the sonication step as mentioned above loaded on $Ni^{+2}$-NTA resin column preequilibrated with wash buffer (20 mM Tris.HCl, pH~8.0; 50 mM NaCl; 10% glycerol; 20 mM imidazole). The supernatant was allowed to equilibrate with the resin for 15-20 minutes at 16° C.

The flow through was collected slowly and the column was washed rapidly with 10-15 bed volumes of wash buffer.

The immobilized protein was eluted with 250 mM imidazole in wash buffer. The eluted fractions and eluates were checked by SDS-PAGE or Bradford's reagent and the peak fractions (generally fraction #3-7) were pooled, dialyzed against dialysis/storage buffer (50 mM Tris.HCl, pH 8.0, 50 mM NaCl, 50% glycerol; 0.1 mM DTT) and stored at −20° C.

Aliquot all the proteins in small aliquots and store at −20° C. till further use.

Example 2

Studies of Autophosphorylation Activity of DevS and Rv2027c Proteins $DevS_{201}$, $DevS_{578}$ and $Rv2027_{194}$ proteins and their mutant derivatives $DevS_{201}$-H395Q, $DevS_{201}$-H397Q, $DevS_{201}$-H397A, $DevS_{201}$-N503D and $Rv2027_{194}$-H392Q were subjected to autophosphorylation with $[\alpha^{32}P]$ ATP as phosphodonor molecule.

Purified and refolded protein/s (15 μM of $DevS_{201}$ or $Rv2027_{194}$ or their mutagenic variants thereof and 2.5 μM of $DevS_{578}$) were incubated with 5 μCi of $[\alpha^{32}P]ATP$ (5000 Ci/mmol, BRIT, CCMB campus, Hyderabad, India) in 10 μl reaction buffer (50 mM Tris.HCl, pH 8.0, 50 mM KCl, 10 mM MgCl2, 50 μM ATP) at 25° C. for the designated periods of time. After which the reactions were terminated by addition of 5 μl 3× sample buffer containing 250 mM Tris.HCl, pH 6.8, 10% glycerol, 1% SDS, 280 mM β-mercaptoethanol, 0.01% bromophenol blue.

The samples were immediately frozen on chilled ethanol bath and stored at −70° C. until just prior to analysis by SDS-PAGE.

Prior to SDS-PAGE analysis, samples were thawed on ice (if frozen) loaded onto a 12.5% (for autophoshorylation reactions) or 15% (for phosphotransfer reactions) gel and electrophoresed according to the established protocol (Fritsch and Sambrook, 2001) till the lower bromo-phenol dye had escaped the gel. The gel was the rinsed in water for 10 minutes and subjected to autoradiography after wrapping in plastic wrap at 4° C. for 4-16 hours.

Quantitation of radioactivity was performed by aligning the autoradiogram with the wet gel and then excising the corresponding bands from the gel using clean sterile blade. The excised bands corresponding to the Radiolabelled proteins were then counted using liquid scintillation counter (Wallac, DSA1409) in liquid scintillation fluid (OptiSync HiSafe).

For the autophosphorylation reactions of the sensor kinases, the following observations were made:

1. $DevS_{201}$, $DevS_{578}$ and $Rv2027_{194}$ proteins underwent autophosphorylation by phosphotransfer from $\gamma[^{32}P]$ ATP to the conserved histidine residue/s. The incorporation of $^{32}P$ was not due to non-specific binding of ATP to the proteins. This was confirmed by using $\gamma[^{32}P]ATP$ in place of $\gamma[^{32}P]ATP$ in the phosphorylation reaction which did not lead to protein phosphorylation.
2. The time course studies and stability analysis of the phosphorylated products revealed that incorporation of $^{32}P$ in the proteins was maximum at 4 hrs. with ~98% incorporation taking place in 1 hour for both $DevS_{201}$ and $DevS_{578}$ and 82% incorporation taking place for $Rv2027_{194}$ (FIG. 5A, 5B, 5C). The stability of the phosphorylated products was assessed in the presence and in the absence of $\gamma[^{32}P]ATP$; the products were absolutely stable for at least 4 hr. for $DevS_{201}$ and upto 20 hours for $Rv2027_{194}$ (FIG. 6). This intrinsic stability of the phosphorylated sensor kinases would facilitate their use in screening assays (Step 2 in FIG. 1).
3. The $DevS_{201}$ and $DevS_{578}$ autophosphorylation activities were optimal in the presence of $Mg^{2+}$ ions while $Mn^{2+}$ could substitute for $Mg^{2+}$ at ~40% lower efficiency and $Co^{2+}$ at ~25% efficiency (FIGS. 7A, B). For $Rv2027_{194}$ also the optimal divalent cation was $Mg^{2+}$ and $Mn^{2+}$ could substitute at ~40% lower efficiency while $Co^{2+}$ could substitute with ~25% efficiency. Whereas DevS was unable to utilize $Ca^{2+}$ in place of $Mg^{2+}$ $Rv2027_{194}$ utilized $Ca^{2+}$ as the divalent cation with a ~50% lower efficiency at 25 mM concentration (FIG. 7C). This ability to utilize different divalent ions is also indicative of possible difference in their activities and mode of stimuli detection processes utilized by them. In the absence of any divalent cations, the reaction failed to proceed. The optimal concentration of the $Mg^{+2}$ ions was 25 mM for DevS and 1 mM for $Rv2027_{194}$.
4. By site directed mutagenesis and chemical stability analysis it was confirmed that the site of phosphorylation was $His^{395}$ in DevS and His392 in Rv2027c. In DevS the $His^{397}$ residue situated in the proximity of $His^{395}$ was not phosphorylated by ATP (FIGS. 8A, B, C).
5. Mutation of $Asn^{503}$ in the putative ATP-binding pocket of DevS also abolished phosphorylation of $DevS_{201}$ indicating that ATP binding was mandatory for phosphorylation (FIG. 8A).

Example 3

Phosphorylation Activity of DevR

To study the phosphotransfer reaction, $DevS_{201}$/$Rv2027_{194}$ (15 µM) or $DevS_{578}$ (5 µM) was phosphorylated for 30 min as described above. Subsequently, DevR/$DevRN_{145}$ protein (20 µM) was added to $^{32}P$ phosphorylated sensor kinases. At indicated time points, aliquots were removed and stored at $-70°$ C. until analysis. Subsequently, the samples were analysed on 15% SDS-PAGE and subjected to autoradiography as described for autophosphorylation reactions.

The phosphorylation assays with the $DevRN_{145}$ and DevR mutant proteins were performed under identical conditions as described for the wild type DevR protein. The findings are provided below:

1. Phosphorylation of DevR/$DevRN_{145}$ by phosphotransfer from $DevS_{578}$, $DevS_{201}$ and $Rv2027_{194}$ occurred very rapidly. Within 2-5 minutes of the initiation of reaction, half of the radioactivity incorporated in the sensor kinases was transferred to DevR (FIGS. 9A, B, C, D, E). These rapid kinetics would be useful for screening of compounds/inhibitors against this step (Step 3 in FIG. 1 and example 4).
2. The transphosphorylation reaction from $DevS_{201}$~P to DevR was dependent on the presence of $Mg^{2+}$ ions in the reaction buffer (FIG. 9E). $Mn^{+2}$, $Ca^{+2}$ or $Co^{+2}$ could not substitute for $Mg^{+2}$ in phosphotransfer reaction. For $Rv2027_{194}$ and $DevS_{578}$ also, $Mg^{2+}$ could not be substituted by $Ca^{2+}$ or $Co^{2+}$ or $Mn^{+2}$ or $Fe^{+3}$ in the transphosphorylation reaction.
3. The DevR~P species was deduced to be very unstable in the presence of $DevS_{201}$. As revealed from FIGS. 9A and 9D after ten minutes of mixing of DevS and DevR/$DevRN_{145}$ neither of the two proteins (viz. DevS and DevR/$DevRN_{145}$) were detectable in their phosphorylated state. In the absence of $DevS_{201}$, phosphorylated DevR was stable for over 20 minutes, suggesting the presence of phosphatase activity within the sensor kinase.
4. During phosphotransfer from $DevS_{578}$ to DevR, DevR~P was stable upto 4 hrs. in the presence of $DevS_{578}$ at 4° C. (FIG. 9B) compared to a stability of only ~5 min in the presence of $DevS_{201}$. This difference in phosphatase activity between $DevS_{201}$ and $DevS_{578}$ can be ascribed to structural variation/s, since $DevS_{578}$ is the full length protein and is predicted to contain three hydrophobic patches corresponding to transmembrane regions, which could possibly rearrange in aqueous media in which the reaction had been performed. This also implicates the N-terminal sensory domain in masking the phosphatase activity localized in the C-terminal domain of the DevS sensor kinase.
5. The phosphotransfer from $Rv2027_{194}$ to DevR/$DevRN_{145}$ was quite similar to that from $DevS_{201}$, in that DevR~P/$DevRN_{145}$~P was not detectable after 10 min of initiation of reaction (point 3 above). This was suggestive of a phosphatase activity being associated with $Rv2027_{194}$. However, $Rv2027_{194}$~$^{32}P$ was detectable even at 30 min time point suggestive of a less efficient transphosphorylation capability in comparison to $DevS_{201}$ (FIGS. 9C, E).
6. Site-directed mutagenesis of the conserved residues as well as the acid-base stability analysis of the phosphorylated products revealed that the site of phosphorylation is the conserved $Asp^{54}$ in DevR. Mutations in other conserved residues $Asp^8$, which form the putative ion binding pocket and conserved invariant $Lys^{104}$ also abolished the phosphorylation of DevR (FIG. 10). Mutation in another conserved residue $Asp^9$ and also $Asp^{54}$ to Asn did not abolish the phosphorylation of DevR although it occurred less rapidly. This deviation was visible only when $DevS_{578}$ protein were used. Use of $DevS_{201}$ did not reveal this difference (compare panels 10A and 10B). This inconsistency may be ascribed to difficulty in resolving $DevS_{201}$ and DevR on account of very similar molecular mass as well as because of very low efficiency of phosphotransfer to DevR-$Asp^9$ mutant or because of some involvement of the N-terminal domain of the sensor kinase in executing such reactions. The position of these residues critical to function are shown in a model of DevR (FIG. 11).

Example 4

High-throughput Assays for Screening Compound Libraries/Inhibitors

To establish the high-throughput assays for autophosphorylation and phosphotransfer reactions to facilitate the screening of compound libraries, the reactions were performed in 96-well plate format as described below.

A. Autophosphorylation Reaction in High-Throughput Format.

Briefly, the autophosphorylation reaction was typical of all the sensor kinases as mentioned in example 2 in 10 μl reaction volume. After the phosphorylation reaction was performed for 60 minutes, it was terminated by 20 fold dilution in PBS. The phosphorylated reaction product/s were then filtered using vacuum manifold/suction device and 96-well Millipore HA-multiwell plates (multiwell plates with nitro-cellulose filters, but does not limit to this setup and can also include and accommodate 24-well or 384-well plates and automatic liquid handling systems etc. and their deviations/derivatives thereof) and then the filters were washed with 1 ml PBS per well at RT.

After this step the phosphorylated sensor kinase protein retained on the filter is essentially labeled and is reflective of the efficiency of the assay. To explain this, following experiments were performed in high-throughput format and are provided as examples i) Estimation of Optimal Protein amount for Autophosphorylation Assay.

To titrate the amount of sensor kinase protein/s for the autophosphorylation reaction, increasing amounts of DevS$_{201}$ (2.5-35 μM) and Rv2027$_{194}$ proteins (2-30 μM) were incubated in total 10 μl of reaction buffer (50 mM Tris.HCl, pH 8.0; 50 mM KCl; 25 mM MgCl2, 10 μM of ATP containing 2.5 μCi of [γ$^{32}$P]ATP [5000 Ci/mmol]) for 60 minutes at 25° C.

After the reaction the products were immediately added to individual filter well containing 200 μl of PBS (filters were previously wetted with 200 μl of PBS (For 1 liter NaCl, 8 g; KCl, 0.2 g; Na$_2$HPO$_4$, 1.44 g; KH$_2$PO$_4$, 0.24 g) by filtering it out). The diluted reaction products were filtered out after 2 minutes and the individual wells were then washed with 1 ml PBS (330 μl×3) using the vacuum suction and were dried briefly on vacuum (2-3 minutes). Subsequently the individual filters from the wells were removed using the semi-automatic filter removal device (Millipore Inc.) into individual scintillation vials and the radioactivity retained on each filter was estimated by liquid scintillation counting in Optisafe liquid scintillation fluid using the DSA1409 counter (Wallac, Inc.) in automatic data storage mode.

The Cpm incorporated in this assay was represented as a function of concentration of the sensor kinase used in the assay (FIG. 12). On this basis, 30 μM of DevS$_{201}$ (FIG. 12A) and 21 μM of Rv2027$_{194}$ (FIG. 12B), respectively was determined as the optimal concentration/amounts of proteins for use in 10 μl of autophosphorylation reaction. Sensor kinase/s were used at these optimal concentrations in all the subsequent high-throughput autophosphorylation reactions unless otherwise mentioned.

ii) Estimation of Optimal MgCl$_2$ Concentration for the Autophosphorylation of Sensor Kinase/s.

To titrate the optimal amount/concentration of the MgCl$_2$ for the autophosphorylation reactions the optimum amount of sensor kinase (as mentioned above) was incubated with various amounts of MgCl$_2$ (0.1-50 mM) and the entire reaction was essentially performed as described above.

The cpm incorporated in this assay was plotted as a function of MgCl$_2$ concentration and the optimal concentration for the autophosphorylation reaction was deduced. The DevS$_{201}$ protein showed a linear increase in radioactivity retention with increase in MgCl$_2$ concentration till last the concentration analyzed i.e. 50 mM (FIG. 13A) whereas Rv2027$_{194}$ showed maximum incorporation at 1 mM and thereafter the retention decreased on either decreasing or increasing the MgCl$_2$ concentration (FIG. 13B).

The presence of any phosphorylation inhibitor in these autophosphorylation assays would prevent incorporation of γ$^{32}$P-label in the sensor kinase protein hence the net retention of radioactivity cpm on the filter will decrease. Such a loss of the incorporation and retention of the label would be reflective of inhibition of the autophosphorylation reaction.

B. Phosphotransfer Reaction in High-throughput Format.

Similar to the autophosphorylation reaction, the phosphotransfer reaction/s taking place by virtue of phosphorylated sensor kinase protein/s were also performed in the high-throughput format. In such reactions the reduction in retained phosphorylation signal (radioactivity) from the membrane filter was estimated to ascertain the efficiency of transfer which occurs as a result of post-transfer dephosphorylation of response regulator.

To elaborate, first the autophosphorylation of the cytosolic derivatives of the respective sensor kinases were performed as described in the section above (i.e. 30 μM of DevS$_{201}$ in presence of 25 mM MgCl$_2$ and 10 μM of ATP and 21 μM of Rv2027$_{194}$ in presence of 1 mM of MgCl$_2$ and 10 μM of ATP) and since the phosphorylated forms of sensor kinases are very stable, the net phosphorylation of the sensor kinases were estimated by the same filter-retention assay as mentioned above.

Subsequently in the second step, increasing amounts of the DevR protein was added to the assay mixture. The presence of DevR protein in assay mixture for a period exceeding 10-15 minutes not only causes transfer of phosphoryl moiety from sensor kinase of DevR protein but also leads to dephosphorylation of both the interacting partners viz. sensor kinase and response regulator proteins causing a net reduction in the phosphoryl-label retention. The entire reaction is essentially performed as described for the autophosphorylation reaction of the sensor kinase after the transphosphorylation event.

Hence, this assay shows a net reduction in the radioactivity retained on the filter when compared to the reactions wherein no DevR protein was added, i.e. only autophosphorylation reactions. This decrease in label retention on the filter is accounted by transphosphorylation reaction followed by dephosphorylation and is highly proportionate with the amount of response regulator protein DevR in the reaction mixture (FIGS. 14A and 14B). In a generalized representation, addition of DevR (20 μM) protein to phosphorylated sensor kinase and subsequent incubation for 15-20 minutes at RT led to net reduction in retention of radiolabel (more than 80%) in the sensor kinase due to phosphotransfer and subsequent dephosphorylation reaction of DevR (FIG. 15).

In a high-throughput format screening of inhibitors for this step (phosphotransfer reaction), presence of a true inhibitor will not lead to reduction of retention of radioactivity on the filter. In other words the label retained would be more than the true phosphotransfer reaction and might be close to the one wherein no DevR has been added, indicating towards the degree of inhibition (FIG. 15).

Since both these autophosphorylation and transphosphorylation assays in this format are quantitative in nature, they can also be effectively utilized to compare the degree, strength, or percentage of inhibition or modulation caused by various molecules or compounds towards the participating proteins and their reactions in the disclosed pathways.

High through put assays for screening libraries, inhibitors {Eg.4).
a) The assays were developed based on the (i) onto phosphorylation characteristics of sensor kinases Dev5, Rv2027 and (ii) Phosphotransfer properties of response regulator DevR and its N terminal derivatives (DevR $N_{145}$).
b) This performance was optimized with reference to protein concentration and metal ion ($Mg^{2+}$) concentration.
c) Such high through put assays have not been developed for assaying sensor kinases and response regulation for any system including *M. tuberculosis*.

Example 5

Ethidium Bromide (EtBr) and Bromo Phenol Blue (BPB) and Their Derivatives as Candidate Inhibitor Compounds/Molecules as Potential Inhibitor/s of the Autophosphorylation Reaction of Sensor Kinase/s The known two-component system inhibitor/compounds like imidazolium salts, cyclohexene derivatives, tyramine-motif containing compounds, benzoxazines, cis-fatty acids, benzimidazole derivatives etc. had relatively similar structure and were of quite defined chemical nature viz. heterocyclicity and/or halogenation and/or azotization of the heterocylic compounds.

Utilizing this knowledge a few compounds were tested for their inhibitory activity on the autophosphorylation potential of DevS sensor kinase. These included levamisole, folic acid, glycyl glycyl glycine, ethidium bromide, bromo phenol blue, 2-4-hydroxyphenylazo benzoic acid (HABA), 2-mercapto benzimidazole etc. All the compounds were tested at 1 mM concentration in the assay.

To elaborate, 12 µM of $DevS_{201}$ was incubated with the aforementioned compounds in the phosphorylation reaction buffer (50 mM Tris.HCl, pH 8.0, 50 mM KCl and 25 mM $MgCl_2$) for 30 minutes at room temperature. The autophosphorylation reaction was initiated by the addition of 2.5 µCi of [$\gamma^{32}P$]ATP and 50 µM of carrier ATP. The reaction contents were mixed and incubated for an additional 60 minutes at 25° C. for phosphorylation. Subsequently, the reactions were terminated and analyzed on SDS-PAGE as mentioned previously.

In such a reaction, 1 mM concentration of ethidium bromide (Phenanthridinium, 3,8-diamino-5-ethyl-6-phenyl-, bromide) and BPB (3',3'',5',5''-Tetrabromophenol tetrabromosulfonapthalene) provided visible inhibition of the autophosphorylation of $DevS_{201}$ (FIG. 16A, lanes 5 and 7).

Further analysis of the inhibitory activity of EtBr and BPB on the autophosphorylation of the sensor kinases, $DevS_{201}$ and $Rv2027_{194}$ in a concentration course (from 2.5 mM to 1 µM in high-throughput format and 1 mM to 1 µM in SDS-PAGE format) demonstrated the following. The concentration of BPB required to cause 50% inhibition (IC50) of the autophosphorylation of both $DevS_{201}$ and $Rv2027_{194}$ was around 1.5-1.7 mM (FIGS. 17A, 17C). Compared to this, 50% inhibition of $DevS_{201}$ was not achieved within the tested upper limit of 2.5 mM but for Rv2027c IC50 value of EtBr was around 0.6-0.7 mM (FIGS. 18A, 18C). Inhibition with BPB and EtBr was reproduced in the SDS-PAGE format (FIGS. 17B, 17D and FIGS. 18B, 18D). After coomassie-staining of the same gel, no aggregation was observed in the EtBr and BPB-containing wells indicating that the autophosphorylation inhibition was not because of aggregation of the sensor kinase in the presence of these modalities, thereby confirming that the inhibition was genuine and not a false 'lead' as noted by other groups (Stephenson and Hoch, 2000).

Through these studies we propose the novel utilization of these compounds to generate derivatives as inhibitory agents of the autophosphorylation activity of DevS and Rv2027c sensor histidine kinases of the DevR-Devs and DevR-Rv2027c two-component signal transduction systems. Such utilization of these compounds has not been discussed or reported from any source whatsoever till date to the best of our knowledge and belief.

Although EtBr has been used as a drug or drug precursor, for example as a parasitotoxic, antiprotozoal drug for the treatment of Leishmaniasis, in combination therapeutic regimens using DNA reactive agents and studies have also been conducted in animals to evaluate EtBr as a potential anti tumorigenic chemotherapeutic agent (Kramer and Grunberg, 1973), no role for the same has been suggested towards inhibition of a sensor kinase and for DevS and Rv2027c in particular. In contrast, BPB or its derivatives have never been utilized or implicated as inhibitors of sensor kinase or any other enzyme whatsoever to the best of our knowledge and belief.

Similarly, the utility of 2-mercapto benzimidazole (2-MBI) was also tested as an inhibitor of the autophosphorylation reaction of both the sensor kinases ($DevS_{201}$ and $Rv2027_{194}$) in both SDS-PAGE and high throughput formats. The IC50 value of 2-MBI for both $DevS_{201}$ and $Rv2027_{194}$ autophosphorylation reaction was around 0.4-0.6 mM (FIGS. 19A and 19B), indicating the efficacy of the compound in inhibiting such reactions. Inhibition of the autophosphorylation reaction was also confirmed with SDS-PAGE format. Coomassie stained profile of the same gel indicated the absence of aggregate, confirming that the inhibition was genuine (not shown).

Benzimidazoles and their derivatives are established anti-microbial, anti-fungal, anti-helminthic and anti-ulcerative agents (Klimesova et al., 2002a; Masry et al., 2000). 2-MBI is the precursor compound used in the synthesis of anti-ulcerative compounds like Omeprazole and Lansprazole. Though the benzimidazoles have been utilized as successful anti-bacterial agents against gram-positive bacilli and there are a few reports of their utilization as anti-tubercular drugs in particular (Klimesova et al., 2002b).

Besides these uncharacterized bactericidal effects of benzimidazoles, they are also reported as inhibitors of two-component systems, specifically 2-phenylbenzimidazole and its derivatives. Though these compounds demonstrated a high in vitro activity with IC50 value of 4 µM for one of the derivatives, and had good anti-bacterial activity against susceptible and resistant gram-positive bacteria, the potency in the biochemical assay did not correlate well with anti-bacterial activity in this series, suggesting another mechanism might be operative (Deschenes et al, 1999).

The results disclosed herein demonstrated the efficacy of 2 mercapto benzimidazole in specifically inhibiting autophosphorylation reaction of the sensor kinases and propose their novel utilization based on their mode of action in anti-tubercular therapy and against DevR-DevS and/or DevR-Rv2027c signal transduction pathways in particular.

Ethidenin bromide (EERV) and bromophenol blue (BPE) inhibits autophosphorylation activity of DevS and Rv20287C. Therefore they have potential to serve as starting point to develop more patent inhibitors.

a) E&Br has been used as a precursor for generating a parasitotoxic, antiportozoal drug. However, no role for the same has been suggested towards inhibition of sensor kinase from any source whatsoever or as a precursor for antibubercular drug development.

b) BPB has never been utilized or implicated as inhibitor in any biological system/enzyme. Therefore, this is a novel reported use. It is used as a dye during electrophoresis of proteins and nucleic acids.

c) 2-mercaptobenzimidazole also inhibited autophosphorylation reaction of DevS and Rv2027c.

Apart from these above, it is noteworthy that inhibition in autophosphorylation noted earlier reports was because of protein aggregate. In contrast in the examples provided herein, protein aggregation did not occur at all and inhibitor was true and genuine.

The experiments described herein provide the first evidence of the bonafide nature of DevR-DevS two-component system and that of cross talk or cross communication between Rv2027c and DevR at biochemical level involving phosphorylation of the respective proteins. The DevR-DevS two-component system represents the third example of a two-component system being involved in virulence of *M. tuberculosis*, the other two-component systems of *M. tuberculosis* for whom roles in virulence has been reported being Rv0981-0982 (Zahrt and Deretic, 2001) and phoP (Perez et al., 2001).

Since, hypoxia has been recognized as a key signal for the DevR-DevS two-component system, it would be reasonable to suggest its involvement in latent infection, a unique characteristic of tubercle bacilli. Furthermore, the other two component systems that have been implicated in virulence are yet to be characterized at the biochemical level and hence as of now cannot be utilized for high throughput screening for lead molecules. It is therefor reasonable to believe that the DevR-DevS system, regulates the expression of one or more genes induced during hypoxia. Therefore, this invention offers the means of screening for new anti-microbial or anti-bacterial drugs, compounds, agents, or molecules which by blocking DevR and DevS/Rv2027c activity could effectively interfere with the activity of one or many gene products associated with bacterial/mycobacterial survival and dormancy.

In addition to the DevR-DevS/DevR-Rv2027c two-component systems serving as targets for anti-tubercular drug development at novel intervention step or stages, the use of two-component systems in a tuberculosis inhibitor screening is also new. The availability of high-throughput protocol or setup facilitates rapid screening of huge number of potential pharmacophores, compounds, agents or molecules as inhibitors for any stage of the phosphorylation pathway as revealed herein (FIG. 1, steps 2 and 3). The availability of mutant proteins of all the participating proteins would also facilitate utilization of phage-displayed peptide libraries/random-peptide libraries/phage-displayed synthetic antibody libraries in the identification of potentially 'significant' and/or 'correct' lead peptides and elimination of 'false' leads, which can be utilized as peptide inhibitors in subsequent assays.

The most potent inhibitors of sensor kinases exert their effect by causing structural laterations of the kinase leading to aggregation in contrast BPB, ETBr or 2 MBI do not cause aggregation. they therefore represent novel and true inhibitors of sensor kinases DevS and Rv2027c.

The present invention is not to be limited in scope by the specific embodiments described herein, which are intended as single illustrations of individual aspects of the invention, and functionally equivalent methods and components are within the scope of the invention. Various publications are cited herein, the contents of which are hereby incorporated by reference in their entireties.

REFERENCES OF THE PRESENT INVENTION

Anderson D. H., Harth G., Horwitz M. A. and Eisenberg D. (2001) An interfacial mechanism and a class of inhibitors inferred from two crystal structures of the *Mycobacterium tuberculosis* 30 kDa major secretory protein (Antigen 85B), a mycolyl transferase. J. Mol. Biol. 307, 671-681.

Armitige, L. Y., Jagannath, C., Wanger, A. R. and Norris, S. J. (2000) Disruption of gene encoding antigen 85A and 85B of *Mycobacterium tuberculosis* H37Rv: Effect on growth in culture and in macrophages. Infect. Immun. 68, 767-78.

Baikalov, I., Schroder, I., Kaczor-Grzeskowiak, M., Grzeskowiak, K., Gunsalus, R. P. and Dickerson, R. E. (1996) Structure of the *Escherichia coli* response regulator NarL. Biochemistry 35, 11053-11061.

Baltch, A. L., Smith, R. P., Ritz, W. J. and Bopp, L. H. (1998) Comparison of inhibitory and bactericidal activities and postantibiotic effects of LY333328 and Ampicillin used singly and in combination against vancomycin-resistant *Enterococcus faecium*. Antimicrob. Agents Chemother. 42, 2564-2568.

Barrett, J. F. and Hoch, J. A. (1998) Two-component signal transduction as a target for microbial anti-infective therapy. Antimicrob. Agents Chemother. 42, 1529-1536.

Barry, C. E. III, Slayden, R. A., Simpson, A. E. and Lee, R. E. (2000) Use of genomics and combinatorial chemistry in the development of new antimycobacterial drugs. Biochem. Pharmacol. 59, 221-231.

Boon, C., Li, R., Qi, R. and Dick, T. (2001) Proteins of *Mycobacterium bovis* BCG induced in Wayne dormancy model. J. Bacteriol. 182, 2672-2676.

Bradford, M. M. (1976) A rapid and sensitive method for the quantitation of microgram quantities of protein utilizing the principle of protein-dye binding. Anal. Biochem. 72, 248-254.

Chen, P., Ruiz, R. E., Li, Q., Silver, R. F. and Bishai, W. R. (2000) Construction and characterization of *M. tuberculosis* mutant lacking the alternate sigma factor, sigF. Infect. Immun. 68, 5575-5580.

Cole, S. T., Brosch, R., Parkhill, J., Garnier, T., Churcher, C., Harris, D., Gordon, S. V., Eiglmeier, K., Gas, S., Barry, C. E. III, Tekaia, F., Badcock, K., Bashyam, D., Brown, D., Chillingworth, T., Connor, R., Davies, R., Devlin, K., Feltwell, T., Gentles, S., Hamlin, N., Holroyd, S., Hornsby, T., Jagels, K., Krough, A., McLean, J., Moule, S., Murphy, L., Oliver, K., Osborne, J., Quail, M. A., Rajandream, M. A., Rogers, J., Rutter, S., Seeger, K., Skelton, J., Squares, R., Squares, S., Sulston, J. E., Taylor, K., Whirehead, S. and Barrel, B. G. (1998) Deciphering the biology of *Mycobacterium tuberculosis* from the complete genome sequence. Nature 393, 537-544.

Collins D. M., Kawakami R. P., de Lisle G. W., Pascopella L., Bloom B. R. and Jacobs W. R. Jr. (1995) Mutation of the principal sigma factor causes loss of virulence in a strain of the *Mycobacterium tuberculosis* complex. Proc. Natl. Acad. Sci. USA 92, 8036-8040.

Cooper J. B., McIntyre K., Badasso M. O., Wood S. P., Zhang Y., Garbe T. R. and Young, D. (1995) X-ray structure analysis of the iron-dependent superoxide dismutase from

*Mycobacterium tuberculosis* at 2.0 Angstroms resolution reveals novel dimer-dimer interactions. *J. Mol. Biol.* 246, 531-544.

Cox J. S., Chen B., McNeil M. and Jacobs W. R. Jr. (1999) *Nature* 402, 79-83.

Dasgupta, N., Kapur, V., Singh, K. K., Das, T. K., Sachdeva, S., Jyothisri, K. and Tyagi, J. S. (2000) Characterization of a two-component system, devR-devS, of *Mycobacterium tuberculosis*. *Tuber. Lung Dis.* 80, 141-159.

DeMaio J., Zhang Y., Ko C., Young D. B. and Bishai W. R. (1996) A stationary-phase stress-response sigma factor from *Mycobacterium tuberculosis*. *Proc. Natl. Acad. Sci.* (USA) 93, 2790-2794.

Denis, A., Agouridas, C., Auger, J-M., Benedetti, Y., Bonnefoy, A., Bretin, F., Chantot, J. F., Dussarat, A., Fromentin, C., D'Ambrieres, S. G., Lachaud, S., Laurin, P., Le Martret, O., Loyau, V., Tessot, N., Pejac, J. M. and Perron S. (1999) Synthesis and antibacterial activity of HMR 3647, a new ketolide highly potent against erthryomycin-resistant and susceptible pathogens. *Bioorg. Med. Chem. Lett.* 9, 3075-3080.

Deschenes, R. J., Lin, H., Ault, A. D. and Fassler, J. S. (1999) Antifungal properties and target evaluation of three putative bacterial histidine kinase inhibitors. *Antimicrob. Agents Chemother.* 43, 1700-1703.

Domagala, J. M., Alessi, D., Cummings, M., et al. (1998) Bacterial two-component signalling as a therapeutic target in drug design: Inhibition of NRII by diphenolic methanes (bisphenols). *Adv. Exp. Med. Biol.* 456,269-286.

Doukhan, L., Predich, M., Nair, G., Dussurget, O., Mandic-Mulec, I., Cole, S. T., Smith, D. R. and Smith, I. (1995) Genomic organization of the mycobacterial sigma gene cluster. *Gene* 165, 67-70.

Dziejman, M. and Mekalanos, J. J. (1995) two-component signal transduction and its role in the expression of bacterial virulence factors in Hock, J. A. and Silhavy, T. J. Eds. Two component signal transduction. Washington, D.C. American Society for Microbiology. Pp. 305-317.

El-Masry, A. H., Fahony, H. H. and Abdelwahed, S. H. A. (2000) Synthesis and anti microbial activity of some new benzimidazole derivatives. *Molecules* 5, 1429-1438.

Frechette, R. F., Beach, M. J., Bernstein, J. et al. (1997) Novel benzoxazine derivatives with inhibitory activity against bacterial two-component signal transduction systems. Book of Abstracts, 214th ACS National Meeting, Las Vegas, Nev., USA.

Glickman M. S., Cox J. S. and Jacobs W. R. Jr. (2000) *Mol. Cell.* 5, 717-727.

Glickman, M. S., Cox, J. S. and Jacobs, W. R. Jr. (2000) A novel mycolic acid cyclopropane synthetase is required for coding, persistence and virulence of *Mycobacterium tuberculosis*. *Mol. Cell* 5, 717-727.

Grange, J. M. (1992) The mystery of the mycobacterial 'persistor'. *Tuber. Lung Dis.* 73, 249-251.

Haydel, S. E., Dunlap, N. E. and Benjamin, W. H. Jr. (1999) In vitro evidence of two-component system phosphorylation between the *Mycobacterium tuberculosis* TrcR/TrcS proteins. *Micro. Patho.* 26 195-206.

Himpens, S., Locht, C. and Supply, P. (2000) Molecular characterization of the mycobacterial SenX3-RegX3 two-component system: evidence for autoregulation. *Microbiol.* 146, 3091-3098.

Jackson, M., Crick, D. C. and Brennan, P. J. (2000) Phosphatidylinositol is an essential phospholipid of mycobacteria. *J. Biol. Chem.* 275, 30092-30099.

Kapur, V. (2001) Ph.D. Thesis. Submitted to All India Institute of Medical Sciences, New Delhi, India.

Kinger, A. K. and Tyagi, J. S. (1993) Identification and cloning of genes differentially expressed in the virulent strain of *Mycobacterium tuberculosis*. *Gene* 131, 113-117.

Klimesova, V., Koc, J., Pour, M., Stachel, J., Waisser, K. and Kaustova, J. (2002a) Synthesis and preliminary evaluation of benzimidazole derivatives as antimicrobial agents. *Eur. J. Med. Chem.* 37,409-418.

Klimesova, V., Koc, J., Waisser, K. and Kaustova, J. (2002b) New benzimidazole derivatives as antimycobacterial agents. *Framco* 57, 259-265.

Kramer, M J and Grunberg, E. (1973) Effect of ethidium bromide against transplantable tumors in mice and rats. *Chemotherapy*, 19, 254-258.

Phetsuksiri, B., Baulard, A. R., Cooper, A. M., Minnikin, D. E., Douglas, J. D., Besra, G. S. and Brennan, P. J. (1999) Antimycobacterial activities of isoxyl and new derivatives through the inhibition of mycolic acid synthesis. *Antimicrob. Chemother.* 43, 219-226.

Li, Z., Kelley, C., Collins, F., Rouse, D. and Morris, S. (1998) Expression of katG in *Mycobacteriun tuberculosis* is associated with its growth and persistence in mice and guinea pigs. *J. Infect. Dis.* 177, 1030-1035.

Macielag, M. J. and Goldschmidt, R. (2000) Inhibitors of bacterial two-component signalling system. *Exp. Opin. Invest. Drugs* 9, 2351-2369.

Manganelli, R., Voskuil, M. I., Schoolnik, G. K. and Smith, I. (2001) The *Mycobacterium tuberculosis* ECF sigma factor sigmaE: role in global gene expression and survival in macrophages. Mol. Microbiol. 41, 423-437.

Matsushita, M. and Janda, K. D. (2002) Histidine kinases as targets for new antimicrobial agents. *Bioor. Med. Chem.* 10, 855-867.

Mayuri, Bagchi, G., Das, T. K. and Tyagi, J. S. (2002) Molecular analysis of the dormancy response in *Mycobacterium smegmatis*. Expression analysis of the genes encoding DevR-DevS two-component system, Rv3134c and chaperone-crystalline homologues. *FEMS Microbiol. Lett.* 211, 231-237.

McKinney, J. D., Bentrup, K. H., Munoz-Elias, E. J., Miczak, A., Chen, B., Chen, W. T., Swenson, D., Sacchettini, J. C., Jacobs, W. R. Jr. and Russell, D. G.. (2000) Persistence of *M. tuberculosis* in macrophages and mice requires the glyoxylate shunt enzyme isocitrate lyase. *Nature* 406, 735-738.

Mitchison, D. A. (1998) How drug resistance emerges as a result of poor compliance during short-chemotherapy for tuberculosis. Int. J. Tuberc. Lung Dis. 2, 10-15.

Mukamolova G. V., Kaprelyants A. S., Young D. I., Young M. and Kell D. B. (1998) A bacterial cytokine. *Proc. Natl. Acad. Sci. USA.* 95, 8916-8921.

Parkinson, J. S. and Kofoid, E. C. (1992) Communication modules in bacterial signalling proteins. *Ann. Rev. Genet.* 26,71-112.

Parrish, N., Dick, J. D. and Bishai, W. R. (1998) Mechanisms of latency in *Mycobacterium tuberculosis*. *Trends Microbiol.* 6: 107-112.

Perez, E., Samper, S., Bordas, Y., Guilhot, C., Gicquel, B. and Martin, C. (2001) An essential role for phoP in *Mycobacterium tuberculosis* virulence. *Mol. Micro.* 41, 179-87.

Pohl, E., Holmes, R. K. and Hol, W. G. (1999) Crystal structure of the iron-dependent regulator (IdeR) from *Mycobacterium tuberculosis* shows both metal binding sites fully occupied. *J. Mol. Biol.* 285, 1145-1156.

Raman, S., Song, T., Puyang, X., Bardarov, S., Jacobs, W. R. Jr. and Husson, R. N. (2001) The alternative sigma factor SigH regulates major components of oxidative and heat stress responses in *Mycobacterium tuberculosis*. *J. Bacteriol*. 183, 6119-6125.

Ronning, D. R., Klabunde, T., Besra, G. S., Vissa, V. D., Belisle, J. T. and Sacchettini, J. C. (2000) Crystal structure of the secreted form of antigen 85C reveals potential targets for mycobacterial drugs and vaccines. *Nat. Struct. Biol.* 7, 141-146.

Roychoudhary, S., Zielinski, N. A., Ninfa, A. J., Allen, N. E., Jungheim, L. N., Nicas, T. I. and Chakrabarty, A. M. (1993) Inhibitors of two-component signal transduction systems: Inhibition of alginate gene activation in *Pseudomonas aerugin osa*. *Proc. Natl. Acad. Sci. USA*. 90, 965-969.

Sambrook, J. and Russell, D. W. (2001) in: Molecular Cloning. III Ed. CSHL Press, New York, USA.

Sherman, D. R., Voskuil, M., Schnappinger, D., Liao, R., Harrell, M. I. and Schoolnik, G. K. (2001) Regulation of the *Mycobacterium tuberculosis* hypoxia response gene encoding α-crystallin. *Proc. Natl. Acad. Sci. USA* 98, 7534-7539.

Stead, W. W. (1967) Pathogenesis of a first episode of chronic pulmonary tuberculosis in man: recrudescence of residuals of the primary infection or exogenous reinfection? *Am. Rev. Respir. Dis.* 95, 729-745.

Stead, W. W., Kerby, D. P., Schleuter, D. P. and Jordahl, C. W. (1968) The clinical spectrum of primary tuberculosis in adults. Confusion with reinfection in the pathogenesis of chronic tuberculosis. Ann. Intern. Med. 68, 731-745.

Stephenson, K., Yamaguchi, Y., Hoch, J. A. (2000) The mechanism of action of inhibitors of bacterial two-component signal transduction systems. *J. Biol. Chem.* 275, 38900

Stock, A. M., Robinson, V. L. and Goudreau, P. N. (2000) Two-component signal transduction. *Ann. Rev. Biochem.* 69, 183-215.

Stock, J. B., Surette, M. G., Levit, M. and Park, P. (1995) Two-component signal transduction systems: structure-function relationships and mechanisms of catalysis. In: Hock, J. A. and Silhavy, T. J. Eds. Two component signal transduction. Washington, DC. American Society for Microbiology. Pp. 25-51.

Stover, C. K., Warrener, P., VanDevanter, D. R., Sherman, D. R., Arain, T. M., Langhorne, M. H., Anderson, S. W., Towell, J. A., Yuan, Y., McMurray, D. N., Kreiswirth, B. E., Barry, C. E. III and Baker, W. R. (2000) A small molecule nitroimidaofuran drug candidate for treatment of tuberculosis. Nature 405, 962-66.

Strauch, M. A., De Mendoza, D. and Hoch, J. A. (1992) cis-Unsaturated fatty acids specifically inhibit a signal-transducing protein kinase required for initiation of sporulation in *B. subtilis*. *Mol. Microbiol.* 6, 2909-2917.

Ulijasz, A. T. and Weisblum, B. (1999) Dissecting the VanRS signal transduction pathway with specific inhibitors. *J. Bacteriol.* 181, 627-631.

Upton, A., Johnson, N., Sandy, J. and Sim, E. (2001) Arylamine N-acetyltransferases—of mice, men and microorganisms. *Trends Pharmacol. Sci.* 22, 140-146.

Urbanski, M. J., Xiang, M. A., Foleno, B. D. et al. (1997) Novel cyclohexene derivatives with histidine protein kinase inhibitory activity-potential new antibacterial agents. Book of Abstracts, 214th ACS National Meeting, Las Vegas, Nev., USA.

Wallis, N. G. (1999) Bacterial two-component signal transduction systems as drug targets. *Curr. Opin. Anti-infect. Invest. Drugs.* 1, 428-434.

Weber, I., Fritz, C., Ruttkowski, S., Kreft, A. and Bange, F.-C. (2000) Anaerobic nitrate reductase (narGHJI) activity of *Mycobacterium bovis* BCG in vitro and its contribution to virulence in immunodeficient mice. *Mol. Microbiol.* 35, 1017-1025.

West, M. L. and Fairlie, D. P. (1995) Targeting HIV-1 protease: a test of drug-design methodologies. *Trends Pharmacol. Sci.* 16, 67-94.

WHO report on the Global Tuberculosis Epidemic (1998) WHO Geneva.

Wilson T. M., de Lisle, G. W. and Collins, D. M. (1995) Effect of inhA and katG on isoniazid resistance and virulence of *Mycobacterium bovis*. *Mol. Microbiol.* 15, 1009-1015.

Yuan, Y., Crane, D. C., Simpson, R. M., Zhu, Y. Q., Hickey, M. J., Sherman, D. R. and Barry, C. E. III. (1998) The 16 kDa a-crystalline (Acr) protein of *Mycobacterium tuberculosis* is required for growth in macrophages. *Proc. Natl. Acad. Sci. USA* 95, $9_{578}$-9583.

Zahrt, T. C. and Deretic, V., (2000) An essential two-component signal transduction system in *Mycobacterium tuberculosis*. *J. Bacteriol.* 182, 3832-3838.

Zahrt, T. C and Deretic, V. (2001) *Mycobacterium tuberculosis* signal transduction system required for persistent infection. *Proc. Natl. Acad. Sci.* (USA) 98, 12706-11.

Zhang, Y. and Amzel, L. M. (2002) Tuberculosis drug targets. *Current Drug Design* 3, 131-154.

Patents

Inouye, M., Heiyoung, P, Mitsuhike, I. (2000) Methods of identifying inhibitors of sensor kinases through rational drug design. U.S. Pat. No. 6,162,627.

Tyagi, J. S. and Kapur, V. Indian patent application—"A process for identifying a novel target for the development of therapeutic modalities and drugs effective against *tuberculosis*". Appl. No. 1286/DEL/2001.

Tyagi, J. S. and Kapur, V. International PCT application "A process for identifying a novel target for the development of therapeutic modalities and drugs effective against tuberculosis". Appl. No. PCT/IN02/00022.

The invention claimed is:

1. A method for screening a test compound as a candidate for preventing *Mycobacterium tuberculosis* (*M. tuberculosis*) from entering the dormant stage in its life cycle, the method comprising:

a) providing a system, the system comprising a first and second member of a two-component signaling system, said members being individually expressed in *E. coli*, the first component being selected from the group consisting of a peptide comprising a catalytically active DevS domain and a catalytically active Rv2027c domain, and the second component comprising a catalytically active DevR domain, b) providing a stimulus to promote autophosphorylation of the first component both in the presence and absence of the test compound, and c) determining a difference in the relative levels of phosphorylation of the first component or relative levels of phosphorylation of the second component in the absence and presence of the test compound, wherein a difference between the levels of the phosphorylation of the phosphorylated first or phosphorylated second component in the presence of the test compound and the levels of the phosphorylation of the phosphorylated first or phosphorylated second component in the absence of the test compound, respectively, indicates that the test compound is a candidate for preventing *M. tuberculosis* from entering the dormant stage of the lifecycle.

2. The method of claim 1, wherein the DevS is selected from the group consisting of $DevS_{201}$, $DevS_{578}$, $DevS_{201}$-H395Q, $DevS_{201}$-H397Q, $DevS_{201}$-H397A, and $DevS_{201}$-N503D.

3. The method of claim 1, wherein the first component comprises the full-length $DevS_{578}$ protein.

4. The method of claim 1, wherein the DevR is selected from the group consisting of $DevRN_{145}$, the mutant protein DevR-D8N, the mutant protein DevR-D9N, the mutant protein DevR-D54V, the mutant protein DevR-D54N and the mutant DevR-K104E.

5. The method of claim 1, wherein the second component comprises the full-length DevR protein.

6. The method of claim 1, wherein the DevS is selected from the group consisting of $DevS_{201}$, $DevS_{578}$, $DevS_{201}$-H395Q, $DevS_{201}$-H397Q, $DevS_{201}$-H397A, and $DevS_{201}$-N503D and wherein the DevR is selected from the group consisting of $DevRN_{145}$, the mutant protein DevR-D8N, the mutant protein DevR-D9N, the mutant protein DevR-D54V, the mutant protein DevR-D54N and the mutant DevR-K104E.

7. The method of claim 1, wherein the first and second components comprise full length DevS and DevR proteins, respectively.

8. The method of claim 1, wherein the Rv2027c is selected from the group consisting of $Rv2027_{194}$ and $Rv2027_{194}$H392Q.

9. The method of claim 1, wherein the Rv2027c is selected from the group consisting of $Rv2027_{194}$ and $Rv2027_{194}$H392Q, and wherein the DevR is selected from the group consisting of $DevRN_{145}$, the mutant protein DevR-D8N, the mutant protein DevR-D9N, the mutant protein DevR-D54V, the mutant protein DevR-D54N and the mutant DevR-K104E.

10. The method of claim 1, wherein phosphorylation levels are determined in high-throughput format or by performing SDS-PAGE.

* * * * *